US008633002B2

(12) United States Patent
Roessler et al.

(10) Patent No.: US 8,633,002 B2
(45) Date of Patent: Jan. 21, 2014

(54) MICROBIAL PRODUCTION OF FATTY ALCOHOLS

(75) Inventors: Paul G. Roessler, San Diego, CA (US); Kevin Watts, Minneapolis, MN (US); Bo Liu, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 45 days.

(21) Appl. No.: 12/854,848

(22) Filed: Aug. 11, 2010

(65) Prior Publication Data

US 2011/0195469 A1 Aug. 11, 2011

Related U.S. Application Data

(60) Provisional application No. 61/233,109, filed on Aug. 11, 2009.

(51) Int. Cl.
*C12P 7/02* (2006.01)
*C12P 7/00* (2006.01)

(52) U.S. Cl.
USPC .......................................... 435/155; 435/132

(58) Field of Classification Search
USPC ................................................ 435/155, 132
See application file for complete search history.

(56) References Cited

U.S. PATENT DOCUMENTS

| 6,143,538 | A | 11/2000 | Somerville et al. |
| 2004/0237144 | A1 | 11/2004 | Selvaraj et al. |
| 2009/0148918 | A1 | 6/2009 | Trimbur et al. |
| 2010/0105963 | A1* | 4/2010 | Hu ................................. 568/840 |
| 2010/0251601 | A1* | 10/2010 | Hu et al. ......................... 44/313 |
| 2010/0317071 | A1* | 12/2010 | Hamelers et al. ............. 435/134 |

FOREIGN PATENT DOCUMENTS

| WO | WO 2007/136762 A2 | 11/2007 |
| WO | WO2008/119082 | 10/2008 |

OTHER PUBLICATIONS

Art of Record: Nielsen et al. Identification of prokaryotic and eukaryotic signal peptides and prediction of their cleavage sites. Protein Engineering (1997) 10(1): 1-6.*
Copeland et al., GenBank CP000514.1. Marinobacter aquaeolei VT8, complete genome (May 6, 2009). This reference can be viewed at the below url: <http://www.ncbi.nlm.nih.gov/nuccore/120322793>.
Van Dijck et al., "Truncation of *Arabidopsis thaliana* and *Selaginella lepidophylla* trehalose-6-phosphate synthase unlocks high catalytic activity and supports high trehalose levels on expression in yeast", *Biochem. J.*, 366(Pt 1):63-71 (2002).
Wahlen et al., "Purification, characterization, and potential bacterial wax production role of an NAPDH-dependent fatty aldehyde reductase from *Marinobacter aquaeolei* VT8", *Appl. Environ. Microbiol.*, 75(9):2758-2764 (2009).
Domergue et al., "Three *Arabidopsis* Fatty Acyl-Coenzyme A Reductases, FAR1, FAR4, and FAR5, Generate Primary Fatty Alcohols Associated with Suberin Deposition", Plant Physiology 153:1539-1554, 2010.
Gupta et al., "Expression of the *Photorhabdus luminescens* lux genes (luxA, B, C, D, and E) in *Saccharomyces cerevisiae*", FEMS Yeast Research 4:305-313, 2003.
Honsho et al., "Postranslational Regulation of Fatty Acyl-CoA Reductase 1, Far1 Controls Ether Glycerophospholipid Synthesis", J. Biological Chemistry 285(12):8537, 2010.
Ishige et al., "Long-Chain Aldehyde Dehydrogenase That Participates in n-Alkane Utilization and Wax Ester Synthesis in *Acinetobacter* sp. Strain M-1", Appl. Environ. Microbiol. 66(8):3481, 2000.
Kunst et al., "Biosynthesis and secretion of plant cuticular wax", Progress in Lipid Research 42:51-80, 2003.
Lienard et al., "Evolution of multicomponent pheromone signals in small ermine moths involves a single fatty-acyl reductase gene", PNAS 107(24):10955-10960, 2010.
Meighen, "Bacterial bioluminescence: organization, regulation and application of the lux genes", The FASEB Journal 7:1016-1022, 1993.
Metz et al., "Purification of a Jojoba Embryo Fatty Acyl-Coenzyme A Reductase and Expression of Its cDNA in High Erucic Acid Rapeseed", Plant Physiology 122:635-644, 2000.
Morgan-Kiss et al., "The *Escherichia coli* fadK (ydiD) Gene Encodes an Anerobically Regulated Short Chain Acyl-CoA Synthetase", J. Biological Chemistry 279(36):37324-37333, 2004.
Moto et al., "Pheromone gland-specific fatty-acyl reductase of the silkmoth, *Bombyx mori*", PNAS 100(16):9156-9161, 2003.
Pighin et al., "Plant Cuticular Lipid Export Requires an ABC Transporter", Science 306:702, 2004.
Reiser et al., "Isolation of Mutants of *Acinetobacter calcoaceticus* Deficient in Wax Ester Synthesis and Complementation of One Mutation with a Gene Encoding a Fatty Acyl Coenzyme A Reductase", J. Bacteriology 179(9):2969-2975, 1997.
Rowland et al., "CER4 Encodes an Alcohol-Forming Fatty Acyl-Coenzyme A Reductase Involved in Cuticular Wax Production in *Arabidopsis*", Plant Physiology 142:866-877, 2006.
Schirmer et al., "Microbial Biosynthesis of Alkanes", Science 329:559, 2010.
Shockey et al., "*Arabidopsis* Contains Nine Long-Chain Acyl-Coenzyme A Synthetase Genes That Participate in Fatty Acid and Glycerolipid Metabolism", Plant Physiology 129:1710-1722, 2002.
Soupene, "Mammalian Long-Chain Acyl-CoA Synthetases", Experimental Biology and Medicine 233:507-521, 2008.
Steen et al., "Microbial production of fatty-acid-derived fuels and chemicals from plant biomass", Nature 463:559, 2010.
Suzuki et al., "Carbohydrate Metabolism in Mutants of the Cyanobacterium *Synechococcus elongatus* PCC 7942 Defective in Glycogen Synthesis", Applied and Environmental Microbiology 76(10):3153-3159, 2010.
Teerawanichpan, "Fatty Acyl-CoA Reductase and Wax Synthase from *Euglena gracilis* in the Biosynthesis of Medium-Chain Wax Esters", Lipids 45:263-273, 2010.
Wahlen et al., Purification, Characterization, and Potential Bacterial Wax . . . VT8, Applied and Environmental Microbiology 75(9):2758-2764, 2009.
Wang, "Solubilization and purification of aldehyde-generating . . . *Botryococcus braunii*", FEBS Letters 370:15-18, 1995.

(Continued)

*Primary Examiner* — Karen Cochrane Carlson
*Assistant Examiner* — Natalie Moss
(74) *Attorney, Agent, or Firm* — DLA Piper LLP (US)

(57) ABSTRACT

Genes and strains of recombinant microorganisms are provided that are engineered to produce fatty alcohols and fatty alcohol derivatives. The organisms can include one, two, three or more transgenes that direct the biosynthesis of one or more fatty alcohols or derivatives. Methods of producing fatty alcohols using transgenic microorganisms are also provided.

15 Claims, 17 Drawing Sheets

(56) References Cited

OTHER PUBLICATIONS

Doan et al., "Functional expression of five *Arabidopsis* fatty acyl-CoA reductase genes in *Escherichia coli*", *J. Plant Physiology*, vol. 166, No. 8, May 15, 2009.

Kalscheuer et al., "Neutra Lipid Biosynthesis in Engineered *Escherichia coli*: Jojoba Oil-Like Wax Esters and Fatty Acid Butyl Esters", *Applied and Environmental Microbiology*, vol. 72, No. 2, pp. 1373-1379, Feb. 2006.

Lu, A Perspective: Photosynthetic production of fatty acid-based biofuels in genetically engineered cyanobacteria, *Biotechnology Advances* 28:742-746, 2010.

Willis et al., Characterization of a Fatty AcylCoA Reductase from *Marinobacter aquaeolei* VT8: A Bacterial Enzyme Catalyzing the Reduction of Fatty Acyl-CoA to Fatty Alcohol, Biochemistry, vol. 50, No. 48, pp. 10550-10558, Dec. 2011.

Extended European Search Report, EP Patent Application No. 10808723.0-1410/2464722 (PCT/US2010045238), Jun. 10, 2013 (*Synthetic Genomics, Inc.*).

* cited by examiner

2C.

2D.

MICROBIAL PRODUCTION OF FATTY ALCOHOLS

CROSS-REFERENCES TO RELATED APPLICATIONS

This application claims benefit of priority under 35 U.S.C. §119(e) to U.S. provisional patent application 61/233,109 filed Aug. 11, 2009 entitled "Microbial Production of Long-Chain Primary Alcohols", which is incorporated by reference in its entirety.

REFERENCE TO SEQUENCE LISTING

This application contains references to amino acid sequences and/or nucleic acid sequences which have been submitted concurrently herewith as the sequence listing text file "SGI1200-2_ST25.txt", file size 116 KiloBytes (KB), created on Aug. 11, 2010. The aforementioned sequence listing is hereby incorporated by reference in its entirety pursuant to 37 C.F.R. §1.52(e)(5).

TECHNICAL FIELD

This invention describes genes, strains of heterotrophic and photosynthetic microorganisms, and methods to produce fatty acid derivatives, such as fatty alcohols of various chain lengths.

BACKGROUND

Fatty alcohols and their derivatives have numerous commercial applications, including use as surfactants, lubricants, plasticizers, solvents, emulsifiers, emollients, thickeners, flavors, fragrances, and fuels. In addition, fatty alcohols can be dehydrated to alpha-olefins, which have utility in the manufacture of polymers, lubricants, surfactants, plasticizers, and can also be used in fuel formulations. Currently, fatty alcohols are produced via catalytic hydrogenation of fatty acids produced from natural fat and oil sources, primarily coconut, palm, palm kernel, tallow, and lard. These various sources have different fatty acid compositions; of particular importance is the varying acyl chain lengths that are present. As a consequence, the fatty alcohols derived from these fatty acids also have varying chain lengths. The chain length of fatty alcohols greatly impacts the chemical and physical properties of the molecules, and thus different chain lengths are used for different applications. It is typically necessary to fractionate the mixture of fatty alcohols produced from fats and oils via distillation in order to obtain fractions suitable for specific uses; this is an energy intensive process. Fatty alcohols can also be made by chemical hydration of alpha-olefins produced from petrochemical feedstocks.

Fatty alcohols are also made in nature by enzymes that are able to reduce various acyl-CoA molecules to the corresponding primary alcohols. These enzymes are typically referred to as fatty acyl-CoA reductases, but are also referred to as fatty acid reductases. Acyl-CoA reductases have been shown to occur in numerous kinds of organisms, including, but not limited, to bacteria, plants, fungi, algae, mammals, insects, crustaceans, and worms. In nature, the fatty alcohols produced by acyl-CoA reductases are often incorporated into waxes, cuticles, and other structures that serve as a hydrophobic barrier to water penetration and that can also reduce the risk of pathogen infection. In certain organisms, fatty alcohols can also be incorporated into wax esters for use as storage lipids or as glandular secretions. Non-esterified fatty alcohols are not typically found in substantial quantities in living organisms.

Some acyl-CoA reductases, often referred to as an "alcohol-forming fatty acyl-CoA reductase" generate fatty alcohols directly via a two-step reduction as shown in Reaction [1]. Included in this group is the acyl-CoA reductase JjFAR from the plant *Simmondsia chinensis* (jojoba) (Metz et al., Plant Physiol 122: 635-644 (2000)). Also included are certain animal acyl-CoA reductases, including those from mice, humans, and nematodes (Cheng and Russel, J Biol Chem 279: 37789-97 (2004), Moto et al., Proc Natl Acad Sci USA 100: 9156-61 (2003)).

Acyl-CoA+2NAD(P)H→Fatty Alcohol+2NAD(P)+     [1]

Enzyme-based conversions of acyl-CoA molecules to fatty alcohols can also occur via two distinct enzymes: acyl-CoA is first reduced to fatty aldehyde (Reaction [2]) followed by reduction of the fatty aldehyde to the fatty alcohol (Reaction [3]).

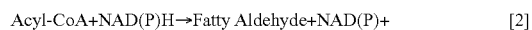

Acyl-CoA+NAD(P)H→Fatty Aldehyde+NAD(P)+     [2]

Fatty Aldehyde+NAD(P)H→Fatty Alcohol+NAD(P)+     [3]

Included in this group of reductase systems are the acyl-CoA reductase and fatty aldehyde reductase of *Acinetobacter* sp. M-1 (Reiser and Somerville, J Bacteriol 179: 2969-75 (1997); Ishige et al., Appl Environ Microbiol. 66:3481-6 (2000); Ishige et al., Appl Environ Microbiol. 68:1192-5 (2002)).

The carboxylic acid reductases ("CAR" enzymes) also function in the pathway from fatty acids to fatty alcohols. These enzymes reduce free fatty acids to aldehydes using. The aldehyde to alcohol reduction requires a fatty aldehyde reductase or alcohol dehydrogenase.

Acyl-ACP, acyl-CoA, or acyl moieties on other acyl donors can also be converted to fatty aldehydes by fatty acid reductase complexes encoded by the LuxCDE genes of luminescent bacteria. These genes encode a reductase, a transferase, and a synthetase that catalyze the reaction:

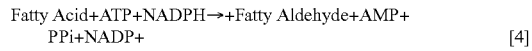

Fatty Acid+ATP+NADPH→+Fatty Aldehyde+AMP+
PPi+NADP+     [4]

It is important to note that acyl-CoA reductases isolated from different sources typically have preferred substrate ranges with respect to acyl chain length, and thus produce fatty alcohols with different chain lengths and thus different properties.

Current technologies for producing fatty alcohols involve inorganic catalyst-mediated reduction of fatty acids to the corresponding primary alcohols. The fatty acids used in this process are derived from natural sources (e.g., plant and animal oils and fats). Dehydration of fatty alcohols to alpha-olefins can also be accomplished by chemical catalysis. The present invention provides methods to create photosynthetic and heterotrophic microorganisms that produce fatty alcohols and alpha-olefins of specific chain lengths directly such that catalytic conversion of purified fatty acids is not necessary. It is anticipated that this biological route will provide product quality and cost advantages.

Published patent applications and patents relating to the subject matter of the invention include WO 2007/136762, "Production of Fatty Acids and Derivatives Thereof"; U.S. Pat. No. 5,254,466, "Site Specific Modification of the Candida Tropicals Genome"; U.S. Pat. No. 5,370,996, "Fatty acyl reductases"; U.S. Pat. No. 5,403,918, "Fatty acyl reductases"; U.S. Pat. No. 5,411,879, "Fatty acyl reductases"; U.S. Pat. No. 5,411,879 "Fatty acyl reductases"; U.S. Pat. No. 5,723, 747 "Wax esters in transformed plants"; U.S. Pat. No. 6,143,538, "Fatty acyl-CoA reductase"; U.S. Pat. No. 7,332,311 "Fatty acyl-CoA: fatty alcohol acyltransferases"; JP Patent 2002223788, "Manufacture of alcohols with plant transformed with acyl reductase gene"; and JP 2004290148, "Pheromone gland-specific fatty-acyl reductase of the silkmoth, *Bombyx mori*".

Published literature having subject matter related to the present application includes the following:

Black, P. N., Zhang, Q., Weimar, J. D., DiRusso, C. C. (1997) Mutational analysis of a fatty acyl-coenzyme A synthetase signature motif identifies seven amino acid residues that modulate fatty acid substrate specificity. J. Biol. Chem. 272: 4896-4903.

Black, P. N., DiRusso, C. C. (2007) Yeast acyl-CoA synthetases at the crossroads of fatty acid metabolism and regulation. Biochim. Biophys. Acta. 1771:286-98.

Cheng, J. B. and Russell, D. W. (2004) Mammalian Wax Biosynthesis: I. Identification of two fatty acyl-coenzyme A reductases with different substrate specificities and tissue distributions. J. Biol. Chem. 279:37789-37797.

Ishige, T., Tani, A., Sakai, Y. and Kato, N. (2000) Long-chain aldehyde dehydrogenase that participates in n-alkane utilization and wax ester synthesis in *Acinetobacter* sp. strain M-1. Appl. Environ. Microbiol. 66: 3481-3486.

Ishige, T., Tani, A., Takabe, K., Kawasaki, K., Sakai, Y. and Kato, N. (2002) Wax ester production from n-alkanes by *Acinetobacter* sp. strain M-1: ultrastructure of cellular inclusions and role of acyl coenzyme A reductase. Appl. Environ. Microbiol. 68:1192-1195.

Kalscheuer, R. Stoveken, T. Luftmann, H. Malkus, U. Reichelt, R. and Steinbuchel A. (2006) Neutral Lipid Biosynthesis in Engineered *Escherichia coli*: Jojoba Oil-Like Wax Esters and Fatty Acid Butyl Esters. Appl. Envir. Microbiol. 72:1373-1379.

Meighen E. A. (1993) Bacterial bioluminescence: organization, regulation, and application of the lux genes. The FASEB Journal 7: 1016-1022.

Metz, J. G., Pollard, M. R., Anderson, L., Hayes, T. R., and Lassner, M. W. (2000) Purification of a jojoba embryo fatty acyl-coenzyme A reductase and expression of its cDNA in high erucic acid rapeseed. Plant Physiol. 122:635-644.

Morgan-Kiss, R. M., Cronan, J. E. (2004) The *Escherichia coli* fadK (ydiD) gene encodes an anaerobically regulated short chain acyl-CoA synthetase. J. Biol. Chem. 279:37324-33.

Moto, K., Yoshiga, T., Yamamoto, M., Takahashi, S., Okano, K., Andoa, T., Nakata, T. and Matsumoto, S. (2003) Pheromone gland-specific fatty-acyl reductase of the silkmoth, *Bombyx mori*. Proc. Natl. Acad. Sci. USA 100:9156-9161.

Ohnishi, A., Hull, J. J., and Matsumoto. S. (2006) Targeted disruption of genes in the *Bombyx mori* sex pheromone biosynthetic pathway. Proc. Natl Acad. Sci USA 103:4398-4403.

Reiser, S., Somerville, C. (1997) Isolation of mutants of *Acinetobacter calcoaceticus* deficient in wax ester synthesis and complementation of one mutation with a gene encoding a fatty acyl coenzyme A reductase. J Bacteriol. 179:2969-75.

Rowland, O. Zheng, H. Hepworth, S. R. Lam, P. Jetter, R. and Kunst, L. (2006) CER4 Encodes an Alcohol-Forming Fatty Acyl-Coenzyme A Reductase Involved in Cuticular Wax Production in *Arabidopsis*. Plant Physiology 142:866-877.

Shockey, J. M., Fulda, M. S., Browse, J. A. (2002) *Arabidopsis* contains nine long-chain acyl-coenzyme a synthetase genes that participate in fatty acid and glycerolipid metabolism. Plant Physiol. 129:1710-22.

Soupene, E., Kuypers, F. A. (2008) Mammalian long-chain acyl-CoA synthetases. Exp. Biol. Med. 233:507-21.

Wahlen, B. D., Oswald, W. S., Seefeldt, L. C., and Barney, B. M. (2009) Purification, Characterization, and Potential Bacterial Wax production Role of an NADPH-Dependent Fatty Aldehyde Reductase from *Marinobacter aquaeolei* VT8. Appl. And Environ. Microbiol. 75: 2758-2764.

SUMMARY OF THE INVENTION

Provided herein are transgenic microorganisms are provided that include exogenous genes for the biosynthesis of fatty acid products such as fatty alcohols and fatty alcohol derivatives and methods of producing fatty acid products, such as fatty alcohols and fatty alcohol derivatives of various chain lengths. The transgenic microorganisms are in some embodiments heterotrophic microorganisms. The transgenic microorganisms in some embodiments are photosynthetic microorganisms.

One aspect of the invention is a recombinant microorganism that includes one or more exogenous genes that encode a fatty acyl-CoA reductase (FAR) or an enzyme of an acyl-CoA reductase complex, a fatty aldehyde reductase, or a carboxylic acid reductase (CAR), in which the microorganism produces at least one fatty alcohol or fatty alcohol derivative, such as an alkene or a wax ester. In particular embodiments, the recombinant microorganism includes at least one exogenous gene encoding an alcohol-forming fatty acyl-CoA reductase. In some embodiments, the alcohol-forming fatty acyl-CoA reductase (alcohol-forming FAR) is a prokaryotic alcohol-forming FAR or is an N-terminally truncated eukaryotic alcohol-forming FAR.

The invention in some embodiments includes a photosynthetic microorganism that includes an exogenous gene encoding a fatty acyl-CoA reductase, an enzyme of an acyl-CoA reductase complex, a fatty aldehyde reductase, or a carboxylic acid reductase (CAR), in which the photosynthetic microorganism produces at least one fatty alcohol or fatty alcohol derivative that can be isolated from the organism or its growth medium. The FAR gene carried by the photosynthetic microorganism can be a gene encoding an alcohol-forming FAR or a gene encoding an aldehyde-generating FAR. The photosynthetic microorganism in some embodiments includes an exogenous gene that encodes an alcohol-forming FAR. The exogenous gene in some embodiments encodes a prokaryotic alcohol-forming FAR and in some embodiments encodes an N-terminally truncated eukaryotic alcohol-forming FAR.

In a further aspect, a transgenic photosynthetic or nonphotosynthetic microorganism is provided, in which the transgenic microorganism includes at least one exogenous gene encoding an alcohol-forming fatty FAR and additionally includes at least one exogenous gene encoding a fatty aldehyde-generating acyl-CoA reductase, a fatty aldehyde-generating acyl-ACP reductase, or a carboxylic acid reductase. In some embodiments, the transgenic microorganism having an exogenous aldehyde-generating acyl-CoA reductase, aldehyde-generating acyl-ACP reductase, or aldehyde-generating carboxylic acid reductase in addition to an exogenous alcohol-forming FAR produces a greater amount of fatty alcohol or fatty alcohol derivative than the same organism having only an alcohol-forming FAR. In some embodiments, the exogenous alcohol-forming FAR is a prokaryotic alcohol-forming FAR or an N-terminally truncated eukaryotic alcohol-forming FAR.

In yet another aspect, the invention provides a transgenic microorganism, in which the transgenic microorganism includes at least one exogenous gene encoding an alcohol-forming FAR and additionally includes at least one exogenous gene encoding a transporter that increases the amount of fatty alcohol or fatty alcohol derivative (e.g., an alkene or wax ester) exported by the cells of the transgenic microorganism. The transporter protein can be, for example, an ATP-binding cassette (ABC) transporter. In some embodiments, the transgenic microorganism having an exogenous gene encoding a transporter protein in addition to an exogenous alcohol-forming FAR produces a greater amount of fatty alcohol or a fatty alcohol derivative than the same organism having an exogenous alcohol-forming FAR but lacking an exogenous gene encoding a transporter protein. In some embodiments of this aspect, the transgenic microorganism is a photosynthetic organism, and in some embodiments the transgenic microorganism is a prokaryotic photosynthetic organism. In some embodiments, the exogenous gene that encodes an alcohol-forming FAR encodes a prokaryotic alcohol-forming FAR or an N-terminally truncated eukaryotic alcohol-forming FAR.

Photosynthetic or nonphotosynthetic transgenic microorganisms transformed with a gene encoding a fatty acyl-CoA reductase can further include at least one additional exogenous gene that encodes an enzyme that participates in the synthesis of a fatty acid product, such as, but not limited to, a fatty alcohol. In some preferred embodiments the additional exogenous gene encodes an acyl-CoA synthetase and/or an acyl-ACP thioesterase. In some embodiments, a transgenic microorganism as provided herein can include an exogenous gene encoding a fatty aldehyde reductase, a fatty alcohol dehydrogenase, a fatty alcohol dehydratase, or a wax synthase. In some embodiments, an additional exogenous gene encodes an acetyl-CoA carboxylase, a malonyl CoA: ACP transacylase, or a beta-ketoacyl-ACP synthase. Transgenic microorganisms that include an exogenous gene encoding a fatty acyl-CoA reductase can also have one or more endogenous genes attenuated. Genes that may be attenuated for production of higher levels of fatty alcohols and derivatives thereof include acyl-CoA dehydrogenase (in some organisms, encoded by the FadE gene) and fatty alcohol oxidase.

A further aspect of the invention is a method of producing a fatty alcohol or a derivative thereof, such as an alkene or a wax ester, that includes culturing a microorganism that includes an exogenous gene encoding a fatty acyl-CoA reductase or one or more exogenous genes encoding a component of a fatty acid reductase complex, and isolating at least one fatty alcohol or derivative thereof from the organism or the growth media. In some embodiments, the microorganism is a photosynthetic microorganism. In some embodiments, the photosynthetic microorganism is grown phototrophically. In some embodiments, the photosynthetic microorganism is grown mixotrophically.

In particular embodiments, the methods include culturing a microorganism that includes at least one exogenous gene encoding an alcohol-forming FAR and at least one additional exogenous gene encoding an aldehyde-generating FAR, a component of an acyl-CoA reductase complex, or a carboxylic acid reductase, and isolating at least one fatty alcohol or derivative thereof from the organism or the growth media.

In other embodiments, the methods include culturing a microorganism that includes at least one exogenous gene encoding an alcohol-forming FAR and at least one additional exogenous gene encoding a transporter that increases the amount of fatty alcohol or fatty alcohol derivative released into the media, and isolating at least one fatty alcohol or fatty alcohol derivative from the organism or the growth media.

The host organism used in the methods can further include one or more genes encoding one or more additional enzymes that participate in the biosynthesis of fatty alcohols, including but not limited to, an acyl-CoA synthetase, an acyl-ACP thioesterase, an acetyl CoA carboxylase, a malonyl CoA: ACP transacylase, a beta-ketoacyl-ACP synthase, or a fatty alcohol dehydrogenase. The host organism can have reduced expression or activity of one or more additional enzymes that reduce the biosynthesis of fatty alcohols, including but not limited to, an acyl-CoA dehydrogenase or a fatty alcohol oxidase. In some embodiments, the microorganism is a photosynthetic microorganism. In some embodiments, the photosynthetic microorganism is grown phototrophically. In some embodiments, the photosynthetic microorganism is grown mixotrophically.

BRIEF DESCRIPTION OF THE DRAWINGS

FIG. 2C is a graph depicting the amount of tetradecanol produced by the strains (micromolar), and FIG. 2D is a graph depicting the amount of fatty acid the strains produced, normalized to OD.

FIG. 3A depicts the growth of various strains provided in Examples 1 and 6. FIG. 3B is a graph depicting the amount of fatty alcohols produced by the strains depicted in FIG. 3A.

FIG. 4A provides a graph illustrating the growth of strains 1a/BL87 (luxC-luxE operon) and 1A/BL88 (luxC-luxE-Maqu 2220) of Example 9. FIG. 4B provides a graph comparing the amount of fatty alcohol made by the strains.

FIG. 5A provides a graph of the growth of Synechocystis strains having the Cc1FatB1 gene (1B) and the luxCE-Maqu2220 expression operon (BL89). FIG. 5B is a graph providing the amount of fatty acid made by isolates of the two strains, normalized to OD. FIG. 5C is a graph comparing the overall amount of fatty acid made by isolates of the two strains, and FIG. 5D is a graph comparing the overall amount of fatty alcohol made by isolates of the two strains.

FIG. 6 depicts fatty acid production and export of fatty alcohols by a microorganism transformed with the Maqu 2220 acyl-CoA reductase gene in combination with a transporter gene.

FIG. 9 depicts production of fatty alcohols by *E. coli* cells expressing a truncated eukaryotic acyl-CoA reductase gene.

DETAILED DESCRIPTION OF THE INVENTION

This invention describes genes and recombinant (also referred to herein as "transgenic" microorganisms capable of producing fatty acid products or derivatives with a specified chain length. The organisms contemplated for use in producing fatty acid products such as fatty alcohols and fatty alcohol derivatives include photosynthetic organisms and heterotrophic organisms, including photosynthetic microorganisms and heterotrophic microorganisms.

Fatty alcohol derivatives include, without limitation, fatty alcohols, wax esters, and alkenes, as well as aldehydes derived from fatty acids. Preferred fatty alcohols and fatty alcohol derivatives are made from $C_8$ to $C_{22}$ fatty acids, more preferably the fatty acid derivatives are fatty alcohols are made from $C_8$ to $C_{22}$ fatty acids, such as $C_8$ to $C_{18}$ fatty alcohols. Preferred fatty alcohols include octanol, decanol, dodecanol, tetradecanol, hexadecanol, and octadecanol.

Figure 1:
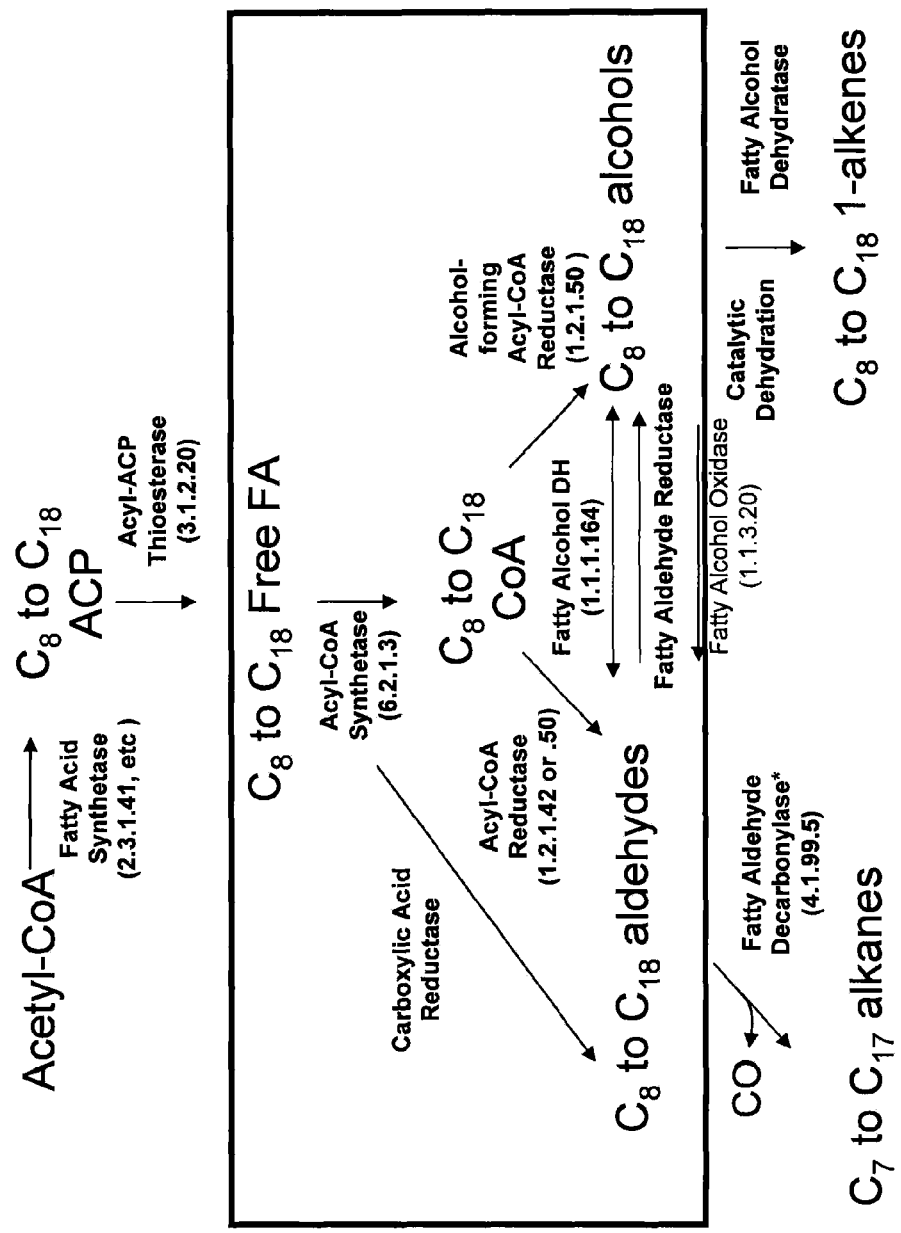
FIG. 1 shows a schematic representation of fatty alcohol metabolic pathways.

A schematic showing various pathways for producing fatty acids and fatty acid derivatives is shown in FIG. 1. In some preferred embodiments of the invention, the fatty acid product or products produced by a transgenic host organism are secreted into the culture medium. Methods of harvesting the fatty acid derivatives from the host cells and/or culture medium and collecting them for processing into fuels and chemicals are provided herein.

This application discloses and refers to genes and proteins by identifiers used in long-established and extensively referenced databases maintained by the National Center for Biotechnology Information (NCBI). Accession numbers are unique identifiers for a sequence record publicly available at the National Center for Biotechnology Information internet site maintained by the United States National Institutes of Health which can be accessed at ncbi.nlm.nih.gov. The "GenInfo Identifier" (GI) sequence identification number is specific to a nucleotide or amino acid sequence. If a sequence changes in any way, a new GI number is assigned. A Sequence Revision History tool is available to track the various GI numbers, version numbers, and update dates for sequences that appeared in a specific GenBank record. Searching and obtaining nucleic acid or gene sequences or protein sequences based on Accession numbers and GI numbers is well known in the arts of cell biology, biochemistry, molecular biology, and molecular genetics.

Elements of the embodiments described herein can be combined to make additional embodiments not specifically described that are also within the scope of the invention.

Headings within the application are solely for the convenience of the reader, and do not limit in any way the scope of the invention or its embodiments.

All publications and patent applications referenced in this specification are herein incorporated by reference to the same extent as if each individual publication or patent application was specifically and individually indicated to be incorporated by reference.

Unless defined otherwise, all technical and scientific terms used herein have the same meaning as commonly understood by one of ordinary skill in the art to which this invention is related. The following terms are defined for purposes of the invention as described herein.

The singular form "a", "an" and "the" include plural referents unless the context clearly dictates otherwise. Thus, for example, reference to "a cell" includes a plurality of cells and reference to "an antibody" includes a plurality of antibodies, etc.

As used herein, the terms "about" or "approximately" when referring to any numerical value are intended to mean a value of plus or minus 10% of the stated value. For example, "about 50 degrees C." (or "approximately 50 degrees C.") encompasses a range of temperatures from 45 degrees C. to 55 degrees C., inclusive. Similarly, "about 100 mM" (or "approximately 100 mM") encompasses a range of concentrations from 90 mM to 110 mM, inclusive. All ranges provided within the application are inclusive of the values of the upper and lower ends of the range.

An "isolated" biomolecule such as an isolated protein or nucleic acid, is a biomolecule removed from the context in which the biomolecule exist in nature. For example, an isolated protein or nucleic acid molecule is removed from the cell or organism with which it is associated in its natural state. An isolated biomolecule can be, in some instances, partially or substantially purified, for example, an isolated nucleic acid molecule can be a nucleic acid sequence that has been excised from the chromosome, genome, or episome that it is integrated into in nature.

A recombinant or "engineered" nucleic acid molecule is a nucleic acid molecule that has been altered through human intervention. As nonlimiting examples, a recombinant nucleic acid molecule: 1) includes conjoined nucleotide sequences that are not conjoined in nature, 2) has been engineered using molecular cloning techniques such that it lacks one or more nucleotides with respect to the naturally occurring nucleic acid molecule sequence, or 3) has been manipulated using molecular cloning techniques such that it has one or more sequence changes or rearrangements with respect to the naturally occurring nucleic acid sequence. As nonlimiting examples, a cDNA is a recombinant DNA molecule, as is any nucleic acid molecule that has been generated by in vitro polymerase reaction(s), or to which linkers have been attached, or that has been integrated into a vector, such as a cloning vector or expression vector.

A "homolog" of a gene or protein refers to its functional equivalent in another species.

A "variant" of a gene or nucleic acid sequence is a sequence having at least 65% identity with the referenced gene or nucleic acid sequence, and can include one or more base deletions, additions, or substitutions with respect to the referenced sequence. Variants also include chimeric genes that include sequences from two or more sources. A variant can be a naturally-occurring variant or the result of a spontaneous or induced mutation. Induced mutations can be created using methods known in the art for mutagenesis of organisms or cells (for example, using gamma or UV irradiation or chemical mutagens such as 5-bromo deoxyuridine, ethyl methane sulfonate (EMS), methyl methane sulfonate (MMS), diethylsulfate (DES), nitrosoguanidine (NTG), ICR compounds, etc., or can be introduced using genetic engineering techniques, such as gene synthesis, in vivo single strand repair techniques, PCR at error- permissive temperature and/or PCR using primers that incorporate base changes.

A "variant" of a peptide or protein is a peptide or protein sequence that varies at one or more amino acid positions with respect to the reference peptide or protein. A variant can be a naturally-occurring variant or can be the result of spontaneous, induced, or genetically engineered mutation(s) to the nucleic acid molecule encoding the variant peptide or protein. A variant peptide can also be a chemically synthesized variant.

"Exogenous" in the context of a gene or protein is a gene or protein that is not derived from the host organism species.

A "transgenic" or "recombinant" or "genetically engineered" organism is an organism that includes at least one exogenous gene. A "recombinant" or "genetically engineered" organism is an organism into which exogenous nucleic acids have been introduced.

A "heterologous" gene or nucleic acid sequence is a gene or sequence from a different source than the host organism it is introduced into, or from a different source than another nucleic acid sequence with which is juxtaposed in a nucleic acid construct. For example, a gene of one species introduced into another species may be referred to as a heterologous gene. A promoter linked to a gene not operably linked to the promoter in its natural state in the organism may be referred to as a heterologous promoter.

A gene that is "codon-optimized" for expression in an organism is a gene whose nucleotide sequence has been altered with respect to the original nucleotide sequence, such that one or more codons of the nucleotide sequence has been changed to a different codon that encodes the same amino acid, in which the new codon is used more frequently in genes of the organism of interest than the original codon. The degeneracy of the genetic code provides that all amino acids except form methionine and tryptophan are encoded by more than one codon. For example, arginine, leucine, and serine are encoded by different six different codons; glycine, alanine, valine, threonine, and proline are encoded by four different codons. Many organisms use certain codons to encode a particular amino acid more frequently than others. Without limiting any aspects of the invention to any particular mechanism, it is believed that some tRNAs for a given amino acid are more prevalent than others within a particular organism, and genes requiring a rare tRNA for translation of the encoded protein may be expressed at a low level due in part to a limiting amount of the rare tRNA. Thus, for adequate levels of expression of an encoded protein, a gene may be "codon-optimized" to change one or more codons to new codons ("preferred codons") that are among those used more frequently in the genes of the host organism (referred to as the "codon preference" of the organism). As used in the context of the invention, a "codon-optimized" gene or nucleic acid molecule of the invention need not have every codon altered to conform to the codon preference of the intended host organism, nor is it required that altered codons of a "codon-optimized" gene or nucleic acid molecule be changed to the most prevalent codon used by the organism of interest. For example, a codon-optimized gene may have one or more codons changed to codons that are used more frequently that the original codon(s), whether or not they are used most frequently in the organism to encode a particular amino acid.

"Photosynthetic organisms" are any prokaryotic or eukaryotic organisms that can perform photosynthesis. Photosynthetic organisms include higher plants (L e., vascular plants), bryophytes, algae, and photosynthetic bacteria. The term "algae" includes cyanobacteria (Cyanophyceae), green algae (Chlorophyceae), yellow-green algae (Xanthophyceae), golden algae (Chrysophyceae), brown algae (Phaeophyceae), red algae (Rhodophyceae), diatoms (Bacillariophyceae), and "pico-plankton" (Prasinophyceae and Eustigmatophyceae). Microalgae are unicellular or colonial algae that can be seen as single organisms only with the aid of a microscope. Microalgae include both eukaryotic and prokaryotic algae (e.g., cyanobacteria). Photosynthetic bacteria include cyanobacteria, green sulfur bacteria, purple sulfur bacteria, purple nonsulfur bacteria, and green nonsulfur bacteria.

A "fatty acid product" includes a fatty acid or a fatty acid derivative, such as a fatty aldehyde, a fatty alcohol, an omega hydroxy fatty acid, a fatty ester (including a wax ester), a triglyceride, a hydrocarbon (e.g., an alkane, alkene, or alkyne), or any other fatty acid derivatives.

A "medium chain length" fatty acid or fatty acid derivative is a fatty acid or fatty acid derivative having an acyl chain length of from 8-14 carbons.

A "long chain length" fatty acid or fatty acid derivative is a fatty acid or fatty acid derivative having an acyl chain length of from 16-18 carbons.

A "very long chain length" fatty acid or fatty acid derivative is a fatty acid or fatty acid derivative having an acyl chain length of greater than 18 carbons.

The degree of amino acid or nucleic acid sequence identity can be determined by various computer programs for aligning the sequences to be compared based on designated program parameters. For example, sequences can be aligned and compared using the local homology algorithm of Smith & Waterman, Adv. Appl. Math. 2:482 (1981), the homology alignment algorithm of Needleman & Wunsch, J. Mol. Biol. 48:443 (1970), or the search for similarity method of Pearson & Lipman, Proc. Nat'l. Acad. Sci. USA 85:2444 (1988), and can be aligned and compared based on visual inspection or can use computer programs for the analysis (for example, GAP, BESTFIT, FASTA, and TFASTA in the Wisconsin Genetics Software Package, Genetics Computer Group, 575 Science Dr., Madison, Wis.

The BLAST algorithm, described in Altschul et al., J. Mol. Biol. 215:403-410 (1990), is publicly available through software provided by the National Center for Biotechnology Information (at the web address www.ncbi.nlm.nih.gov). This algorithm identifies high scoring sequence pairs (HSPS) by identifying short words of length W in the query sequence, which either match or satisfy some positive-valued threshold score T when aligned with a word of the same length in a database sequence. T is referred to as the neighborhood word score threshold (Altschul et al., supra.). Initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below due to the accumulation of one or more negative-scoring residue alignments; or the end of either sequence is reached. For determining the percent identity of an amino acid sequence or nucleic acid sequence, the default parameters of the BLAST programs can be used. For analysis of amino acid sequences, the BLASTP defaults are: word length (W), 3; expectation (E), 10; and the BLOSUM62 scoring matrix. For analysis of nucleic acid sequences, the BLASTN program defaults are word length (W), 11; expectation (E), 10; M=5; N=−4; and a comparison of both strands. The TBLASTN program (using a protein sequence to query nucleotide sequence databases) uses as defaults a word length (W) of 3, an expectation (E) of 10, and a BLOSUM 62 scoring matrix. (see Henikoff & Henikoff, Proc. Natl. Acad. Sci. USA 89:10915 (1989)).

In addition to calculating percent sequence identity, the BLAST algorithm also performs a statistical analysis of the similarity between two sequences (see, e.g., Karlin & Altschul, Proc. Nat'l. Acad. Sci. USA 90:5873-5787 (1993)). The smallest sum probability (P(N)), provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, preferably less than about 0.01, and more preferably less than about 0.001.

As provided herein, a fatty acyl-CoA reductase or "FAR" is an enzyme that reduces acyl-Co to an aldehyde or alcohol. Such enzymes typically use NADH or NADPH as an electron donor. For convenience, the term "FAR" herein encompasses fatty acyl reductases that convert acyl substrates that include but are not limited to acyl-ACP and acyl-CoA.

As used herein, "alcohol-forming fatty acyl-CoA reductase" or "alcohol-forming FAR" is a fatty acyl-CoA reductase that produces alcohol as a product of the reduction reaction.

As used herein a "fatty aldehyde forming fatty acyl-CoA reductase" or "fatty aldehyde forming FAR" is an enzyme that reduces acyl-ACP or acyl-CoA to an aldehyde.

As used herein a "carboxylic acid reductase" or "CAR" is an enzyme that reduces a free fatty acid to an aldehyde.

Host Organisms

The disclosed invention contemplates the use of photosynthetic and heterotrophic organisms that can be engineered to produce one or more fatty alcohols or fatty alcohol derivatives, including, without limitation, fatty alcohols, fatty aldehydes, wax esters, alkanes, and alkenes. The organisms can be eukaryotic or prokaryotic. In some embodiments, a host strain used for producing a fatty alcohol or fatty alcohol derivative is a prokaryotic organism.

Any photosynthetic microorganism, including phytoplankton, eukaryotic or prokaryotic algae, and bacteria, can be used as a host organism with the disclosed invention. Preferred host organisms include eukaryotic microalgae and cyanobacteria (blue-green algae). Representative algae include green algae (chlorophytes), red algae, diatoms, prasinophytes, glaucophytes, chlorarachniophytes, euglenophytes, chromophytes, and dinoflagellates. A number of cyanobacterial species are known and have been manipulated using molecular biological techniques, including the unicellular cyanobacteria *Synechocystis* sp. PCC6803 and *Synechococcus elongatus* PCC7942, whose genomes have been completely sequenced.

In some embodiments a photosynthetic organism transformed with a nucleic acid molecule that encodes an enzyme that participates in fatty alcohol synthesis is a plant, such as but not limited to a higher plant, or an alga. Higher plants considered for use in the invention include, without limitation, *Arabidopsis thaliana, Arachis hypogaea, Avena sativa, Brassica* species (e.g., *Brassica napus, Brassica campestris, Brassica juncea*), *Camelina sativa, Carthamus tinctorius, Cocos nucifera, Crambe abyssinica, Cuphea* species, *Elaeis* species (e.g., *Elaeis guineensis, Elaeis oleifera*), *Gossypium hirsutum, Glycine max, Helianthus annuulus, Jatropha* species, *Cucurbita pepo, Oryza satvia, Sesamum indicum, Simmondsia chinensis, Theobroma cacao, Ricinus communis*, and *Zea mays*.

Algae that can be transformed with one or more nucleic acid molecules encoding enzymes used in the biosynthesis of a fatty alcohol or derivative can be any algae, and can include microalgae, such as but not limited to, *Achnanthes, Amphiprora, Amphora, Ankistrodesmus, Asteromonas, Boekelovia, Borodinella, Botryococcus, Bracteococcus, Chaetoceros, Carteria, Chlamydomonas, Chlorococcum, Chlorogonium, Chlorella, Chroomonas, Chrysosphaera, Cricosphaera, Crypthecodinium, Cryptomonas, Cyclotella, Dunaliella, Ellipsoidon, Emiliania, Eremosphaera, Ernodesmius, Euglena, Franceia, Fragilaria, Gloeothamnion, Haematococcus, Halocafeteria, Hymenomonas, Isochrysis, Lepocinclis, Micractinium, Monoraphidium, Nannochloris, Nannochloropsis, Navicula, Neochloris, Nephrochloris, Nephroselmis, Nitzschia, Ochromonas, Oedogonium, Oocystis, Ostreococcus, Pavlova, Parachlorella, Pascheria, Phaeodactylum, Phagus, Platymonas, Pleurochrysis, Pleurococcus, Prototheca, Pseudochlorella, Pyramimonas, Pyrobotrys, Scenedesmus, Schizochytrium, Skeletonema, Spyrogyra, Stichococcus, Tetraselmis, Thalassiosira, Viridiella*, or *Volvox* species.

In some embodiments, photosynthetic bacteria, including for example, green sulfur bacteria, purple sulfur bacteria, green nonsulfur bacteria, purple nonsulfur bacteria, or cyanobacteria are used transformed with one or more genes for producing a fatty alcohol or derivative of a fatty alcohol. For example, photosynthetic bacteria such as bacteria of a *Rhodopseudomonas, Rhodobacter, Rhodococcus, Rhodospirillium*, or *Rhodomicrobium* species can be used as host organisms.

Cyanobacterial species that can be used for production of fatty acid products include, without limitation, *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dadylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema*, or *Xenococcus* species.

A variety of heterotrophic organisms are also contemplated for use with the described invention. Specifically contemplated hosts include, but are not limited to, heterotrophic microorganisms, such as, but not limited to, *E. coli, Pseudomonas putida, Schizosaccharomyces pombe, Saccharomyces cerevisiae*, and *Candida tropicalis*. Additional heterotrophic species that can be transformed with genes encoding enzymes involved in the synthesis of fatty acid products include bacterial species such as *Acetobacter, Acinetobacter, Arthrobacter, Bacillus, Brevibacterium, Chromatium, Chlorobium, Clostridium, Corynebacterium, Deinococcus, Delfiia, Desulfovibrio, Enterococcus, Escherichia, Kineococcus, Klebsiella, Lactobacillus, Lactococcus, Micrococcus, Mycobacterium, Jeotgalicoccus, Paenibacillus, Propi-*

*onibacter, Pseudomonas, Salmonella, Serratia, Stenotrophomonas, Streptococcus, Vibrio,* or *Zymomonas* species.

Metabolic Pathways

The disclosed invention contemplates modifying enzymatic pathways in host organisms to produce fatty acid derivatives, such as fatty alcohols and products derived from fatty alcohols. One or more aspects of an organism's fatty acid metabolism may be modified. FIG. 1 is a schematic diagram providing some metabolic pathways for fatty acid products, including fatty acids, fatty aldehydes, fatty alcohols, alkanes, and alkenes. Not depicted in FIG. 1, but also considered products of interest, are wax esters, which are produced by the action of wax synthases and are derived from fatty acids and fatty alcohols. Modification of one or more pathways, such as but not limited to the pathways depicted in FIG. 1 by genetic engineering of an organism can increase the amount of a particular type of fatty acid product and/or increase the amount of a particular fatty acid product of a specific chain length produced by an organism. The specific modifications made to the host will depend on the nature of the host organism and the organism's endogenous enzymatic pathways. In some embodiments, the host organism is engineered to contain one or more exogenous genes that encode enzymes that participate in the synthesis of a fatty alcohol. In some embodiments, particular endogenous components of a host organism's fatty acid metabolism may be modified via overexpression of one or more genes and/or downregulation or inactivation of one or more genes to maximize the production of one or more fatty alcohols or products derived therefrom.

In all embodiments of the invention, it is contemplated that recombinant host organisms for the production of fatty acid products can be engineered to include genes encoding naturally-occurring or isolated enzymes, and also variants of naturally-occurring or isolated enzymes, including but not limited to variants of any of the enzymes referenced herein or enzymes encoded by genes reference herein that participate in the synthesis of a fatty alcohol. For example, genes encoding enzymes such as but not limited to acyl-CoA reductases, fatty acid reductases, acyl-ACP thioesterases, acyl-CoA synthetases, β-ketoacyl-ACP synthases, alcohol dehydrogenases, or fatty aldehyde reductases used in the invention can encode enzymes that are at least 60% identical to the amino acid sequences of a naturally-occurring or isolated enzyme, in which the variant enzyme has at least one activity of the naturally-occurring or isolated enzyme. For example, a nucleic acid encoding a variant of an enzyme that participates in the synthesis of a fatty acid product in some embodiments encodes a variant that is at least 65% identical, at least 70% identical, at least 75% identical, at least 80% identical, at least 85% identical, at least 90% identical, at least 95% identical, at least 97% identical, at least 98% identical, at least 99% identical, or at least 99.5% identical to the amino acid sequence of a naturally-occurring or isolated enzyme from which its sequence is derived, and has at least one activity of the naturally-occurring or isolated enzyme from which it is derived. In some embodiments, a variant gene harbored by the host organism encodes an enzyme that has at least the level of activity as the enzyme from which its sequence is derived, and in some embodiments a variant gene has the same or increased specificity toward a substrate having a particular acyl chain length as compared with the naturally-occurring or isolated enzyme from which it is derived.

In some embodiments, a microorganism, such as a heterotrophic or photosynthetic microorganism (e.g., a prokaryotic or eukaryotic microalga) is genetically engineered to direct or enhance production of one or more fatty alcohols by the microorganism. The production of fatty alcohols from acyl-CoA molecules is catalyzed by acyl-CoA reductases referred to herein as "alcohol-forming FARs". Other acyl-CoA reductases catalyze the production of aldehydes, which in turn can be converted to fatty alcohols by a fatty alcohol dehydrogenase or a fatty aldehyde reductase. A microorganism can be transformed with an exogenous gene encoding an acyl-CoA reductase of either the aldehyde-producing or alcohol-producing type, or with a fatty aldehyde reductase component of an two-enzyme acyl CoA reductase system, to enhance production of one or more fatty alcohols by the microorganism.

In the alternative, a microorganism, such as a heterotrophic or photosynthetic microorganism (e.g., a prokaryotic or eukaryotic microalga) is engineered to express a fatty acid reductase complex, such as a fatty acid reductase complex encoded by the Lux genes of luminescent bacteria. For example, the Lux C, D, and E genes encode a reductase, an acyl transferase, and a synthetase that together are able to convert free fatty acids to fatty aldehydes. The fatty aldehydes produced by these enzymes can be converted to fatty alcohols by endogenous enzymes or enzymes encoded by an exogenous nucleic acid molecule. Such enzymes can be fatty alcohol dehydrogenases or fatty aldehyde reductases.

In embodiments in which, for example, a heterologous gene that encodes an enzyme that reduces an acyl-CoA molecule to the corresponding fatty aldehyde is expressed in a photosynthetic or heterotrophic microorganism, an endogenous fatty alcohol dehydrogenase or fatty aldehyde reductase, or a fatty alcohol dehydrogenase or fatty aldehyde reductase that is also encoded by a transgene introduced into the host organism can convert the fatty aldehyde to a fatty alcohol. For example, a gene that encodes the *Acinetobacter* acyl-CoA reductase (GenPept Accession Number BAB85476) can be introduced along with a long-chain aldehyde dehydrogenase (e.g. GenPept Accession Number BAB 11888).

Genes or portions of genes that are listed in GenBank and other genetic databases and that are predicted to encode proteins that are homologous to known acyl-CoA reductases that produce fatty aldehydes, or genes encoding variants thereof, can be introduced into various microorganisms in order to test for the production of specific fatty aldehydes or fatty alcohols. The genes can be from any species, including bacterial, fungal, plant, algal, and animal species.

An acyl-CoA reductase for expression in a host organism in some preferred embodiments is selected so that its acyl-CoA substrate specificity closely matches the range of fatty alcohols (or other desired fatty acid product) to be produced in the host organism. For example, if tetradecanol is the desired fatty alcohol product, it is preferable to introduce a gene that encodes an acyl-CoA reductase that can preferentially use tetradecanoyl-CoA as a substrate. Likewise, if octanol is the desired fatty alcohol product, it is preferable to introduce a gene that encodes an acyl-CoA reductase that can preferentially use octanoyl-CoA as a substrate. As nonlimiting examples, genes that encode the following acyl-CoA reductases (or portions thereof) from various plant or animal sources, or genes encoding variants thereof, can be introduced into a host organism: GenPept Accession Numbers Q8WVX9, Q922J9, Q96K12, Q7TNT2, Q08891, Q5ZM72, Q66H50, Q5R834, Q7ZXF5, Q0P5J1, Q08891, Q8H1Z0, Q0WRB0, Q1PEI6, Q2V3Q9, Q5QIV3, Q652L3, Q69LA9, Q6YZQ7, Q6ZJ06, Q7X988, Q8L4C3, Q8L4M0, Q8L4V2, Q9FMQ9, Q9LXN1, Q9LXN2, Q9LXN3, and Q9XGY7.

Genes or portions of genes that are listed in GenBank and other genetic databases and that are predicted to encode proteins that are homologous to known acyl-CoA reductases that produce fatty aldehydes, referred to herein as "aldehyde-generating fatty acyl-CoA reductases", can be introduced into various microorganisms in order to test for the production of specific fatty aldehydes or fatty alcohols produced therefrom. Examples of fatty aldehyde-generating acyl-CoA reductases include the Acr1 gene of *Acinetobacter baylyi* (gb|U77680.1|, GI:1684885), the AcrM-1 gene of *Acinetobacter* sp. M-1 (dbj|AB070446.1|, GI:18857900), and the luxC and luxE genes of various photoluminescent bacteria.

Additional genes that may encode aldehyde-generating fatty acyl-CoA reductases or alcohol-forming fatty acyl-CoA reductases, or aldehyde reductases that generate fatty alcohols, that can be introduced into a host may include, but are not limited to, the following: GenBank Accession Numbers; gb|CP000521.1|, GI:126385999, *Acinetobacter baumannii* ATCC 17978 gene for acyl-CoA reductase (protein id ABO13615.2); gb|CP000863.1|, GI:183207914, *Acinetobacter baumannii* ACICU; emb|CU459141.1|, GI:169147133, *Acinetobacter baumannii* str. AYE; emb|CU468230.2|, GI:169150821 *Acinetobacter baumannii* str. SDF="fatty acyl-CoA reductase (hexadecanal dehydrogenase,acylating)", protein id CAO99653.1; emb|CR543861.1|, *Acinetobacter* sp. ADP1="fatty acyl-CoA reductase (hexadecanal dehydrogenase,acylating)", protein id number CAG70047.1";, gb|CP000323.1|, GI:92392509, *Psychrobacter cryohalolentis*; gb|CP000713.1|, GI:148570901, *Psychrobacter* sp. PRwf-1="probable fatty acyl-CoA reductase protein"; gb|CP000082.1|, GI:71037566, *Psychrobacter arcticus* 273-4, probable fatty acyl-CoA reductase protein (protein id AAZ19149.1); gb|CP000155.1|, GI:83630956, *Hahella chejuensis* KCTC 2396; gb|CP000514.1|, GI:120322793, *Marinobacter aquaeolei* VT8; emb|CR378670.1|, GI:46913734, *Photobacterium profundum* SS9; gb|CP000509.1|, GI:119534933, *Nocardioides* sp. JS614 putative fatty acyl coA reductase (protein id ABL81508.1; gb|CP000316.1|, GI:91695138 *Polaromonas* sp. JS666; gb|CP000555.1|, GI:124257968, *Methylibium petroleiphilum* PM1; gb|CP000529.1|, GI:120591888, *Polaromonas naphthalenivorans* CJ2; gb|CP000267.1|, GI:89343559, *Rhodoferax ferrireducens* T118; gb|CP000431.1|, GI:110816552, *Rhodococcus jostii* RHA1; gb|CP000644.1|, GI:142849896, *Aeromonas salmonicida* subsp. *salmonicida* A449; gb|CP000479.1|, GI:118163506, Mycobacterium avium 104; gb|CP000462.1|, GI:117558854, *Aeromonas hydrophila* subsp. *hydrophila* ATCC 7966,="putative acyl-CoA reductase LuxC", ABK39633.1; gb|CP000854.1|, GI:183173361, *Mycobacterium marinum* M="fatty acyl-CoA reductase", ACC40815.1; gb|AE016958.1|, GI:41400296, *Mycobacterium avium* subsp. *paratuberculosis* str. k10 ; and emb|CR378669.1|, GI:46913430, *Photobacterium profundum* SS9, as well as genes encoding variants of the encoded reductases. The enzymes encoded by these genes can be tested to determine their substrates and products using assays know in the art.

In addition, genes or portions of genes that are listed in GenBank and other genetic databases and that are predicted to encode proteins that are homologous to known acyl-CoA reductases, as well as genes encoding variants of the encoded acyl-CoA reductases, can be introduced into various microorganisms in order to test for the production of specific fatty alcohols. Such genes include, but are not limited to, the following: GenBank Accession Numbers dbj|AB173492.1|; dbj|AK001324.1|; dbj|AK001927.1|; dbj|AK005531.1|; dbj|AK011187.1|; dbj|AK014405.1|; dbj|AK014486.1|; dbj|AK026381.1|; dbj|AK027756.1|; dbj|AK030067.1|; dbj|AK033674.1|; dbj|AK038584.1|; dbj|AK043388.1|; dbj|AK043589.1|; dbj|AK061142.1|; dbj|AK065894.1|; dbj|AK069659.1|; dbj|AK071956.1|; dbj|AK072574.1|; dbj|AK121254.1|; dbj|AK129857.1|; dbj|AK137298.1|; dbj|AK161201.1|; dbj|AK227396.1|; dbj|AK228404.1|; dbj|AK241568.1|; dbj|AK242888.1|; dbj|AK249037.1|; dbj|AK250407.1|; dbj|AK314670.1|; dbj|AK315527.1|; emb|AJ272073.1|TMA272073; emb|AJ459249.1|TAE459249; emb|AJ459251.1|TAE459251; emb|AJ459253.1|TAE459253; emb|AL136843.1|HSM801811; emb|AL161584.2|ATCHRIV80; emb|AL354915.5|; emb|BX824038.1|CNS0A5JE; emb|BX827659.1|CNS0A2HW; emb|CR607516.1|; emb|CR611981.1|; emb|CR859126.1|; emb|CR859921.1|; emb|CR936619.11; emb|CT832651.1|; emb|CT835935.1|; emb|CU692520.1|; emb|CU692521.1|; emb|X73652.1|ATMS2MR; emb|X99922.1|BNMS2PROT; emb|X99923.1|ATMS2LIPR; gb|AC004287.1|AC004287; gb|AC084584.1|CBRG41B17; gb|AC091501.1|AC091501; gb|AE013599.4|; gb|AF149917.1|AF149917; gb|AF149918.1|AF149918; gb|AY035042.1|; gb|AY051075.1|; gb|AY051805.1|; gb|AY051874.1|; gb|AY057657.1|; gb|AY058365.1|; gb|AY060302.1|; gb|AY069232.1|; gb|AY070065.1|; gb|AY102650.1|; gb|AY119078.1|; gb|AY119109.1|; gb|AY358784.1|; gb|AY423606.1|; gb|AY461413.1|; gb|BC007178.1|; gb|BC017377.2|; gb|BC055759.1|; gb|BT010010.1|; gb|BT022496.1|; gb|BT022632.1|; gb|BT024297.1|; gb|BT032826.1|; gb|BT033118.1|; gb|DQ446732.1|; gb|DQ653127.1|; gb|EF084237.1|; gb|EF093533.1|; gb|EU363493.1|; ref|NM_001011933.1|; ref|NM_001031179.1|; ref|NM_001032011.1|; ref|NM_001032012.1|; ref|NM_001035732.1|; ref|NM_001055618.1|; ref|NM_001059076.1|; ref|NM_001069023.1|; ref|NM_001070497.1|; ref|NM_001076022.1|; ref|NM_001083089.1|; ref|NM_001086122.1|; ref|NM_001090221.1|; ref|NM_001097387.1|; ref|NM_001099032,1|; ref|NM_018099.3|; ref|NM_026143.2|; ref|NM_027379.2|; ref|NM_032228.4|; ref|NM_076104.3|; ref|NM_112032.2|; ref|NM_114322.4|; ref|NM_114323.3|; ref|NM_114324.2|; ref|NM_119537.3|; ref|NM_122147.1|; ref|NM_122155.3|; ref|NM_132048.1|; ref|NM_135397.2|; ref|NM_136691.2|; ref|NM_137296.2|; ref|NM_137299.1|; ref|NM_138136.2|; ref|NM_141929.2|; ref|NM_142309.1|; ref|NM_142310.1|; ref|NM_142311.2|; ref|NM_142940.2|; ref|NM_143395.1|; ref|NM_165720.2|; ref|NM_166697.1|; ref|NM_166698.1|; ref|NM_166699.1|; ref|NM_169464.2|; ref|NM_176550.1|; ref|NM_178797.3|; ref|NM_213508.1|; ref|XM_001074438.1|; ref|XM_001093564.1|; ref|XM_001093685.1|; ref|XM_001093916.1|; ref|CM001105259.1|; ref|XM_001105324.1|; ref|XM_001105402.1|; ref|XM_001105472.1|; ref|XM_001141205.1|; ref|XM_001141288.1|; ref|XM_001141374.1|; ref|XM_001141453.1|; ref|XM_001141535.1|; ref|XM_001141623.1|; ref|XM_001171869.1|; ref|XM_001171884.1|; ref|XM_001171908.1|; ref|XM_001182012.1|; ref|XM_001354820.1|; ref|XM_001357967.1|; ref|XM_001357968.1|; ref|XM_001357990.1|; ref|XM_001358636.1|; ref|XM_001358749.1|; ref|XM_001360222.1|; ref|XM_

001360223.1|; reflXM__001361199.1|; reflXM__001362012.1|; reflXM__001363685.1|; reflXM__001367749.1|; reflXM__001499230.1|; reflXM__001501346.1|; reflXM__001507720.1|; reflXM__001600200.1|; reflXM__001600227.1|; reflXM__001600259.1|; reflXM__001601118.1|; reflXM__001601799.1|; reflXM__001601892.1|; reflXM__001601920.1|; reflXM__001602592.1|; reflXM__001602684.1|; reflXM__001602712.1|; reflXM__001602807.1|; reflXM__001605033.1|; reflXM__001605322.1|; reflXM__001607457.1|; reflXM__001630943.1|; reflXM__001648359.1|; reflXM__001650641.1|; reflXM__001650642.1|; reflXM__001652611.1|; reflXM__001652617.1|; reflXM__001652618.1|; reflXM__001655399.1|; reflXM__001658000.1|; reflXM__001658167.1|; reflXM__001658169.1|; reflXM__001658904.1|; reflXM__001663784.1|; reflXM__001663943.1|; reflXM__001675789.1|; reflXM__001688716.1|; reflXM__001688718.1|; reflXM__001758066.1|; reflXM__001771255.1|; reflXM__001811257.1|; reflXM__001812412.1|; reflXM__001812497.1|; reflXM__001845925.1|; reflXM__001845926.1|; reflXM__001845927.1|; reflXM__001848728.1|; reflXM__001849237.1|; reflXM__001861291.1|; reflXM__001861292.1|; reflXM__001868420.1|; reflXM__001898871.1|; reflXM__001944480.1|; reflXM__001944958.1|; reflXM__001945430.1|; reflXM__001946115.1|; reflXM__001946329.1|; reflXM__001946689.1|; reflXM__001946838.1|; reflXM__001947215.1|; reflXM__001948283.1|; reflXM__001948786.1|; reflXM__001949336.1|; reflXM__001949648.1|; reflXM__001950209.1|; reflXM__001950652.1|; reflXM__307899.4|; reflXM__313370.4|; reflXM315515.4|; reflXM__318025.4|; retlXM__318028.4|; reflXM__318748.4|; reflXM__320774.4|; reflXM__321801.4|; reflXM__395379.3|; reflXM__395449.3|; reflXM__396437.3|; reflXM__396740.3|; reflXM__417235.2|; reflXM__508294.2|; reflXM__528765.2|; reflXM__534066.2|; reflXM__534853.1|; reflXM__556664.3|; reflXM__575726.2|; reflXM__623663.2|; reflXM__624490.2|; reflXM__784843.2|; reflXM__859505.1|; reflXM__961812.1|; reflXM__962659.1|; reflXM__962664.2|; reflXM__962939.1|; reflXM__963017.1|; reflXM__963283.2|; reflXM__963437.1|; reflXM__963662.1|; reflXM__963701.1|; reflXM__964128.2|; reflXM__965703.1|; reflXM__965823.2|; reflXM__966135.1|; reflXM__966262.1|; reflXM__966441.2|; reflXM__966794.2|; reflXM__967621.2|; reflXM__968338.2|; reflXM__968374.2|; reflXM__968697.1|; reflXM__969574.1|; reflXR__007043.1|; reflXR__009413.1|; and reflXR__009661.1|

In some embodiments, one or more genes encoding one or more proteins of the fatty acid reductase complex of luminescent bacteria having are used to engineer microorganisms for the production of fatty alcohols or fatty aldehydes. The Lux CDE genes encode a reductase (encoded by lux C), an acyl transferase (encoded by lux D), and a synthetase (encoded by lux E). Together these three proteins form a reductase complex that is able to reduce a fatty acid to a fatty aldehyde (reviewed in Meighen, E. A., Microbiological Reviews 55: 123-42 (1991) and Meighen, E. A., FASEB J 7: 1016-22 (1993)). LuxCDE genes encoding proteins of a fatty acid reductase complex of a luminescent bacterial species that can be introduced into a host organism can be from an *Altermonas*, *Photobacterium*, *Shewanella*, *Vibrio*, or *Xenorhabdus* species, such as, for example, *Altermonas haneda*, *Photobacterium phosphoreum*, *Photobacterium leiognathi*, *Shewanella hanedai*, *Vibrio cholerae*, *Vibrio fisheri*, *Vibrio harveyi*, *Vibrio splendidus*, or *Xenorhabdus luminescens*. Genes encoding Lux C, Lux, D, and/or Lux E can be introduced independently of one another into a host strain, or in any combination.

Nonlimiting examples of carboxylic acid reductases that can be used in the invention include the Nocardia CAR gene (Accession AY495697; GI:40796034) and homologs thereof, some of which are disclosed in US2020/0105963, incorporated by reference herein.

Transporter proteins, such as ATP-binding cassette (ABC) proteins can be introduced into a host that includes an exogenous fatty acyl-CoA reductase gene, fatty aldehyde reductase gene, or carboxylic acid reductase gene. For example, ABC transporters of *Arabidopsis* such as those encoded by the CER5 gene, the WBC11 gene, AtMRPS, AmiS2, and AtPGP1 can be introduced into a host cell. In some embodiments, fatty acid transporter (FATP) genes from species including *Saccharomyces*, *Drosophila*, *Mycobacterials*, or mammalian species can be introduced into a host cell. In some embodiments, a transporter protein increases the amount of a fatty alcohol or fatty alcohol derivative released into the growth medium of a microorganism. Expression of a transporter protein can in some embodiments also increase production of a fatty alcohol or fatty alcohol derivative by a host strain.

In some embodiments, a nucleic acid molecule encoding an acyl-CoA synthetase can be introduced into the host organism that also includes an acyl-CoA reductase to increase fatty alcohol production. Examples of prokaryotic acyl-CoA synthetases include the enzymes encoded by FadD and FadK of *E. coli*, and their homologs in other species. Introduction of a particular acyl-CoA synthetase can increase the amount of a fatty alcohol of a particular chain length being synthesized. Many genes encoding putative acyl-CoA synthetase enzymes have been reported, including the following GenPept Accession Numbers: Q86V21; Q2KHW5; Q96GR2; Q4R4P9; Q99PU5; Q924N5; Q5ZKR7; Q5FVE4; Q2XU92; A1L1K7; Q7ZYC4; Q08AH3; Q68CK6; Q9NUB1; Q99NB1; Q9NR19; Q9QXG4; Q554Z5; Q17QJ1; Q0P4F7; Q96CM8; Q4R4Z9; Q8VCW8; Q5R9G9; Q499N5; Q58DN7; Q4G176; Q2URE1; Q6GLK6; Q5RG49; Q9VLL0; Q4L235; Q80WC9; Q9JID6; P33121; P41216; P18163; O95573; Q9CZW4; Q5R668; Q63151; O60488; Q9QUJ7; O35547; Q9ULC5; Q8JZR0; O88813; Q9UKU0; Q91WC3; P33124; Q9BEA2; Q08AH1; Q91VAO; Q8K0L3; O70490; Q53FZ2; Q3UNX5; Q5REV5; Q6SKG1; Q80W40; Q7TN78; Q6NUN0; A7MB45; Q9H6R3; Q14DH7; Q5REB8; Q00594; Q10776; P63524; P54200; P63523; Q50586; Q10976; Q02278; P38135; Q55DR6; O60135; P30624; Q9P7D7; P39518; P39002; P47912; P94547; Q8XDR6; P69452; P69451; P46450; P63522; P63521; Q8ZES9; P44446; Q60714; O14975; O35488; P97524; Q5K4L6; O88561; Q9I VE0; Q9Y2P5; Q4LDG0; Q9ES38; Q9Y2P4; Q9KWK5; Q5HIA1; Q99W34; Q7A769; Q6GJ94; Q6GBR2; Q7A1Q0; Q5HRH4; Q8CQ67; Q4L3Q0; A0ADS3; A0FCT1; A0HM09; A0KEL7; A0KJH3; A0KN59; A0NHZ6; A0NNN0; A0NVW8; A0NZH2; A0PL65; A0QD46; A0QUK6; A0QYK2; A0R2E8; A0RTL2; A0RTZ5; A0Y217; A0Y3A0; A0YB53; A1A810; A1ABN8; A1AEB5; A1APD5; A1C0L8; A1C6H9; A1CCK6; A1CSK5; A1DG91; A1DH51; A1EPR3; A1FAW8; A1RRT1; A2AQN4; A2AQN5; A2AQN6; A2BJ63; A2QCE9; A2QPE7; A2QUT7; A2RIY1; A2SEI4; A2SGN9; A2VQP8; A2VU01; A2VVZ5; A2W1N3; A2W5M3; A2WGX5; A3DLQ0; A3DNX4; A3ERC4;

A3HT18; A3J6L6; A3JAV5; A3JC01; A3JCC0; A3JMW8; A3JNG4; A3JZE1; A3JZV0; A3JZV1; A3KB66; A3LXD8; A3LZE8; A3M105; A3M1R5; A3M5P8; A3RE46; A3RE47; A3RE48; A3RE49; A3SRC1; A3THW2; A3T1K1; A3TR14; A3TZN3; A3URV4; A3V0U7; A3VID4; A3V8E9; A3VZI5; A3W018; A3WJB5; A3WK79; A3WNW5; A3X726; A3Y0T3; A3Y676; A3YFW8; A3Z272; A4B0S6; A4BB42; A4BCL0; A4BIL9; A4BJQ3; A4C465; A4C9D2; A4EF25; A4EF26; A4ET60; A4FCG4; A4FDA6; A4FDK5; A4FEL6; A4FF59; A4FGY4; A4FJG6; A4G1R3; A4GIK7; A4H3J5; A4H731; A4HRH3; A4HRH4; A4HRT4; A4HVG5; A4IRS7; A4KS78: A4SJZ5; A4SMQ8; A4STE6; A4YLS0; A4YLS5; A4YLX1; A4YM86; A4YQ15; A4YZI2; A4Z1Z5; A4Z214; A4Z2T7; A5CFR5; A5CM08; A5CM59; A5CSC4; A5CSZ9; A5D034; A5D1F4; A5D252; A5D530; A5EEM8; A5ELP8; A5ES57; A5ES62; A5FAI7; A5G5K0; A5GJ91; A5GUZ0; A5I515; A5KBX3; A5KZ60; A5L181; A5P9H5; A5P9Q3; A5UN98; A5W4Q6; A5WV16; A5ZYV9; A6A7K1; A6A7Y2; A6AJE4; A6AMZ8; A6ARQ1; A6AXX4; A6AXX5; A6AZ50; A6AZM0; A6B385; A6B7R5; A6BA48; A6D7G0; A6DTH2; A6EG18; A6EP07; A6EUH1; A6F6D2; A6FCC2; A6GF11; A6MIJ1; A6PW74; A6QDL0; A6SS77; A6TCJ6; A6V3J8; A6YQV5; A6ZMW0;A6ZPF1; A6ZQW3; A6ZVQ9; A7AMN1; A7APW0; A7BRD8; A7FLN8; A7FWL5; A7GGH1; A7KAU1; A7W164; A7YPU0; A7YT12; A8B3P9; A8B4I3; A8FFM4; A8IP90; A8K051; A8K2Q7; A8K9T3; A8PNF2; A8R0K4; A8TJZ4; A8TJZ5; A8TX99; A8U4Y2; A8UP49; A8VR95; A8VX79; A9ASF1; A9CB21; A9CUN4; A9D0T2; A9ELY5; A9F9L2; A9FLR5; A9FQG4; A9G6G3; A9GYD4; A9GYQ6; A9H292; A9HGC2; A9HVR7; A9HXE6; A9I514; A9IWW0; A9IXK0; A9IZA7; A9IZA8; A9J9G3; A9JBG2; A9JGF3; A9JGF4; A9R3L7; A9VXY3; A9Z3H4; A9ZPM4; B0A091; B0BR12; B0CQC4; B0GBL9; B0GVU9; B0H1D2; B0HJI5; B0HXM6; B0KMM7; B0KWQ1; B0LUW1; B0QZJ6; B0R2S9; B0R3G8; B0R4H4; B0R4M4; B0R5D9; B0R6Z6; B0RUG7; B0S5C4; B0SIE1; B0SN43; B0SNZ1; B0SS93; B0U5B4; B0U874; B0V2P2; B0VCE9; B0VED3; B0VLC3; B0VP99; B0XSG6; B0XW74; B0YD86; B1ARG5; B1B498; B1B4A3; B1B4A5; B1BUL5; B1CKA9; B1IJI7; B1J8H8; B1KXP4; B1L3C9; B1L605; B1L7G3; B1L7K6; B1M6J3; B1MEV9; B1MHP8; B1MK17; B1MN65; B1MTP2; B1MWD4; B1QDV9; B1QJM6; B1TBQ1; B1VED0; B1VED3; B1VEI3; B1VFX3; B1VG11; B1VGJ2; B1VGM5; B1VGX8; B1VHJ5; B1VHQ8; B1VI51; B1VIR7; B1VN03; B1VN14; B1VN35; B1VP52; B1VVH8; B1VW26; B1VXP6; B1VYD2; B1W574; B1W592; B1WC11; B1WMR1; B1XBR1; B1XEU5; B1XG08; B1XGB6; B1XGR5; B1ZIT8; B2BET9; B2BGU8; B2CXA8; B2DN37; B2E9E2; B2FHI0; B2FMM9; B2HG85; B2HJT9; B2HLM1; B2HTG9; B2HY82; B2I0W3; B2I1Q3; B2I239; B2I2T6; B2KIE1; B2M1X6; B2QBB2; B2QBB3; B2RAP4; B2RB13; B2RB61; B2SJD7; B2SKW7; B2UPU0; B2VDW2; O05307; O22898; O33855; O53306; O65748; O69484; O75203; O96230; O96232; P72007; P93837; P95288; Q00IB2; Q00IB3; Q00IB4; Q010A6; Q01A47; Q01CP6; Q01FY3; Q02F40; Q02M12; Q02P55; Q02X84; Q030P4; Q035D5; Q03U79; Q03UN1; Q03X23; Q03XN2; Q04E90; Q04EI6; Q04H12; Q04R11; Q04ZC0; Q0BU14; Q0BVL2; Q0BZ31; Q0FAC6; Q0FTK8; Q0FW37; Q0FWY4; Q0G743; Q0ICJ6; Q0JZE2; Q0K0I0; Q0K0M5; Q0K1D7; Q0K1G2; Q0K1J9; Q0K1S0; Q0K235; Q0K2S2; Q0K3D1; Q0K3F0; Q0K313; Q0K471; Q0K4B6; Q0K4U9; Q0K7G7; Q0K7Y6; Q0K7Z8; Q0K9H2; Q0KA53; Q0KA99; Q0KAX9; Q0KAZ6; Q0KBH0; Q0KBJ7; Q0KC36; Q0KCA1; Q0KCD3; Q0KDA3; Q0KDA8;

Q0KDD5; Q0KEY5; Q0RBM2; Q0RFK5; Q0RJW4; Q0RK93; Q0RKB4; Q0RKF3; Q0RKX1; Q0RL18; Q0RLX3; Q0RMI8; Q0RQ81; Q0RSQ2; Q0RV80; Q0S071; Q0S0Z0; Q0S3Z2; Q0S4D2; Q0S4R4; Q0S858; Q0S9M3; Q0SB22; Q0SCC4; Q0SF68; Q0SI90; Q0SJN4; Q0SJP5; Q0SKB1; Q0SKP6; Q0T4Z8; Q0VCZ8; Q0WLQ0; Q0WYX2; Q108M9; Q108N0; Q108N1; Q108N2; Q11P35; Q12WB1; Q13K23; Q13KY8; Q13LU3; Q13PC3; Q13PC5; Q13R36; Q140Q4; Q14GY2; Q16CI1; Q18JH9; Q18JY8; Q1KY54; Q1LVA8; Q1LZF6; Q1M7C9; Q1N4R6; Q1NA91; Q1NAV9; Q1RS47; Q1V104; Q1V1I0; Q1VC07; Q1YK24; Q1YQZ2; Q1YXZ9; Q1ZXQ4; Q28KM2; Q2A4B1; Q2F4C2; Q2FK36; Q2K1H4; Q2KCY7; Q2L5R2; Q2LDN2; Q2LRG1; Q2MF39; Q2N6F7; Q2N6N4; Q2N7M0; Q2NCU9; Q2NFU6; Q2NH56; Q2NHF1; Q2PEY2; Q2PXY8; Q2QC86; Q2QC87; Q2S397; Q2SCW5; Q2SZJ5; Q2T4A8; Q2TA22; Q2TX27; Q2TYD0; Q2U005; Q2U022; Q2U653; Q2U8S5; Q2UB01; Q2UB75; Q2UB92; Q2UBB8; Q2UCI2; Q2UD21; Q2UGB9; Q2UHE5; Q2UJR1; Q2UN15; Q2UNG5; Q2UNS7; Q2UNW0; Q2UNW9; Q2UPN3; Q2URA4; Q2URV8; Q2UTU9; Q2UZQ7; Q2W182; Q2W187; Q2W2Z9; Q2W3Z0; Q2W421; Q2W4C0; Q2W5P6; Q2W7L1; Q2W7X7; Q2YI60; Q2YV45; Q2YZQ4; Q2YZQ5; Q2YZQ6; Q321U7; Q32FS6; Q38BS1; Q3A567; Q3ICG5; Q3IE86; Q3IFA9; Q3IMK1; Q3IMK3; Q3INT3; Q3INU0; Q3INU0; Q3INX4; Q3INY6; Q3IPZ6; Q3IQ14; Q3IQS4; Q3IR40; Q3IUK7; Q3J450; Q3J681; Q3R320; Q3RA12; Q3RGD3; Q3UC67; Q3UKS0; Q3Z2E5; Q3ZXQ4; Q3ZXS3; Q3ZXZ5; Q3ZY24; Q46H09; Q47MN09; Q47ND8; Q47P51; Q47PN7; Q499A9; Q49UK0; Q49VB9; Q4CLW0; Q4CMD9; Q4CN21; Q4CT78; Q4CT79; Q4D203; Q4DD91; Q4DRU2; Q4EM97; Q4EQ99; Q4FNJ5; Q4H1D5; Q4J6R1; Q4J9Q6; Q4J9U1; Q4JSI3; Q4SW1; Q4JTX1; Q4JTY8; Q4JUI7; Q4JWQ1; Q4JX16; Q4JX35; Q4JXK7; Q4JXT1; Q4J18; Q4KD63; Q4PJC2; Q4PK62; Q4QGB2; Q4R450; Q4R778; Q4UDG8; Q4UP88; Q4VQQ0; Q4WD62; Q4X134; Q4X240; Q4XDU0; Q53JH3; Q569W4; Q56WP3; Q56ZG8; Q57NJ4; Q57S37; Q59NN4; Q59X17; Q5A0D9; Q5A4F5; Q5AEJ6; Q5CD72; Q5CD73; Q5CD74; Q5CF20; Q5CQT5; Q5CRD8; Q5CV15; Q5D71; Q5DQU4; Q5E008; Q5E443; Q5EF32; Q5EF33; Q5EF34; Q5F2C5; Q5F2C8; Q5F2D0; Q5FR50; Q5ICG4; Q5ICG5; Q5ICG6; Q5IIQ8; Q5IIQ9; Q5IIR0; Q5IIR1; Q5IIR6; Q5IIR7; Q5IIR8; Q5IIR9; Q5IIS1; Q5IIS2; Q5IIS5; Q5IIS7; Q5IPL2; Q5IPL3; Q5IPL4; Q5IPL6; Q5IPL7; Q5IPL8; Q5IPM0; Q5IPM2; Q5IPM3; Q5IPM5; Q5IPM9; Q5IPN1; Q5IPP1; Q5IPP2; Q5IPP3; Q5IPP4; Q5IPP5; Q5IPP7; Q5IPP8; Q5IPP9; Q5IPQ1; Q5IPQ3; Q5IPQ4; Q5IPQ6; Q5IPQ8; Q5IPQ9; Q5IPR0; Q5IPR1; Q5IPR2; Q5IPR3; Q5IPR4; Q5IPR5; Q5IPR6; Q5IPR7; Q5IPR8; Q5IPR9; Q5IPS2; Q5IPS3; Q5IPS4; Q5IPS5; Q5IPS6; Q5IPS8; Q5IPT3; Q5IPT4; Q5IPT5; Q5IPT6; Q5IPU0; Q5IPU1; Q5IPU3; Q5IPU4; Q5IPU5; Q5IPU6; Q5IPU8; Q5IPU9; Q5IPV0; Q5IPV1; Q5IPV2; Q5IPV4; Q5IPV5; Q5IPV6; Q5IPV8; Q5IPV9; Q5IPW0; Q5IPW1; Q5IPW2; Q5IPW3; Q5IPW4; Q5IPW5; Q5IPW6; Q5IPW8; Q5IPX0; Q5IPX1; Q5IPX2; Q5IPX3; Q5IQN9; Q5IQP0; Q5IQP1; Q5IQP2; Q5IQP3; Q5IQP4; Q5IQP5; Q5IQP6; Q5IQP7; Q5IQP8; Q5IQP9; Q5IQQ0; Q5IQQ1; Q5IQQ4; Q5IQQ9; Q5IQR1; Q5JEW2; Q5JIA8; Q5JWV8; Q5K4L7; Q5KKF0; Q5KWG1; Q5LHZ5; Q5LID5; Q5LKU2; Q5LPZ9; Q5NFI0; Q5NY39; Q5P1M8; Q5P289; Q5PID1; Q5QLE5; Q5QPH3; Q5QVG8; Q5QWP4; Q5R012; Q5S259; Q5SLL7; Q5SN76; Q5TF43; Q5U9J9; Q5VM91; Q5W6W7; Q5YMZ9; Q5YPJ7; Q5YPZ8; Q5YQE6; Q5YQF1; Q5YQI6; Q5YQK2; Q5YR31;

Q5YR43; Q5YR44; Q5YS41; Q5YS42; Q5YT49; Q5YTV1; Q5YTX7; Q5YUJ5; Q5YUS7; Q5YV56; Q5YVD2; Q5YVN2; Q5YVS9; Q5YWI7; Q5YX27; Q5YX39; Q5YXI0; Q5YXP8; Q5YYB5; Q5YYK7; Q5YYV3; Q5YZV8; Q5Z0C2; Q5Z0F3; Q5Z1Y4; Q5Z230; Q5Z2G7; Q5Z2H1; Q5Z2L6; Q5Z3G1; Q5ZWF8; Q633R5; Q63CH5; Q63TT4; Q63V21; Q65GE4; Q66E42; Q66LI9; Q68CH3; Q6A1A3; Q6AED8; Q6D1C9; Q6DF45; Q6DHN4; Q6FEY1; Q6FFF1; Q6GCP1; Q6GK81; Q6GTG6; Q6HCZ9; Q6HJY0; Q6IN15; Q6IU14; Q6J676; Q6J677; Q6KBS6; Q6L1N1; Q6L8F0; Q6LGR0; Q6M1Y6; Q6N1G3; Q6N7F5; Q6PFP1; Q6QLU3; Q6TLJ5; Q6TMA6; Q6XBJ0; Q706Q6; Q706Q7; Q723V0; Q76HN8; Q7KQL7; Q7ME87; Q7MG52; Q7MI50; Q7MP70; Q7MZT6; Q7N131; Q7N526; Q7NZM4; Q7RQ64; Q7TXA1; Q7TZ99; Q7UWD6; Q7VDH7; Q7WC02; Q7WQ01; Q7Z5G3; Q828Q0; Q82AI8; Q82BI2; Q82BZ2; Q82CW3; Q82DZ8; Q82FP6; Q82GU0; Q82KI6; Q82KR5; Q82KT8; Q82LI0; Q82M12; Q82M39; Q82MQ7; Q82NF7; Q82NP2; Q82NP3; Q82NW4; Q82P29; Q82QW8; Q83L73; Q84WQ8; Q87AE3; Q88GJ8; Q8AVA5; Q8AVA6; Q8BK97; Q8BYJ0; Q8C028; Q8D179; Q8D5D8; Q8DBR7; Q8DEE6; Q8DFS0; Q8FM03; Q8G3L1; Q8GHB8; Q8H151; Q8I0V8; Q8I6Z1; Q8K1J7; Q8LFU5; Q8LKS5; Q8LKS6; Q8LKS7; Q8LRT1; Q8LRT2; Q8NR59; Q8P3R2; Q8PF89; Q8R1X1; Q8T5Q5; Q8TAF6; Q8TVZ2; Q8TWL0; Q8VWS5; Q8XYK9; Q8Z4J4; Q8ZR75; Q9YN3; Q92KX0; Q92NF3; Q93GX4; Q93H12; Q93SM4; Q94597; Q946Z2; Q96337; Q96338; Q96537; Q96538; Q985T7; Q988H2; Q98TV3; Q98TV4; Q98TV9; Q99WY9; Q9A929; Q9AKQ7; Q9BMF1; Q9C5U7; Q9C7W4; Q9CAP8; Q9CCT4; Q9CD50; Q9CD79; Q9CD82; Q9CD84; Q9CDB2; Q9CHR0; Q9ESL2; Q9F8U3; Q9F8V2; Q9FNT6; Q9HKD4; Q9HZV4; Q9KBC2; Q9L4M6; Q9NKR2; Q9QWC7; Q9SEY5; Q9SJD4; Q9T009; Q9T0A0; Q9U401; Q9U402; Q9U403; Q9U404; Q9U5A6; Q9U8K3; Q9X3R4; and Q9XIA9. One or more of these genes, or genes encoding variants of the enzymes encoded by these genes, may have utility in producing specific fatty alcohols in recombinant microorganisms.

In some embodiments of the invention, a recombinant microorganism is engineered with a stably introduced heterologous gene that encodes a fatty acyl-CoA reductase, an enzyme of a two component fatty acyl-CoA reductase system, a carboxylic acid reductase, or one or more enzymes of a fatty acid reductase complex (e.g., a bacterial fatty acid reductase complex encoded by a LuxCDE operon) and a gene encoding an acyl-acyl carrier protein (-ACP) thioesterase (TE) enzyme. These TE enzymes catalyze the cleavage of the thioester bond of particular acyl-ACP molecules, which are biochemical intermediates of fatty acid and lipid biosynthesis. These free fatty acids can be converted to fatty alcohols by the production host.

A preferred embodiment of this invention is the expression of one or more medium chain length or long chain length acyl-ACP TEs and acyl-CoA reductase or carboxylic acid reductase enzymes in photosynthetic microorganisms. A medium length fatty acid ranges typically from 8 to 14 carbons, and long chain fatty acids have 16 or 18 carbons. Many acyl-ACP genes have been isolated, and their sequences are available in public databases. Novel genes that encode these acyl-ACP TEs can be isolated from plants that naturally contain large amounts of medium chain fatty acids in their seed oil, including certain plants in the Lauraceae, Lythraceae, Rutaceae, Ulmaceae, and Vochysiaceae families. Other sources of TE enzymes are also contemplated for use with the disclosed invention. For example, many bacteria contain acyl-ACP TE enzymes that would be suitable for this purpose.

The various acyl-ACP TEs from plants can be divided into two main classes, based on their amino acid sequences and their specificity for acyl-ACPs of differing chain lengths and degrees of unsaturation. Inactivation or down regulation of thioesterases involved in the production of fatty acids other than those of the desired length may be also required. For example, FatB enzymes from different species of *Cuphea* have been shown to release fatty acids ranging from eight carbons in length to sixteen carbons in length from the corresponding acyl-ACPs. In some embodiments, one or more acyl-ACP thioesterase genes of a *Cuphea* species, such as but not limited to those disclosed in copending application Ser. No. 12/826,592, filed Jun. 29, 2010, and incorporated herein by reference, can be introduced into a host strain.

Listed below in Table 1 are several plant acyl-ACP TEs along with their substrate preferences. (Fatty acids are designated by standard shorthand notation, wherein the number preceding the colon represents the acyl chain length and the number after the colon represents the number of double bonds in the acyl chain.)

TABLE 1

| Plant Acyl-ACP Thioesterase | |
|---|---|
| *Garcinia mangostana* FatA | 18:1 and 18:0 |
| *Carthamus tinctorius* FatA | 18:1 |
| *Coriandrum sativum* FatA | 18:1 |
| *Cuphea hookeriana* FatB1 | 16:0 |
| *Cuphea hookeriana* FatB2 | 8:0 and 10:0 |
| *Cuphea wrightii* FatB1 | 12:0 to 16:0 |
| *Cuphea palustris* FatB1 | 8:0 and 10:0 |
| *Cuphea palustris* FatB2 | 14:0 and 16:0 |
| *Cuphea calophylla* FatB1 | 12:0 to 16:0 |
| *Umbellularia californica* Fat B1 | 12:0 |
| *Ulmus americana* FatB1 | 8:0 and 10:0 |

The enzymes listed in Table 1 are exemplary and many additional genes encoding acyl-ACP TEs can be isolated and used in this invention. It is anticipated that expression of different acyl-ACP TEs will result in different fatty acids being produced, thus providing fuel and chemical producers with multiple options for formulation. Additional genes that could be used for this purpose include those that encode the following acyl-ACP TEs (referred to by GenPept Accession Numbers): CAA52069.1, CAA52070.1, CAA54060.1, CAA85387.1, CAA85388.1, CAB60830.1, CAC19933.1, CAC19934.1, CAC39106.1, CAC80370.1, CAC80371.1, CAD32683.1, CAL50570.1, CAN60643.1, CAN81819.1, CA017726.1, CA042218.1, CA065585.1, CA068322.1, AAA33019.1, AAA33020.1, AAB51523.1, AAB51524.1, AAB51525.1, AAB71729.1, AAB71730.1, AAB71731.1, AAB88824.1, AAC49001.1, AAC49002.1, AAC49179.1, AAC49180.1, AAC49269.1, AAC49783.1, AAC49784.1, AAC72881.1, AAC72882.1, AAC72883.1, AAD01982.1, AAD28187.1, AAD33870.1, AAD42220.2, AAG35064.1, AAG43857.1, AAG43858.1, AAG43859.1, AAG43860.1, AAG43861.1, AAL15645.1, AAL77443.1, AAL77445.1, AAL79361.1, AAM09524.1, AAN17328.1, AAQ08202.1, AAQ08223.1, AAX51636.1, AAX51637.1, ABB71579.1, ABB71581.1, ABC47311.1, ABD83939.1, ABE01139.1, ABH11710.1, ABI18986.1, ABI20759.1, ABI20760.1, ABL85052.1, ABU96744.1, EAY74210.1, EAY86874.1, EAY86877.1, EAY86884.1, EAY99617.1, EAZ01545.1, EAZ09668.1, EAZ12044.1, EAZ23982.1, EAZ37535.1, EAZ45287.1, NP_001047567.1, NP_001056776.1, NP_001057985.1, NP_001063601.1, NP_001068400.1, NP_172327.1, NP_189147.1, NP_193041.1, XP_001415703.1, Q39473, Q39513, Q41635, Q42712, Q9SQI3, NP_189147.1, AAC49002, CAA52070.1, CAA52069.1, 193041.1, CAC39106, CAO17726, AAC72883, AAA33020, AAL79361, AAQ08223.1, AAB51523, AAL77443, AAA33019, AAG35064, and AAL77445.

Many genes encoding putative acyl-ACP thioesterase enzymes have been reported, including the following Gen-Pept Accession Numbers: A0NIL7; A0PGT6; A0PGT7; A0PXB0; A0QLM3; A0QQX4; A0UVL9; A0W3X2; A1AU09; A1T388; A1UAK6; A1XAM4; A1ZMT4; A2REP5; A3DJY9; A3I1F1; A3PU62; A4T300; A4T7W5; A4VWB5; A4VWB6; A4VWB7; A5FE97; A5I7Y7; A5LEP5; A5LTH7; A5M0P4; A5MHD1; A5N4D4; A5VID1; A6L3F0; A6LDN7; A6LR97; A6M3J8; A7FZF7; A7GJL0; A7H762; A7XZV1; A8MEW2; A8VDR3; A8YTG4; A8ZWR2; A9J9W9; A9KS07; A9P5P1; A9P5P2; A9P5P3; A9P5P5; A9UFC5; A9XK92; A9XUG5; B0PTD9; B0S2E7; B1BC83; B1BEU6; B1BEU7; B1BYH2; B1BYH3; B1ICK8; B1IHP0; B1KU83; B1MVG6; B1MVT0; B1QFF4; B1QMJ6; B1QU73; B1R6C7; B1RJP3; B1RJP4; B1RTS9; B1RTT0; B1S231; B1ZXQ1; B2DHG4; B2DPR6; B2DT86; B2DYE9; B2E4U4; B2HEZ7; B2IQM4; B2KDV9; B2TRE2; B2UMI7; B2V1S4; O04792; O04793; O04794; O24419; O24420; O48568; Q02Z41; Q035X4; Q03E65; Q03K68; Q03SR8; Q03ZG2; Q045U0; Q048X3; Q04E57; Q04JU2; Q0SPT4; Q0TM32; Q0TM33; Q0YND1; Q192S7; Q1BEC8; Q1J6W5; Q1JC16; Q1JH46; Q1JM00; Q1UAA4; Q1WSV1; Q2IGY5; Q2Q1N7; Q2Q1N8; Q2RGE6; Q2S6H1; Q2UZT0; Q2UZT2; Q2ZXQ0; Q312L1; Q38YT1; Q39402; Q39473; Q39513; Q39534; Q39662; Q39663; Q39UW1; Q3DQT8; Q3Y000; Q41635; Q41635; Q41917; Q42558; Q42561; Q42562; Q42712; Q43718; Q43745; Q48TU8; Q48Z34; Q4KTZ8; Q4KU00; Q4KU01; Q5FLZ7; Q5L9J1; Q5LZC2; Q5M3X4; Q5QMV2; Q5XCD7; Q64PS9; Q6H643; Q6I8R5; Q6K1M5; Q899Q1; Q8A611; Q8K7R4; Q8L6B1; Q8S9G4; Q8SMI2; Q8VXJ5; Q8VXJ6; Q94IN9; Q97D89; Q97Q23; Q9FNS7; Q9FNS8; Q9FPM5; Q9FQX7; Q9FQX8; Q9FQX9; Q9FQY0; Q9FQY1; Q9FT16; Q9S8U5; Q9SMI9; Q9SNP5; and Q9SQI3. One or more of these genes, or genes encoding variants of the enzymes encoded by these genes, may have utility in producing specific fatty alcohols in recombinant microorganisms.

The following embodiments are exemplary and do not limit the scope of the invention in any way.

In one embodiment, a transgenic microorganism includes exogenous gene(s) that encodes an alcohol-forming acyl-CoA reductase and further includes one or more exogenous genes encoding a fatty aldehyde-generating acyl-CoA reductase or a carboxylic acid reductase. The alcohol-forming acyl-Co reductase is an enzyme that generates alcohol from an acyl-CoA substrate. In some embodiments the transgenic microorganism further includes one or more genes that encodes an acyl-CoA synthetase or a thioesterase. In these embodiments, the alcohol-forming acyl-CoA reductase can be, as nonlimiting examples, bfar from *Bombyx mmori*; jjfar from *Simmondsia chinensis*, an acyl-CoA reductase from *Titicum aestivum*, mfar1 of *Mus musculus*, mfar2 from *Mus musculus*, hfar from *H. sapiens*, FARXIII of *Ostrinia scapulalis*, MS2 of *Z. mays*, or MS2, FAR4, FAR6, or CER4 of *Arabidopsis thaliana*. An alcohol-forming fatty acyl-CoA reductase can also be a prokaryotic enzyme, such as those encoded by *Marinobacter aquaeoli* VT8 2220 gene (SEQ ID NO:9, protein sequence SEQ ID NO:8), *Marinobacter algicola* DG893, Accession ZP_01892457; SEQ ID NO:21, protein sequence is SEQ ID NO:20; *Hahella chejuensis* KCTC 2396 HCH_05075; Accession YP_436183, Gene ID 3837725 SEQ ID NO:23, protein sequence is SEQ ID NO:22; *Oceanobacter* sp. RED65 ZP_01305629, gb EAT13695 SEQ ID NO:25, protein sequence is SEQ ID NO:24, or *Marinobacter aquaeoli* VT8 2220 gene, Maqu_2507 (SEQ ID NO:27, protein sequence is SEQ ID NO:26). The fatty aldehyde-generating acyl-CoA reductase can be, for example one or more lux genes (for example, luxC and luxE, that generate fatty aldehydes), AcrM-1, Acr1, or other genes identified as acyl-CoA reductases that form a fatty aldehyde as the product of the reductase activity. Carboxylic acid reductases include, without limitation, the Nocardia ATP/NADPJH-dependent carboxylic acid reductase gene (GI: 40796043) and others that generate fatty aldehydes from fatty acids.

In some embodiments, the invention includes methods of producing a fatty alcohol or fatty alcohol derivative by culturing a transgenic microorganism that includes one or more genes encoding a prokaryotic alcohol-forming acyl-CoA reductase, such as those encoded by *Marinobacter aquaeoli* VT8 2220 gene (SEQ ID NO:9, protein sequence SEQ ID NO:8), *Marinobacter algicola* DG893, Accession ZP_01892457; SEQ ID NO:21, protein sequence is SEQ ID NO:20; *Hahella chejuensis* KCTC 2396 HCH_05075; Accession YP_436183, Gene ID 3837725 SEQ ID NO:23, protein sequence is SEQ ID NO:22; *Oceanobacter* sp. RED65 ZP_01305629, gb EAT13695 SEQ ID NO:25, protein sequence is SEQ ID NO:24, or *Marinobacter aquaeoli* VT8 2220 gene, Maqu_2507 (SEQ ID NO:27, protein sequence is SEQ ID NO:26), and isolating at least one fatty alcohol from the cells or media. In some embodiments, the microorganism is a prokaryotic microorganism. In some embodiments, the microorganism is a photosynthetic microorganism. In some embodiments, the microorganism is grown phototrophically.

In further embodiments, a transgenic microorganism that includes an exogenous gene encoding an N-terminally truncated eukaryotic acyl-CoA reductase is provided, and methods of using the transgenic microorganism for producing a fatty alcohol or fatty alcohol derivative. In some embodiments, the transgenic microorganism is a prokaryotic microorganism. In exemplary embodiments, the truncated eukaryotic acyl-CoA reductase is SEQ ID NO: 28 or SEQ ID NO:31. Additional embodiments include genes encoding truncated eukaryotic acyl-CoA reductases in which the truncation occurs within 10 amino acids of the N-terminus of SEQ ID NO: 28 or SEQ ID NO:31 when the sequences are aligned for maximum homology. In some embodiments, the microorganism is a photosynthetic microorganism. In some embodiments, the microorganism is grown phototrophically to produce a fatty alcohol or fatty alcohol derivative.

In other embodiments, a transgenic microorganism includes an exogenous gene that encodes an acyl-CoA reductase, one or more exogenous genes encoding a fatty acid reductase complex and an exogenous gene that encodes a transporter protein. Expression of the transporter protein in some embodiments increases the amount of fatty alcohol or fatty derivative by the transgenic host microorganism.

In some embodiments, a transgenic host microorganism includes an exogenous gene that encodes an acyl-CoA reductase or genes encoding a fatty acid reductase complex, an exogenous gene that encodes an acyl-ACP thioesterase, and an exogenous gene that encodes an acyl-CoA synthetase. The host microorganism can optionally further include an exogenous gene that encodes a beta-ketoacyl-ACP synthase.

In any of the forgoing embodiments, the transgenic host organism can further include a mutation that reduces the expression or activity of at least one of an acyl-CoA oxidase or a fatty alcohol oxidase. In any of the forgoing embodiments, the transgenic organism can be genetically engineered such that a gene encoding a fatty acid-CoA oxidase or a gene encoding a fatty alcohol oxidase is not expressed, has a reduced level of expression, or expresses an enzyme having reduced or negligible activity.

An additional embodiment of this invention is to introduce an acyl-CoA reductase gene or genes encoding a fatty acid reductase complex and an acyl-ACP TE gene into a recombinant microorganism in which one or more genes that encode beta-oxidation pathway enzymes have been inactivated or are downregulated, such as, for example, a gene encoding an acyl-CoA dehydrogenase. The host organism can optionally also include an exogenous gene encoding an acyl-CoA synthetase. Reducing the expression of one or more beta-oxidation pathway enzymes can prevent the degradation of fatty acids released from acyl-ACPs, thus enhancing the conversion of fatty acids to fatty alcohols. In cases where the desired products are medium chain fatty acid derivatives, the inactivation or downregulation of genes that encode medium chain-specific acyl-CoA oxidase enzymes is contemplated. Mutations in the genes or their regulatory regions can be introduced either by recombinant or non-recombinant methods.

In another embodiment of this invention, various heterotrophic and photosynthetic bacteria, including cyanobacteria, can be genetically engineered to produce specific acyl-CoA molecules that do not normally occur in significant quantities; these acyl-CoA molecules can then be can be used as substrates for acyl-CoA reductases that are also produced in the host cells as a result of introduced transgenes. To accomplish this, a gene that encodes an acyl-acyl carrier protein (acyl-ACP) thioesterase with a particular acyl-ACP substrate specificity can be introduced along with an acyl-CoA synthetase that is able to produce the corresponding acyl-CoA molecule from the free fatty acid released as a result of the introduced acyl-ACP thioesterase activity. The acyl-CoA molecule can then be converted to the corresponding fatty alcohol via the activity of the introduced acyl-CoA reductase. For example, to produce octanol in a photosynthetic or heterotrophic bacterium, one could:
 a) Add a transgene that encodes an acyl-ACP thioesterase that has a high degree of specificity for octanoyl-ACP; and
 b) Add a transgene that encodes an acyl-CoA synthetase that has a high degree of specificity for octanoic acid; and
 c) Add a transgene that encodes an acyl-CoA reductase that has a high degree of specificity for octanoyl-CoA.

In an alternate embodiment, one could add a transgene that encodes an acyl-ACP thioesterase that has a high degree of specificity for octanoyl-ACP and add one or more transgenes that encode a fatty acid reductase complex that uses octanoic acid as a substrate.

In another embodiment of this invention, a dehydratase gene can be introduced into the fatty-alcohol-producing recombinant microorganisms described above would result in the production of various alpha-olefins. In this manner, strains could be engineered to produce octene from octanol, decene from decanol, etc.

In another embodiment, alkanes are produced via the introduction of a fatty aldehyde decarbonylase to the host organism.

In each case, it would be necessary to operably link the transgene to appropriate gene expression regulatory elements (i.e., a promoter and terminator). A similar strategy could be employed to produce other fatty alcohols, including decanol, dodecanol, tetradecanol, hexadecanol, hexadecenol, octadecanol, octadecenol, etc.

Transformation of Host Organisms

Methods for transformation of higher plants, bacteria, and yeasts are well known. Algae and photosynthetic bacteria can be transformed by any suitable methods, including, as non-limiting examples, natural DNA uptake (Chung et al. (1998) *FEMS Microbiol. Lett.* 164: 353-361; Frigaard et al. (2004) *Methods Mol. Biol.* 274: 325-40; Zang et al. (2007) *J. Microbiol.* 45: 241-245), conjugation, transduction, glass bead transformation (Kindle et al. (1989) *J. Cell Biol.* 109: 2589-601; Feng et al. (2009) *Mol. Biol. Rep.* 36: 1433-9; U.S. Pat. No. 5,661,017), silicon carbide whisker transformation (Dunahay et al. (1997) *Methods Mol. Biol.* (1997) 62: 503-9), biolistics (Dawson et al. (1997) *Curr. Microbiol.* 35: 356-62; Hallmann et al. (1997) *Proc. Natl. Acad. USA* 94: 7469-7474; Jakobiak et al. (2004) *Protist* 155:381-93; Tan et al. (2005) *J. Microbiol.* 43: 361-365; Steinbrenner et al. (2006) *Appl Environ. Microbiol.* 72: 7477-7484; Kroth (2007) *Methods Mol. Biol.* 390: 257-267; U.S. Pat. No. 5,661,017) electroporation (Kjaerulff et al. (1994) *Photosynth. Res.* 41: 277-283; Iwai et al. (2004) *Plant Cell Physiol.* 45: 171-5; Ravindran et al. (2006) *J. Microbiol. Methods* 66: 174-6; Sun et al. (2006) *Gene* 377: 140-149; Wang et al. (2007) *Appl. Microbiol. Biotechnol.* 76: 651-657; Chaurasia et al. (2008) *J. Microbiol. Methods* 73: 133-141; Ludwig et al. (2008) *Appl. Microbiol. Biotechnol.* 78: 729-35), laser-mediated transformation, or incubation with DNA in the presence of or after pre-treatment with any of poly(amidoamine) dendrimers (Pasupathy et al. (2008) *Biotechnol. J.* 3: 1078-82), polyethylene glycol (Ohnuma et al. (2008) *Plant Cell Physiol.* 49: 117-120), cationic lipids (Muradawa et al. (2008) *J. Biosci. Bioeng.* 105: 77-80), dextran, calcium phosphate, or calcium chloride (Mendez-Alvarez et al. (1994) *J. Bacteriol.* 176: 7395-7397), optionally after treatment of the cells with cell wall-degrading enzymes (Perrone et al. (1998) *Mol. Biol. Cell* 9: 3351-3365). *Agrobacterium*-mediated transformation can also be performed on algal cells, for example after removing or wounding the algal cell wall (e.g., WO 2000/62601; Kumar et al. (2004) *Plant Sci.* 166: 731-738). Biolistic methods are particularly successful for transformation of the chloroplasts of plant and eukaryotic algal species (see, for example, Ramesh et al. (2004) *Methods Mol. Biol.* 274: 301-307; Doestch et al. (2001) *Curr. Genet.* 39: 49-60; U.S. Pat. No. 7,294,506; WO 2003/091413; WO 2005/005643; and WO 2007/133558, all incorporated herein by reference in their entireties).

In some preferred embodiments of the invention, a gene or genes encoding enzymes that participate in the synthesis of fatty acid products (such as genes as disclosed herein), is cloned into an expression vector for transformation into a plant, alga, or photosynthetic or nonphotosynthetic bacterium. The vector includes sequences that promote expression of the transgene of interest or multigene operon of interest, such as a promoter, and may optionally include a transit peptide-encoding sequence for directing the expressed reductase to the chloroplast of transformed eukaryotic cells, an intron sequence, a sequence having a polyadenylation signal, etc. Alternatively, if the vector does not contain a promoter in operable linkage with the gene of interest, the gene can be transformed into the cells such that it becomes operably linked to an endogenous promoter by homologous recombination or vector integration.

In some embodiments, a vector is designed for integration of the gene into the host genome. For example, vectors used for higher plant transformation include but are not limited to *Agrobacterium*-based vectors that are designed for integrating transgenes (exogenous genes transformed into the host plant) into the genome of the plant. In other embodiments, vectors can be: 1) targeted for integration into a plant or algal chromosome by including flanking sequences that enable homologous recombination into the chromosome, 2) targeted for integration into endogenous host plasmids by including flanking sequences that enable homologous recombination into the endogenous plasmids, or 3) designed such that the expression vectors replicate within the chosen host.

Artificial chromosome vectors can also be used for the transformation of higher plants or algae, for example, vector constructs that include a centromere sequence and an origin of replication so that the vector and its integrated sequences can be maintained in the plant or alga (see, for example, U.S. Pat. No. 7,456,013 incorporated by reference herein in its entirety). Artificial chromosomes can accommodate more transgenes than can other types of vectors such as, for example, *Agrobacterium*-based vectors, and therefore can be used in higher plant or algal systems when more than one gene that encodes an enzyme that participates in the synthesis of a fatty acid product is transformed into an organism.

In some cases in which it may be advantageous to transform the chloroplast of a higher plant or alga, vectors can be designed to have regions of sequences flanking the transgene (e.g., an acyl-CoA reductase gene or fatty acid reductase operon, or another gene for synthesis of a fatty acid product) that are homologous to chloroplast sequences to promote homologous recombination and integration of the sequence of interest. In these embodiments, the vector preferably includes a promoter for expressing the transgene(s), in which the promoter functions in the chloroplast.

Vectors designed for expression of a gene in microalgae can in some embodiments include a promoter active in microalgae operably linked to the exogenous gene being introduced. A variety of gene promoters and terminators that function in green algae can be utilized in expression vectors, including, but not limited to promoters and terminators from *Chlamydomonas* and other algae (see, for example, *Plant Cell Physiol* 49: 625-632 (2008)), promoters and terminators from viruses, and synthetic promoters and terminators.

For transformation of diatoms, a variety of gene promoters that function in diatoms can be utilized in these expression vectors, including, but not limited to: 1) promoters from *Thalassiosira* and other heterokont algae, promoters from viruses, and synthetic promoters. Promoters from *Thalassiosira pseudonana* that would be suitable for use in expression vectors include an alpha-tubulin promoter, a beta-tubulin promoter, and an actin promoter. Promoters from *Phaeodactylum tricornutum* that would be suitable for use in expression vectors include an alpha-tubulin promoter, a beta-tubulin promoter, and an actin promoter. The terminators associated with these genes, other diatom genes, or particular heterologous genes can be used to stop transcription and provide the appropriate signal for polyadenylation.

In some instances it can be advantageous to express a heterologous enzyme or enzymes, such as but not limited to an acyl-CoA reductase or fatty acid reductase enzymes, at a certain point during the growth of the transgenic host to minimize any deleterious effects on the growth of the transgenic organism and/or to maximize production of the fatty acid product of interest. In these instances one or more exogenous genes introduced into the transgenic organism can be operably linked to an inducible promoter. The promoter can be a lac promoter, a tet promoter (e.g., U.S. Pat. No. 5,851,796), a hybrid promoter that includes either or both of portions of a tet or lac promoter, a hormone-responsive promoter (e.g., an ecdysone-responsive promoter, e.g., U.S. Pat. No. 6,379,945) a metallothionien promoter (U.S. Pat. No. 6,410,828), or a pathogenesis-related (PR) promoter that can be responsive to a chemical such as, for example, salicylic acid, ethylene, thiamine, or BTH (U.S. Pat. No. 5,689,044). An inducible promoter can also be responsive to light or dark (U.S. Pat. No. 5,750,385, U.S. Pat. No. 5,639,952) or temperature (U.S. Pat. No. 5,447,858; Abe et al., *Plant Cell Physiol.* 49: 625-632 (2008); Shroda et al. *Plant J.* 21: 121-131 (2000)). The foregoing list is exemplary and not limiting. The promoter sequences can be from any organism, provided that they are functional in the host organism. Inducible promoters as used in the constructs of the present invention can use one or more portions or one or more domains of the aforementioned promoters or other inducible promoters fused to at least a portion of a different promoter that operates in the host organism to confer inducibility on a promoter that operates in the host species.

A variety of gene promoters that function in cyanobacteria can be utilized in expression vectors, including, but not limited to: 1) the lac, tac, and trc promoters that are inducible by the addition of isopropyl β-D-1-thiogalactopyranoside (IPTG), 2) promoters that are naturally associated with transposon- or bacterial chromosome-borne antibiotic resistance genes (neomycin phosphotransferase, chloramphenicol acetyltrasferase, spectinomycin adenyltransferase, etc.), 3) promoters of various heterologous bacterial and native cyanobacterial genes, 4) promoters from viruses and phages, and 5) synthetic promoters. Promoters isolated from cyanobacteria that have been used successfully include the following:

secA (secretion; controlled by the redox state of the cell)
rbc (Rubisco operon)
psaAB—(PS I reaction center proteins; light regulated)
psbA—(D1 protein of PSII; light-inducible)

Likewise, a wide variety of transcriptional terminators can be used for expression vector construction. Examples of possible terminators include, but are not limited to, psbA, psaAB, rbc, secA, and T7 coat protein.

Transformation vectors preferably also include a selectable marker, such as but not limited to a drug resistance gene, an herbicide resistance gene, a metabolic enzyme or factor required for survival of the host (for example, an auxotrophic marker), etc. Transformed cells can be optionally selected based upon the ability to grow in the presence of the antibiotic or other selectable marker under conditions in which cells lacking the resistance cassette or auxotrophic marker would not grow. In some embodiments a non-selectable marker may be present on a vector, such as a gene encoding a fluorescent protein or enzyme that generates a detectable reaction product. In an alternative transformation strategy, selectable or non-selectable markers can be provided on a separate construct, where both the gene-of-interest construct and the selectable marker construct are used together in transformation protocols, and selected transformants are analyzed for co-transformation of the construct that includes the gene-of-interest (see, for example, Kindle (1990) Proc. Natl. Acad. Sci. USA 87: 1228-32; Jakobiak et al. (2004) Protist 155:381-93).

Growth of Transformed Organisms

Culture of bacteria and fungi such as yeast are well known. Algae and photosynthetic bacteria can be cultured phototrophically, in the absence of a fixed carbon source, or mixotrophically, where the cultures are supplied with light for at least part of the day, and also supplied with a reduced carbon source, such as a (e.g., glucose, fructose, galactose, mannose, rhamnose, arabinose, xylose, lactose, sucrose, maltose), an organic acid (e.g., actetate, citrate, succinate), or glycerol. The photosynthetic organism in some embodiments is cultured mixotrophically, in which the organism is grown in the presence of light for at least a part of the day, and also provided with one or more sources of reduced carbon. A photosynthetic organism can be grown mixotrophically for a period of time, followed by a period of phototrophic growth, or vice versa.

Media for phototrophic or mixotrophic growth of algae are known in the art, and media can be optimized to enhance growth or production of fatty acid products for a particular species. Artificial light sources can be used as the sole light source or to enhance or extend natural light.

In some embodiments, a transgenic organism contains an exogenous gene for one or more enzymes that participate in the synthesis of a fatty acid product as described herein that are under the control of an inducible promoter, as described above, and the transgenic organism is grown or cultured for a period of time while the transgene(s) is/are not induced. At a point during the growth period, which can be empirically determined based on production levels of the fatty acid product, the gene can be induced, for example, by a period of dark or light, raising or lowering of the temperature, or addition of one or more nutrients or chemicals to the culture medium. The transgenic organism can be maintained under inducing conditions for any feasible amount of time for production of protein(s) encoded by the transgene(s).

Growth of algae can be in open areas, such as, for example, ponds, canals, channels, raceways, or tanks, or can be in bioreactors. Bioreactors are preferred for mixotrophic growth, and can also be used for phototrophic growth. The bioreactors can be of any sizes and form, and can include inlets for providing nutrients, additives, or gases, such as but not limited to air or $CO_2$. A bioreactor preferably also has an outlet for sampling of the culture. A bioreactor can be conFIG.d such that the algal culture is mixed during the growth period, for example, by stirriring, rocking, shaking, inverting, bubbling of gases through the culture, etc. Outdoor ponds, raceways, tanks, canals, etc. can also be designed for mixing of cultures through, for example, paddles, pumps, hoses or jets for circulation of the culture media, or tubes, hoses or inlets for supplying air or $CO_2$ to the culture.

Production of Fatty Acid Products

Where cultures of algae or photosynthetic bacteria are employed in the methods, the fatty acid product (which in some preferred embodiments is a medium chain fatty acid product, such as a medium chain fatty alcohol, for example, octanol, decanol, dodecanol, tetradecanol, or hexadecanol can be isolated from the culture medium, from the cells, or from whole culture (culture medium plus cells).

Fatty acid products (e.g., lipids, fatty acids, aldehydes, alcohols, esters, alkenes, and alkanes) produced by cells of the invention can be harvested, or otherwise collected, by any convenient means. For example, hydrocarbons secreted from cells can be centrifuged to separate the hydrocarbons in a hydrophobic layer from contaminants in an aqueous layer and optionally from any solid materials as a precipitate in after centrifugation. Material containing cell or cell fractions can be treated with proteases to degrade contaminating proteins before or after centrifugation. In some instances the contaminating proteins are associated, possibly covalently, to hydrocarbons or hydrocarbon precursors which form hydrocarbons upon removal of the protein. In other instances the hydrocarbon molecules are in a preparation that also contains proteins.

Proteases can be added to hydrocarbon preparations containing proteins to degrade proteins (for example, the protease from *Streptomyces griseus* can be used (SigmaAldrich catalog number P5147). After digestion, the hydrocarbons are preferably purified from residual proteins, peptide fragments, and amino acids. This purification can be accomplished, for example, by methods listed above such as centrifugation and filtration.

In some embodiments, fatty acid products such as fatty alcohols are isolated from algal cells or whole culture that includes cells by generating a cell lysate. The cells are first disrupted, for example, by heat, treatment with an acid or base, treatment with enzymes, osmotic shock, mechanical disruption, sonication, freeze-thaw, etc., and then intracellular and cell membrane/cell wall-associated fatty alcohols can be collected from the lysed cells.

Fatty alcohols can be extracted with a hydrophobic solvent such as hexane. Cells can be freeze dried and pulverized followed by extraction with n-hexane (Miao and Wu, Biosource Technology (2006) 97:841-846).

In embodiments in which algae or microorganisms secrete fatty acid products, the cells can be removed from the culture medium, for example, by centrifugation, sedimentation, flocculation, or filtering, and the culture medium can be extracted with a solvent such as hexane.

Capture and recovery of fatty acid products such as fatty alcohols that are secreted into the culture medium by recombinant bacteria and algae, such as cyanobacteria, as described above, can also be performed by adsorbing the fatty acid products secreted into the culture medium to small, easily harvested objects. In this method, small objects that are able to bind fatty acid products such as fatty alcohols, referred to for purposes of this specification as "fat adsorbing objects," are circulated in the culture medium for an appropriate amount of time and then collected by physical separation. The fatty alcohols are then eluted from the fat adsorbing objects by the use of an appropriate non-polar solvent. Evaporation of the solvent, followed by further processing of the isolated fatty alcohols can then be carried out to yield chemicals and fuels that can be used for a variety of commercial purposes.

The fat adsorbing objects (for example, spheres ranging from 1 mm to 30 mm) can be manufactured from various materials including, but not limited to, polymers including, for example, polyethylene and derivatives, polystyrene and derivatives, polyamide and derivatives, polyester and derivatives, polyurethane and derivatives, polyacrylates and derivatives, silicone and derivatives, and polysaccharide and derivatives. Certain glass and ceramic materials can also be used as the solid support component of the fat adsorbing objects. The surfaces of the fat adsorbing objects are modified so that they are able to bind fatty alcohols. An example of such modification is the introduction of ether-linked alkyl groups having various chain lengths, preferably 10-30 carbons. In another example, acyl chains of various lengths can be attached to the surface of the fat adsorbing objects via ester, thioester, or amide linkages.

In another embodiment of this invention, the fat adsorbing objects are coated with inorganic compounds known to bind fatty alcohols. Examples of such compounds include but are not limited to aluminum hydroxide, graphite, anthracite, and silica.

To capture secreted fatty alcohols from the culture medium used to cultivate the photosynthetic microorganisms, the fat adsorbing objects are circulated in the culture medium for an appropriate period of time, and then removed from the culture by the use of filters or screens or other physical separation devices. Alternatively, the fat absorbing objects can be provided in a column or tube through which the algal culture can be passed.

The fatty alcohols bound to the fat adsorbing objects are then eluted by the use of an appropriate non-polar solvent such as hexane, after which the fat adsorbing objects can be dried and returned to the culture medium so that more fatty acids can be bound and removed. The hexane containing the dissolved fatty alcohols is then evaporated, leaving the fatty alcohols in a purified state for further conversion to chemicals and fuels. The fat adsorbing objects can be designed to be neutrally buoyant or positively buoyant to enhance circulation in the culture medium. It is anticipated that a continuous cycle of fatty alcohols removal and recovery using the fat adsorbing objects can be implemented by utilizing the steps outlined above.

EXAMPLES

Example 1

Expression Constructs That Include Acyl-CoA Reductase Genes

A DNA fragment comprising a functional operon was synthesized such that it contained the following elements in the given order: 1) the *Mus musculus* medium chain acyl-CoA synthetase gene (MACS1, NCBI reference No. EDL17174) codon-optimized for expression in *Synechocystis* sp. PCC6803, the *S. elongatus* KaiBC intergenic region, and the *Ostrinia scapulalis* fatty acyl-CoA reductase (FARXIII, NCBI reference No. ACJ06520) gene, also codon-optimized for expression in *Synechocystis* sp. PCC6803. The nucleotide sequence of this functional operon is provided in SEQ ID NO:1. Codon optimization was performed by the use of the "Gene Designer" (version 1.1.4.1) software program provided by DNA2.0, Inc. The plasmid pSGI-BL69 was constructed by inserting the operon between the NcoI and BamHI restriction sites of the vector YC79, which contains the trcY promoter, the lacI$^q$ gene, and homology arms that enable integration of the expression cassette into the "RS2" site of the *Synechocystis* sp. PCC 6803 genome (Aoki, et al., *J. Bacteriol* (1995) 177:5606-5611).

An additional vector was constructed to enable the expression and testing of an *Escherichia coli* str. K-12 substr. W3110 short chain acyl-CoA synthetase gene (FadK, NCBI reference No. AP_002321) in combination with the *Arabidopsis thaliana* Fatty acyl-CoA reductase gene (FAR6, Swiss-Prot: B9TSP7.1; Accession NM_115529, GI: 18410556), codon-optimized for expression in *Synechocystis* sp. PCC6803. The nucleotide sequence of this FadK/FAR6 functional operon is provided in SEQ ID NO:2. This operon was placed between the NcoI and BamHI restriction sites in the plasmid YC79 to form pSGI-BL70.

A third vector was constructed to enable the expression and testing of an *Escherichia coli* str. K-12 substr. W3110 long chain acyl-CoA synthetase gene (FadD, NCBI reference No. YP_001724804.1) in combination with the *Arabidopsis thaliana* Fatty acyl-CoA reductase gene (FAR6, Swiss-Prot: B9TSP7.1), codon-optimized for expression in Synechocystis sp. PCC6803. The nucleotide sequence of this FadD/FAR6 functional operon is provided in SEQ ID NO:3. This operon was placed between the NcoI and BamHI restriction sites in the plasmid YC79 to form pSGI-BL71.

A fourth and a fifth vector were constructed to enable the expression and testing of the *Photorhabdus luminescens* fatty acid reductase (luxC, Genbank accession: M90093), acyl transferase (luxD, Genbank accession: M90093), and acyl protein synthetase (luxE, Genbank accession: M90093) genes. The nucleotide sequence of this luxCDE functional operon is provided in SEQ ID NO:4. This operon was placed between the EcoRI and SacI restriction sites of plasmid pUC 19 to form pSGI-BL77, and between the NcoI and BamHI restriction sites of the plasmid YC79 to form pSGI-BL78.

A *Synechocystis* sp. PCC 6803 codon usage table was utilized to codon optimize the coding region for the *Cuphea leptopoda* C14fatB 1 thioesterase gene having a substrate preference for C10 and C16 fatty acids. The synthetic gene constructs for expression of the higher plant thioesterase gene were made with a truncation of the 5' end to exclude the predicted plastid transit peptide-encoding region at the amino-terminus. The codon-optimized N-terminally truncated C14FatB1 gene was synthesized by DNA2.0 (Menlo Park, Calif.) and was cloned into a *Synechocystis* sp. PCC 6803 integration vector pSGI-YC28. pSGI-YC28 contains the modified trc promoter from pTrcHisA. The C14FatB1 operon was subcloned into pACYC 184 vector at the BamHI site to form vector pAC/5A using the InFusion system (Clontech, Mountainview, Calif.). The nucleotide sequence of this C14FatB 1 gene is provided in SEQ ID NO:5; the encoded protein is provided in SEQ ID NO:6.

Example 2

Production of Fatty Alcohol in *E. coli*

Electro-competent *E. coli* K19 cells were co-transformed with 100 ng pAC/5A and 100 ng BL69, BL70, BL71, or BL77 by electroporation. Transformants were inoculated into 4 mL LB medium containing chloramphenicol (30 mg/L) or/and spectinomycin (50 mg/L) as appropriate on a rotary shaker (200 rpm) at 30° C. overnight. Overnight cultures were inoculated in LB medium to obtain 100 mL of culture having an initial culture OD$_{730\,nm}$ of 0.15-0.25. After 2 hr of cultivation, 100 uL 1M IPTG was added for induction. A volume of 50 mL culture was collected 24 hr post inoculation and treated with 0.2 mg/mL lysozyme and 2 mM EDTA for 1 hr at 30° C. Cell debris was removed after centrifuging the cell lysate at 3500×g for 15 min. Supernatants were collected and acidified to a pH of less than 4.0. Supernatants were extracted by mixing with methylene chloride at a 1:1 ratio (vortexed for 1 min) and the organic layer was concentrated in vacuo to 1 mL. Fatty alcohol content was analyzed in Example 3.

Example 3

Gas Chromatographic Analysis of Fatty Alcohols Produced by Transformed *E. coli* Strains The samples for analysis were prepared by adding 50 uL of 5 mM 1-hexanol in ethanol (used as an internal standard) to 500 uL of the sample being tested. The sample was then analyzed by GC/MS.

An Agilent 7890A gas chromatograph with a J&W Scientific HP-5MS capillary column (30 m length, 0.25 mm internal diameter, 0.25 µm film thickness) coupled to an Agilent 5975C mass spectrophotometer was used for analysis. The GC oven was programmed as follows: 90° C. for 0.5 min., then heated at 20° C/min. to 285° C. The injector temperature was kept at 280° C., and a 5:1 split injection was used. Helium was used as a carrier gas at a flow rate of 1.2 mL/min. The analytes were identified by comparison to injected standard compounds, as well as by use of the Wiley mass spectral library. The limit of quantitation for the analytes was 5 uM.

Spiking and recovery experiments show that the extraction method recovers about 80% of each analyte.

TABLE II

| | Fatty alcohol production (in μM) in E. coli K19. | | | | |
|---|---|---|---|---|---|
| | pAC/5A | pAC/5A pSGI-BL69 (MACS1/FARXIII) | pAC/5A pSGI-BL70 (FadK/FAR6) | pAC/5A pSGI-BL71 (FadD/FAR6) | pAC/5A pSGI-BL77 (LuxCDE) |
| 1-Decanol | ND | ND | Not determined | ND | 111.2 |
| 1-Dodecanol | ND | ND | Not determined | ND | 166.9 |
| 1-Tetradecanol | ND | ND | Not determined | ND | 301.4 |

ND indicates "not detected" (<5 uM).

Example 4

Production of Fatty Alcohol in the Cyanobacterium *Synechocystis*

*Synechocystis* sp. PCC6803 cells were transformed with plasmids pSGI-BL69 (MACS1/FARXIII genes), pSGI-BL70 (FadK/FAR6 genes), pSGI-BL71 (FadD/FAR6 genes) and pSGI-BL78 (LuxCDE genes) as described by (Zang et al. Microbiology 45:241-245). Both recombinant and wild-type control strains were pre-cultivated in 30 mL of BG-11 medium to mid-log phase ($OD_{730\ nm}$=0.7-0.9) on a rotary shaker (150 rpm) at 30° C. with constant illumination (40 μEinsteins $m^{-2}\ sec^{-1}$) and $CO_2$(1%). Mid-log phase cultures were inoculated in BG-11 containing 1 mM IPTG to obtain 50 mL of culture having an initial culture $OD_{730\ nm}$ of 0.7-0.9). Cultivation was performed under the same conditions as pre-cultivation. Kanamycin (10 μg/ml) and spectinomycin (25 μg/ml) were included in recombinant cultures as appropriate. Products of the cultures were analyzed in Example 5.

Example 5

Gas Chromatographic Analysis of Fatty Alcohols Produced by Transformed *Synechocystis* Strains Samples are analyzed for the production of fatty alcohols by the four transgenic *Synechocystis* strains as well as the wild-type strain (control) using standard gas chromatographic methods as provided in Example 3 to determine gene combinations that provide optimal levels of fatty alcohols of specific chain lengths.

Example 6

Expression Constructs for Fatty Alcohol Production

A DNA fragment comprising a functional operon was synthesized to enable the expression and testing of the *Escherichia coli* str. K-12 substr. W3110 long chain acyl-CoA synthetase gene (FadD, NCBI reference No. YP_001724804.1) in combination with the *Photorhabdus luminescens* fatty acid reductase (luxC, Genbank accession: M90093). The genes were both codon-optimized for expression in Synechocystis sp. PCC6803 and were separated by the *S. elongatus* KaiBC intergenic region. The nucleotide sequence of this functional FadD-luxC operon is provided in SEQ ID NO:7. This operon was placed between the NcoI and BamHI restriction sites in the plasmid YC79 to form pSGI-BL76.

An additional vector was constructed to enable the expression and testing of the *Escherichia coli* str. K-12 substr. W3110 long chain acyl-CoA synthetase gene FadD (NCBI reference No. YP_001724804.1) in combination with the *Marinobacter aquaeoli* VT8 2220 gene encoding the "Maqu_2220" protein (amino acid sequence provided as SEQ ID NO:8; Genbank Accession ABM19299; GI: 120324984; gene sequence provided as SEQ ID NO:9), codon-optimized for expression in *Synechocystis* sp. PCC6803. The nucleotide sequence of this FadD/Maqu 2220 functional operon containing the KaiBC intergenic region is provided in SEQ ID NO:10. This operon was placed between the NcoI and BamHI restriction sites in the plasmid YC79 to form pSGI-BL73.

A vector was also constructed to enable the expression and testing of the *Marinobacter aquaeoli* VT8 2220 gene (Maqu_2507, amino acid sequence provided as SEQ ID NO:11; Genbank Accession ABM19582; GI:120325267; gene sequence provided as SEQ ID NO:12). This gene was cloned into plasmid pUC19 to form pSGI-2507.

Another vector was constructed to enable the expression and testing of the *Arabidopsis thaliana* Fatty acyl-CoA reductase gene CER4 (At4g33790; Genbank Accession: AAL15288.1 GI:16323107), in combination with the *Escherichia coil* str. K-12 substr. W3110 long chain acyl-CoA synthetase gene FadD (Accession: ABO70249.1; GI:134290117), both codon-optimized for expression in *Synechocystis* sp. PCC6803. The nucleotide sequence of this FadD/CER4 functional operon is provided in SEQ ID NO:13. This operon was placed between the EcoRI and SacI restriction sites of plasmid pUC19 to form pSGI-BL77, and between the NcoI and BamHI restriction sites of the plasmid YC79 to form pSGI-BL86.

A *Synechocystis* sp. PCC 6803 codon usage table was utilized to codon optimize the coding region for the *C. carthagenensis* Cc1fatB1 thioesterase gene having a substrate preference for C14 and C16 fatty acids (SEQ ID NO:14). The synthetic gene constructs for expression of the higher plant thioesterase gene were made with a truncation of the 5' end to exclude the predicted plastid transit peptide-encoding region at the amino-terminus. The codon-optimized Cc1FatB1 gene was synthesized by DNA2.0 (Menlo Park, Calif.) and was cloned into a *Synechocystis* sp. PCC 6803 integration vector pSGI-YC28. pSGI-YC28 contains the modified trc promoter from pTrcHisA (Invitrogen, Carlsbad, Calif.). The Cc1FatB1 gene was subcloned into pACYC184 vector at the BamHI site to form vector pAC/1A using the InFusion system (Clontech, Mountainview, Calif.). The sequence of the protein encoded by the Cc1FatB1 gene is provided in SEQ ID NO:15.

Example 7

Production of Fatty Alcohol in *E. coli*

Electro-competent *E. coli* K19 cells were co-transformed with 100 ng pAC/1A (cc1fatB1 thioesterase construct) and 100 ng BL76 by electroporation. Transformants were inoculated into 5 mL LB medium containing chloramphenicol (30 mg/L) or/and spectinomycin (50 mg/L) as appropriate on a rotary shaker (200 rpm) at 30° C. overnight. Overnight cultures were inoculated in LB medium to obtain 50 mL of culture having an initial culture $OD_{730\ nm}$ of 0.15-0.25. When the $OD_{600\ nm}$ was greater than 1.0, 50 uL 1M IPTG was added for induction. The entire 50 mL culture was collected 24 hr post inoculation and treated with 0.2 mg/mL lysozyme and 2 mM EDTA for 1 hr at 30° C. Cell debris was removed by centrifuging the cell lysate at 3000×g for 10 min. The supernatant was collected and extracted by mixing with methylene chloride at a 1:1 ratio (vortexed for 1 min). The mixture was centrifuged at 1800 g for 10 min and the organic layer was transferred to a clean glass tube and concentrated in vacuo to 1.5 mL. The pellet was resuspended in 10 ml $H_2O$ and extracted by mixing with 40 ml methylene chloride (vortex 1 min, incubate at room temperature for 1 hr, and vortex for an additional minute).

The constructs BL71, BL73, BL86, and 2507 were individually co-transformed with 100 ng pAC/1A (cc1FatB1 thioesterase construct) into electrocompetent *E. coli* K19 cells by electroporation. Transformants were inoculated into 5 mL LB medium containing chloramphenicol (30 mg/L) or/and spectinomycin (50 mg/L) or, in the case of the 2507 construct, carbenicillin (100 mg.ml) as appropriate, on a rotary shaker (200 rpm) at 30° C. overnight. Overnight cultures were inoculated in LB medium to obtain 50 mL of culture having an initial $OD_{730\ nm}$ of 0.15-0.25. After 2 hr of cultivation, 50 uL 1M IPTG was added for induction. A volume of 50 mL culture was collected 24 hr post inoculation. The cell pellets were resuspended in 5 ml $H_2O$ and extracted by mixing with 25 ml methylene chloride (vortexing for 1 min with 450-600 µm glass beads, incubated at room temperature for 1 hr, and vortexed for an additional minute). The extraction mixture was centrifuged at 1800×g for 10 min and transferred to a clean glass tube. The organic layer was concentrated in a nitrogen stream to 1 mL. Products were analyzed in Example 8.

Example 8

Gas Chromatographic Analysis of Fatty Alcohols Produced by Transformed *E. coli* Strains The samples for analysis were prepared by adding 50 uL of 5 mM 1-hexanol in methylene chloride (used as an internal standard) to 500 uL of the sample being tested. The sample was then analyzed by GC/MS.

Fatty acids were analyzed by adding internal standards, sulfuric acid, sodium chloride, and hexane to culture aliquots, and subjecting the mixtures to vigorous vortexing. After centrifugation, the organic phase was transferred to a GC vial and analyzed on an Agilent model 7890A gas chromatograph equipped with an FID (flame ionization detector).

An Agilent 7890A gas chromatograph with a J&W Scientific HP-5MS capillary column (30 m length, 0.25 mm internal diameter, 0.25 µm film thickness) coupled to an Agilent 5975C mass spectrophotometer was used for analysis. The GC oven was programmed as follows: 90° C. for 0.5 min., then heated at 20° C./min. to 285° C. The injector temperature was kept at 280° C., and a 5:1 split injection was used. Helium was used as a carrier gas at a flow rate of 1.2 mL/min. The analytes were identified by comparison to injected standard compounds, as well as by use of the Wiley mass spectral library. The limit of quantitation for the analytes was 5 uM.

Spiking and recovery experiments show that the extraction method recovers about 80% of each analyte.

Figure 2A:
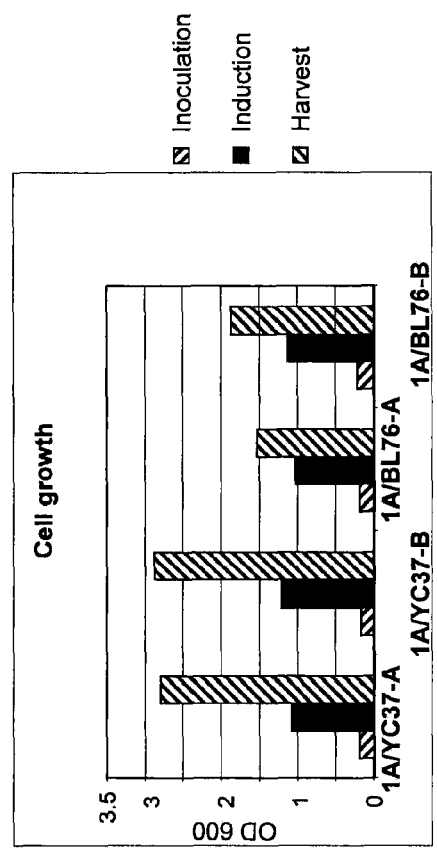
FIG. 2A is a graph showing the growth ($OD_{600}$) of strains transformed with various expression construct operons as provided in Example 6.: 1A/YC37-A and 1A/YC37-B are E. coli K19 isolates carrying an empty vector; 1A/BL76-A and 1A/BL76-B are E. coli K19 isolates that included the FadD-luxC operon.
Figure 2B:
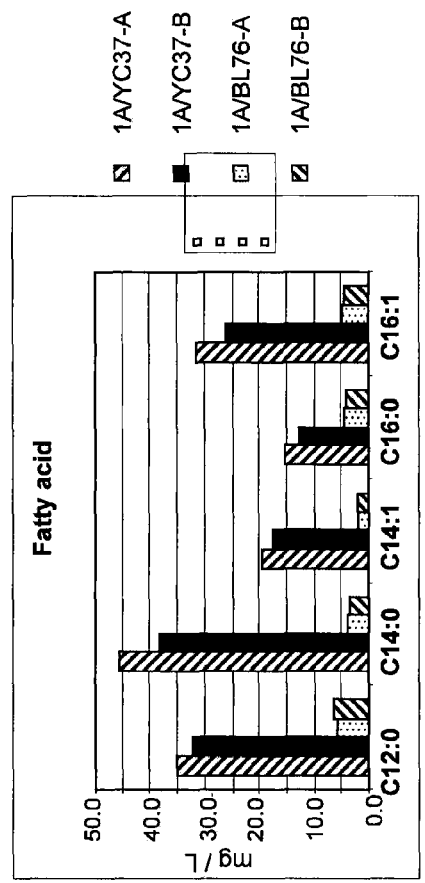
FIG. 2B is a graph providing the amount of fatty acids produced by the strains (mg/ml).
Figure 2:
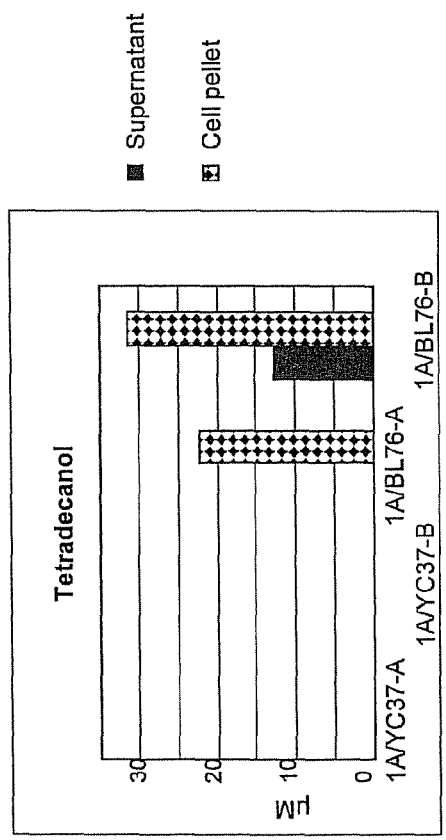
FIG. 2 illustrates the production of fatty alcohols and fatty acids by E. coli strains transformed with an luxC acyl-CoA reductase gene in combination with an acetyl-CoA synthetase gene.
Figure 2:
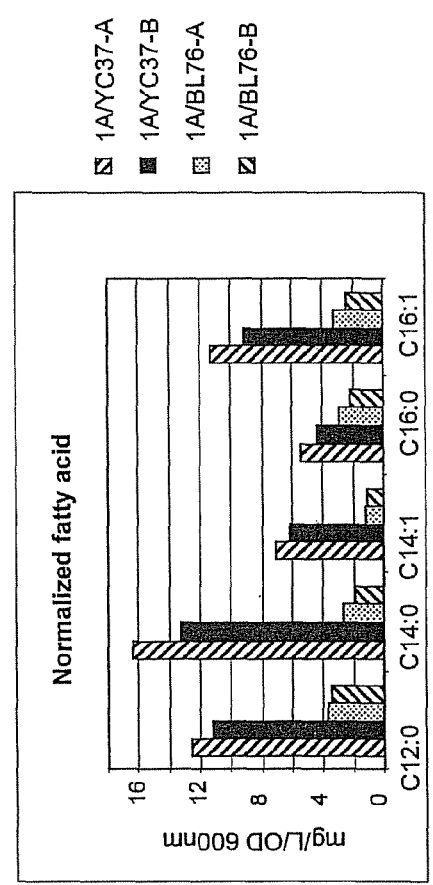

The growth of the strains is compared in FIG. 2A, which depicts less growth of the Maqu 2220 strains after induction. FIG. 2B shows that the Maqu strains accumulate less fatty acid. Production of tetradecanol by isolates that included the Cc1FatB1 thioesterase together with the FadD-LuxC operon (1A/BL76-B) is compared with fatty alcohol production by isolates transformed with only the Cc1FatB1 thioesterase gene construct (1A/YC37) in FIG. 2C. The figure demonstrates production of tetradecanol only in the strains that included a fatty acyl reductase (Lux C) together with an exogenous thioesterase, and not in the strain that included only the exogenous thioesterase.

Cell growth and alcohol production by strains transformed with various known or putative alcohol-forming fatty acyl reductases is depicted in FIG. 3A and FIG. 3B, respectively. Two of the tested strains, 1A/BL73, having the Maqu_2220 fatty alcohol-forming reductase in combination with the FadD acyl-CoA synthetase and the Cc1FatB1 thioesterase, and 1A/2507, having the Maqu_2507 acyl-CoA reductase in combination with the Cc1FatB1 thioesterase, produced tetradecanol and hexadecanol, with 1A/BL73 isolates producing some dodecanol as well. The chain lengths of the fatty alcohols produced reflected the substrate preference of the exogenous thioesterase.

Example 9

Alcohol Production by Strains That Include the Maqu_2220 Acyl-CoA Reductase in Combination With Aldehyde-Producing Acyl CoA Reductase Gene To assess the production of ethanol by a strain transformed with the Maqu_2220 gene in addition to an aldehyde-producing reductase gene, the Maqu_2220 gene was introduced into a strain along with genes encoding aldehyde-generating reductase proteins of the *Photorhabdus luminescens* lux operon, and alcohol production was compared with the alcohol production of a strain having the Lux acyl-CoA reductase genes but lacking Maqu_2220. The first construct contained the *Photorhabdus luminescens* fatty acid reductase (luxC, Genbank accession: M90093) and acyl protein synthetase (luxE, Genbank accession: M90093) genes codon-optimized for expression in *Synechocystis* sp. PCC6803 (SEQ ID NO:16). In a second construct, the LuxC-LuxE genes were followed by the *Marinobacter aquaeoli* VT8 2220 gene (Maqu_2220, Genbank Accession ABM19299; GI: 120324984), codon-optimized for expression in *Synechocystis* sp. PCC6803 The nucleotide sequence of this functional operon is provided in SEQ ID NO:17. The plasmid pSGI-BL69 was constructed by inserting the operon between the NcoI and BamHI restriction sites of the vector YC79, which contains the trcY promoter, the lacI$^q$ gene, and homology arms that enable integration of the expression cassette into the "RS2" site of the *Synechocystis* sp. PCC 6803 genome (Aoki, et al., *J. Bacteriol* (1995) 177:5606-5611).

Electro-competent *E. coli* K27 cells that included an exogenous Cc1FatB1 gene were co-transformed with 100 ng BL87 (trcY:luxC-luxE) and 100 ng BL88 (trcY:luxC-luxE-MAqu_2220) by electroporation and transformants were selected, cultured, induced for expression of the introduced genes, and analyzed for alcohol production using GC as described in the Examples 7 and 8, above, except that the was concentrated to 1 ml.

Figure 3:
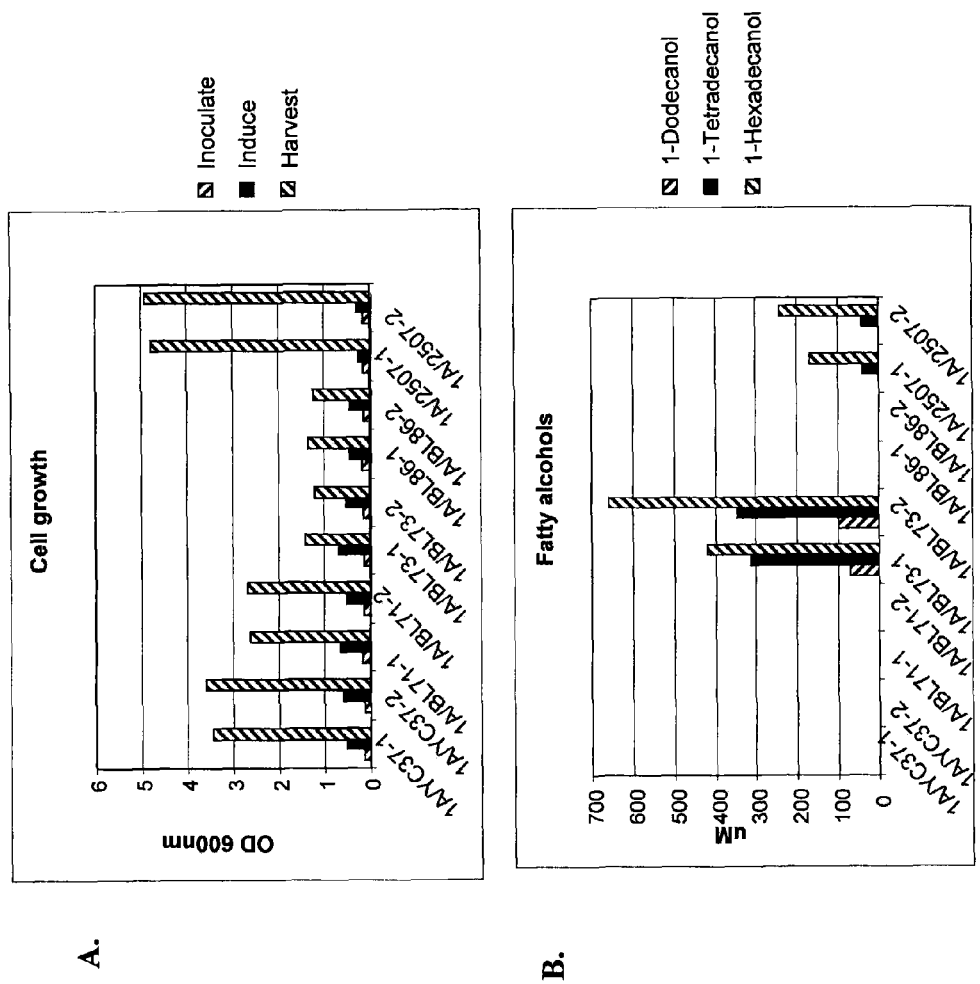
FIG. 3 depicts fatty alcohol production by E. coli cells transformed with acyl-CoA reductase genes in combinations with other genes.
Figure 4:
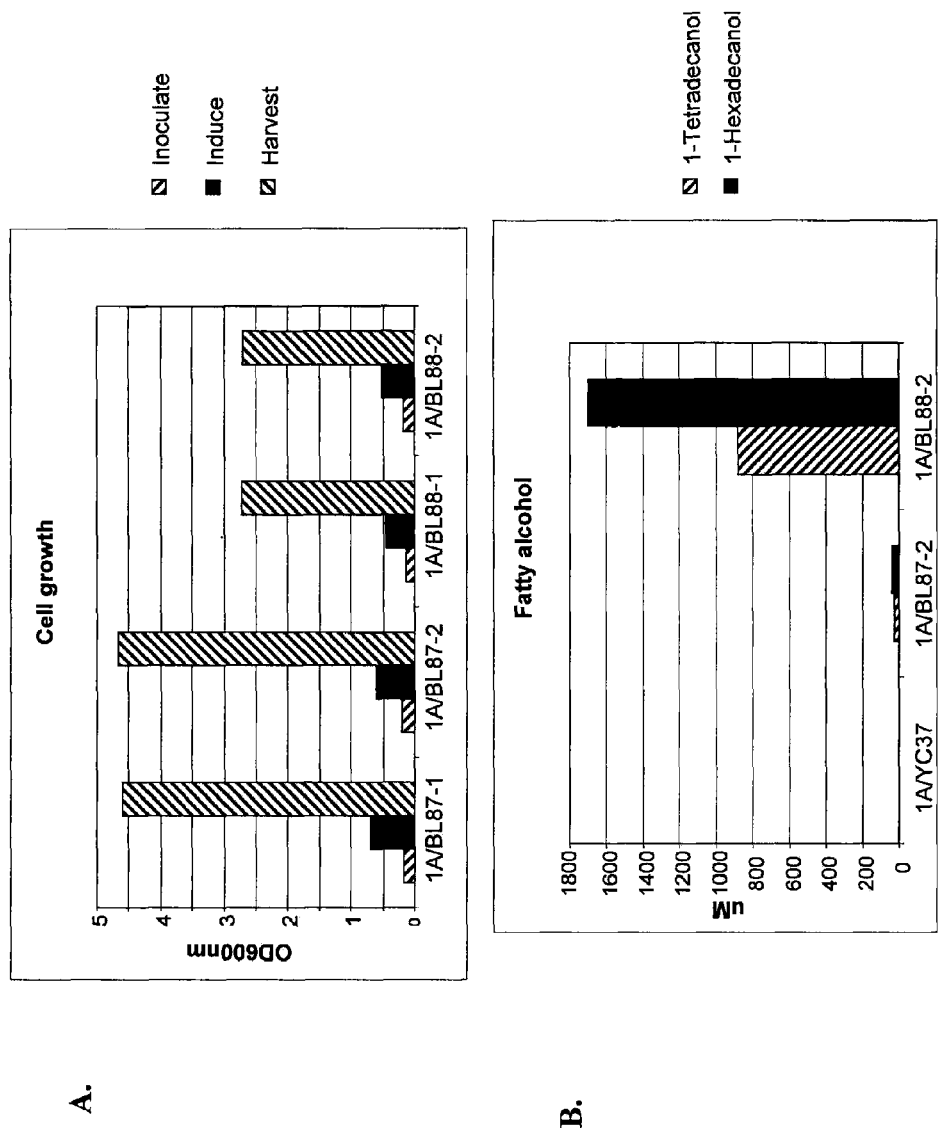
FIG. 4 depicts production of fatty alcohol by E. coli strains transformed with the Maqu 2220 gene in combination with lux genes.

The results are depicted in FIG. 4. The strain that included only the luxC and luxE genes (reductase and acyl protein synthetase of the lux acyl-ACP reductase complex), in combination with a thioesterase gene, made negligible amounts of alcohol. When Maqu_2220 was expressed in combination with luxE, luxC, and a thioesterase, however, significant amounts of alcohol were produced, indicating that Maqu_2220 is an alcohol forming acyl-CoA reductase. The amount of alcohol produced by Maqu_2220 in combination with the aldehyde forming acyl-CoA reductases lux E and lux C exceeds the amount of alcohol made by Maqu_2220 in the absence of an aldehyde-forming reductase (comparing 1A/BL88-2 of FIG. 4B with 1A BL73-2 in FIG. 3B), even when taking into account the better growth of the BL88-2 strain (FIG. 4A compared with FIG. 3A).

Example 10

Production of Fatty Alcohol in the Cyanobacterium *Synechocystis*

A construct similar to that used in the previous example that included the luxE gene, the luxC gene, and the Maqu_2220 alcohol-forming acyl-CoA reductase was transformed into Synechocystis sp. PCC6803 cells that included an integrated exogenous Cc1FatB1 gene (strain 1 B). As a control, the same acyl-CoA reductase synthetic operon was transformed into *Synechocystis* sp. PCC6803 cells lacking an exogenous thioesterase gene. As a further control, the *Synechocystis* strain that included the integrated exogenous Cc1FatB1 gene was included in the experiments as well. Transformation, culturing, and induction of strains were as described in Example 4.

The samples were analyzed for the production of fatty alcohols by the three transgenic *Synechocystis* strains as well as the wild-type strain (control) using standard gas chromatographic methods as provided in Example 3, except that 25 mls of culture was concentrated to 1.5 ml of methylene chloride extract. Fatty acids were analyzed by adding internal standards, sulfuric acid, sodium chloride, and hexane to culture aliquots, and subjecting the mixtures to vigorous vortexing. After centrifugation, the organic phase was transferred to a GC vial and analyzed on an Agilent model 7890A gas chromatograph equipped with an FID (flame ionization detector).

Figure 5:
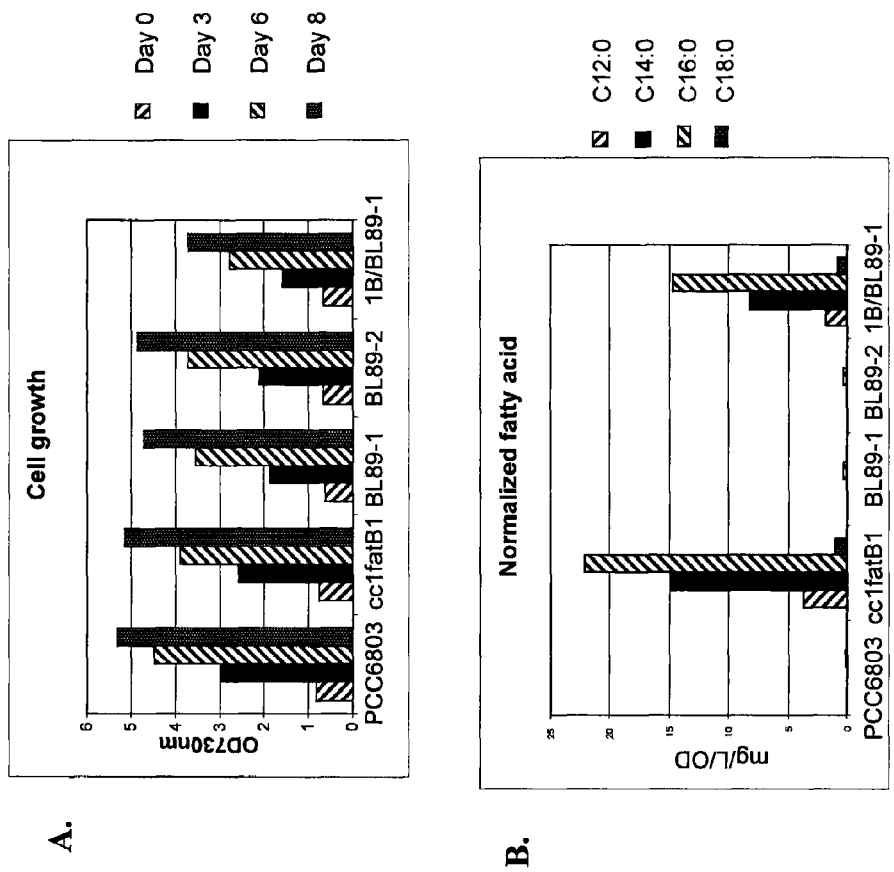
FIG. 5 depicts alcohol production by a photosynthetic microorganism transformed with the Maqu 2220 gene in combination with lux C and E genes.
Figure 5:
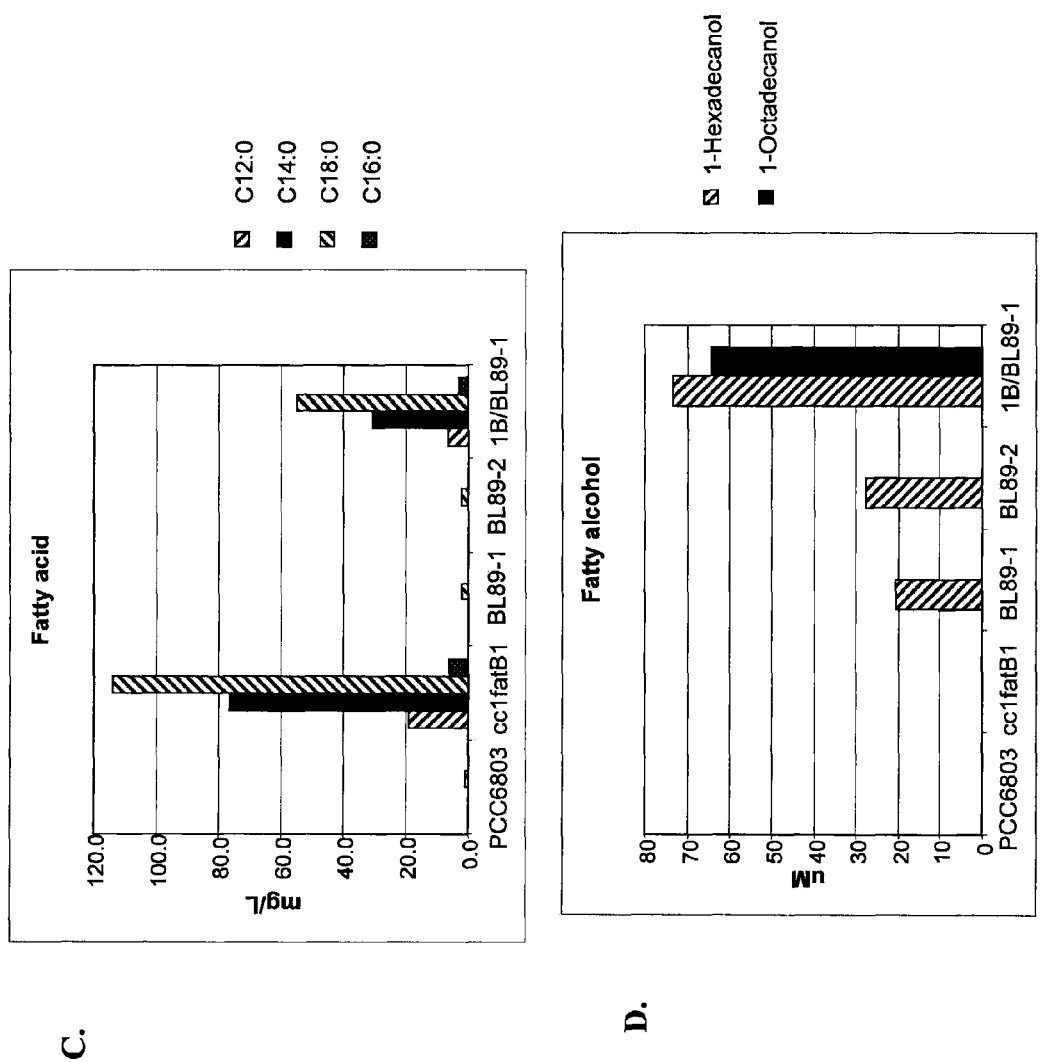
Figure 6A:
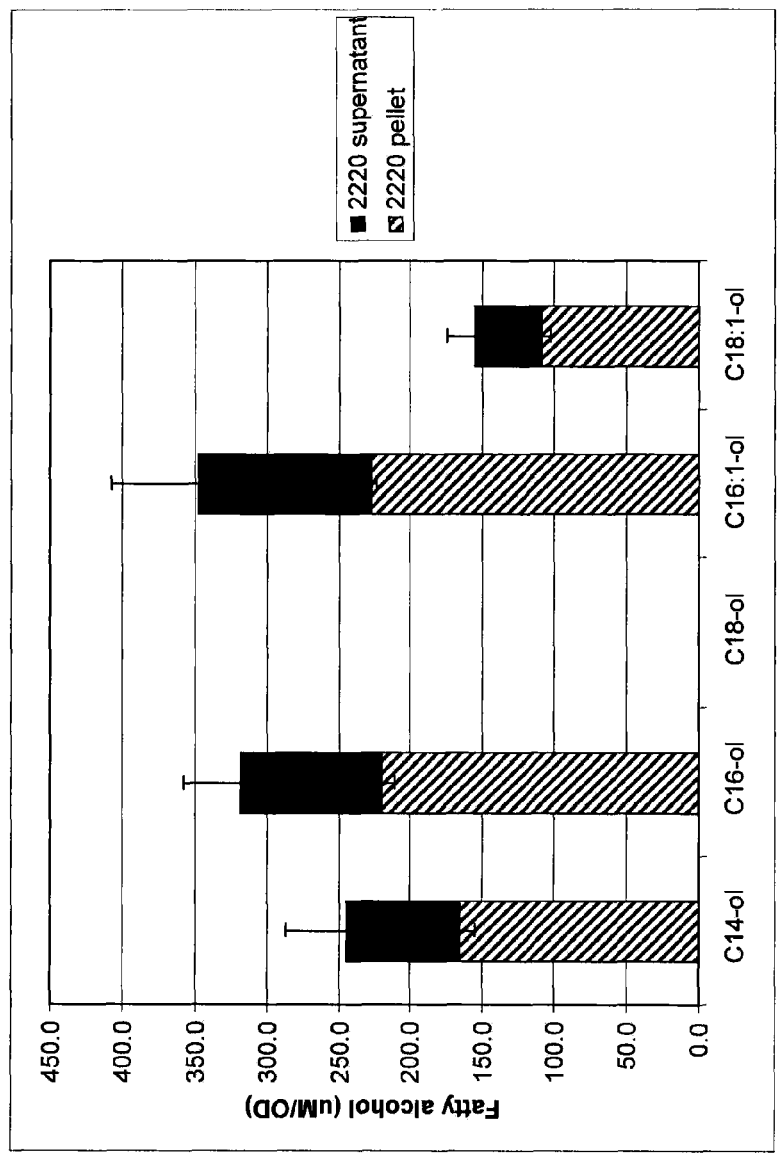
FIG. 6A provides a graph of the cell/supernatant distribution of fatty alcohols produced by the Maqu2220 gene-bearing strain analyzed in Example 11.
Figure 6B:
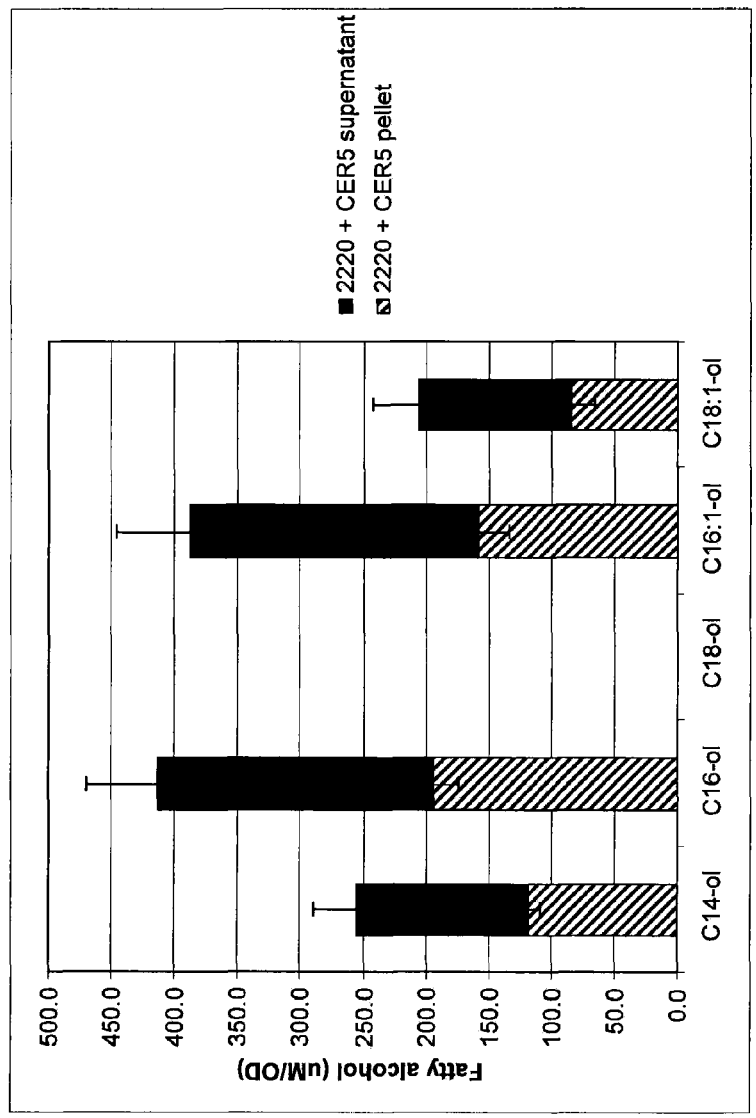
FIG. 6B provides a graph of the cell/supernatant distribution of fatty alcohols produced by the Maqu 2220 gene+CER5 gene-bearing strain analyzed in Example 11.
Figure 6C:
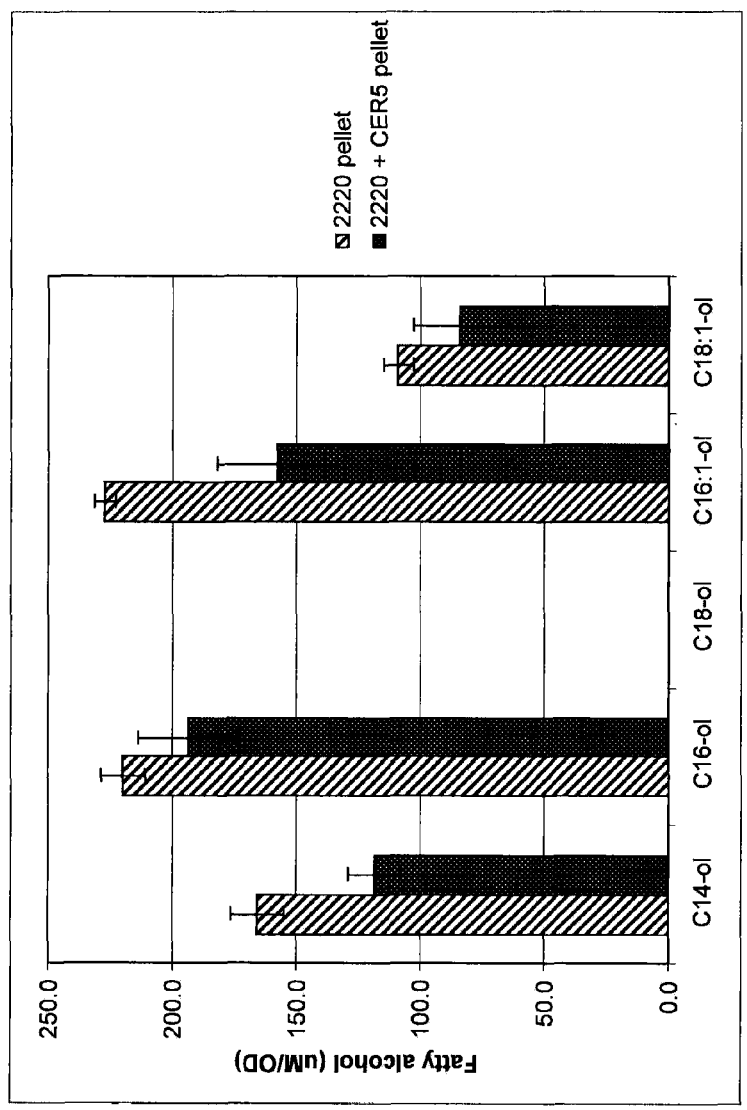
FIG. 6C provides a graph comparing the amounts of fatty alcohols detected in the cell pellets of strains having the Maqu 2220 gene versus strains having the Maqu 2220 gene+CER5 gene.
Figure 6D:
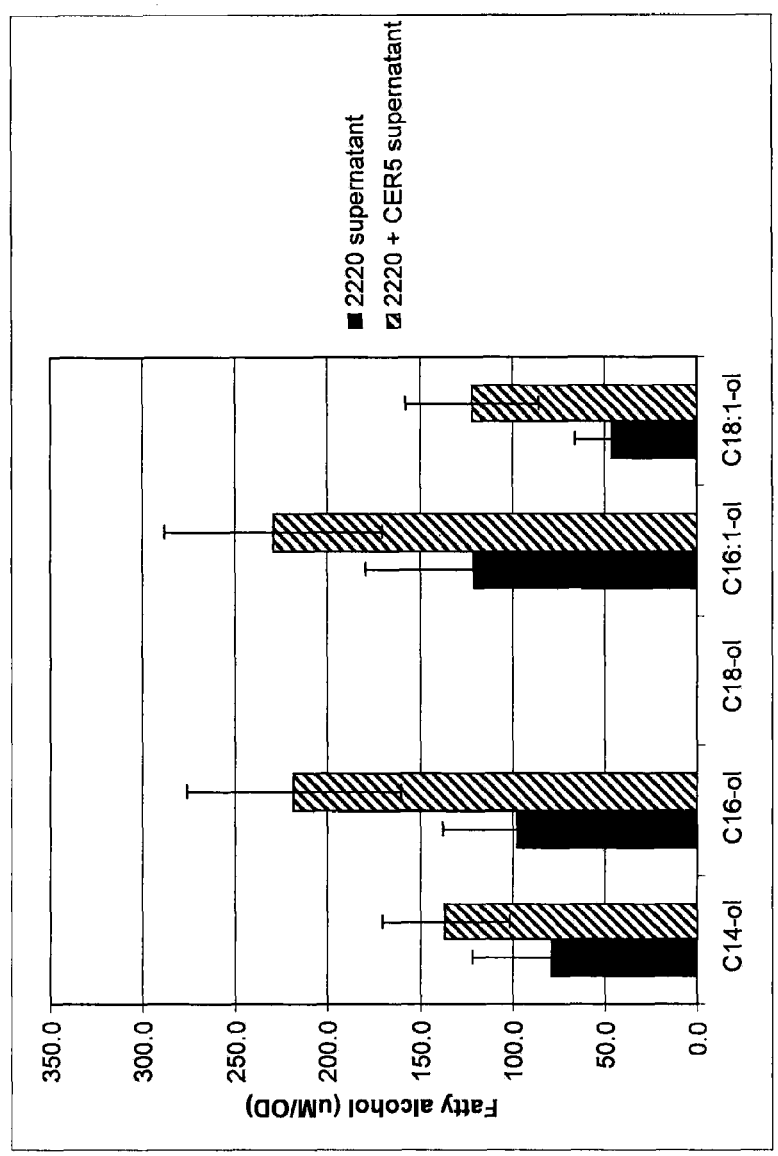
FIG. 6D provides a graph comparing the amounts of fatty alcohols detected in the culture supernatants of strains having the Maqu gene versus strains having the Maqu 2220 gene+CER5 gene.

FIG. 5 shows that the strain including the exogenous thioesterase gene Cc1FatB1 produces fatty acids (FIG. 5C) but not detectable fatty alcohol (FIG. 5D). The SL89 strain that includes the luxC-luxE-Maqu_2220 operon but does not include a thioesterase does not accumulate free fatty acids (FIG.5C), but does produce some hexadecanol (FIG. 5D). By contrast, strain 1B/BL89-1, including an exogenous thioesterase and the luxC-LuxE-Maqu_2220 operon produces significant amounts of both hexadecanol and octadecanol (FIG. 5D).

Example 11

Alcohol Production by Strains Expressing the Maqu_2220 Fatty Aldehyde Reductase Gene and a Transporter Gene Further experiments were conducted to test the productivity of strains that included an acyl-CoA reductase gene and a transporter for exporting the fatty alcohol into the media. A vector including the Maqu_2220 gene (SEQ ID NO:9) was transformed into *E. coli* K19 cells in the absence of a transporter gene, and in a separate transformation was introduced into *E. coli* K19 cells together with a vector including the *Arabidopsis thaliana* CER5 gene (Accession number AAU44368; GI:52354014; SEQ ID NO:19) encoding an ABC transporter.

Electro-competent *E. coli* K19 cells were co-transformed with 100 ng pAC/CER5 and 100 ng pUC/ Maqu2220 by electroporation. Transformants were inoculated from a colony on a plate into 5 mL LB medium containing chloramphenicol (50 mg/L), carbenicillian (100 mg/L) and 1 mM IPTG, and grown on a rotary shaker (200 rpm) at 30° C. for 24 hrs. The entire 5 mL culture for each sample was centrifuged for 5 mins at maximum speed. The supernant was collected in a fresh flask to which 7.5 mL of methylene chloride was added and the mixture was vortexed. The mixture was then allowed to separate and the organic bottom layer was collected and put into a 20 mL scintillation vial. For the pellet, 5 mL of methylene chloride was added along with 2.5 mL of $H_2O$ and glass beads. The sample was then vortexed until the cells lysed. The sample was then centrifuged for 5 min at maximum speed and the organic bottom later was collected in a scintillation vial. The organic layers (from supernant and pellet) were concentrated by flushing with nitrogen and once dried 1 mL of methylene chloride was added, the samples were vortexed and then added to 1 mL GC vial.

The production of fatty alcohol by the strains is depicted in FIG. 6. There is a significant increase in the amount of fatty alcohol exported into the media when CER5 is present, indicating that this protein is able to transport fatty acids out of the cells. Surprisingly, expression of the CER5 gene in cells expressing a Maqu_2220 gene also leads to greater overall production of alcohols by the cells (approximately 16% more alcohol produced by cells having the CER5 gene over a 24 hour period).

Example 12

Expression of Additional Fatty Alcohol Pathway Genes

Genes having at least 40% identity to the amino acid sequence of the protein encoded by the *Marinobacter aquaeoli* VT8 2220 gene (SEQ ID NO:9)were identified by BLAST searching of the NCBI public database (blast.ncbi.nlm.nih.gov/). The following genes were identified: *Marinobacter algicola* DG893, Accession ZP_01892457; SEQ ID NO:21 (77% amino acid identity); *Hahella chejuensis* KCTC 2396 HCH_05075; Accession YP_436183, Gene ID 3837725 (55% amino acid identity) SEQ ID NO:23; *Oceanobacter* sp. RED65 ZP_01305629, gb EAT13695 (44% amino acid identity) SEQ ID NO:25. In addition, another *Marinobacter aquaeoli* VT8 2220 gene, Maqu_2507 (SEQ ID NO:27), was identified as a possible fatty acyl-CoA reductase or fatty aldehyde reductase. These genes were synthesized and cloned into expression constructs for determine whether their expression resulted in alcohol production.

*E. Coli* K19 cells were transformed with constructs that included the *Oceanobacter* sp. RED65, the *Hahella chejuensis* KCTC 2396 gene, and the Maqu_2507 gene as described above. Transformants were cultured and analyzed for fatty alcohol production as described in the previous example.

Figure 7:
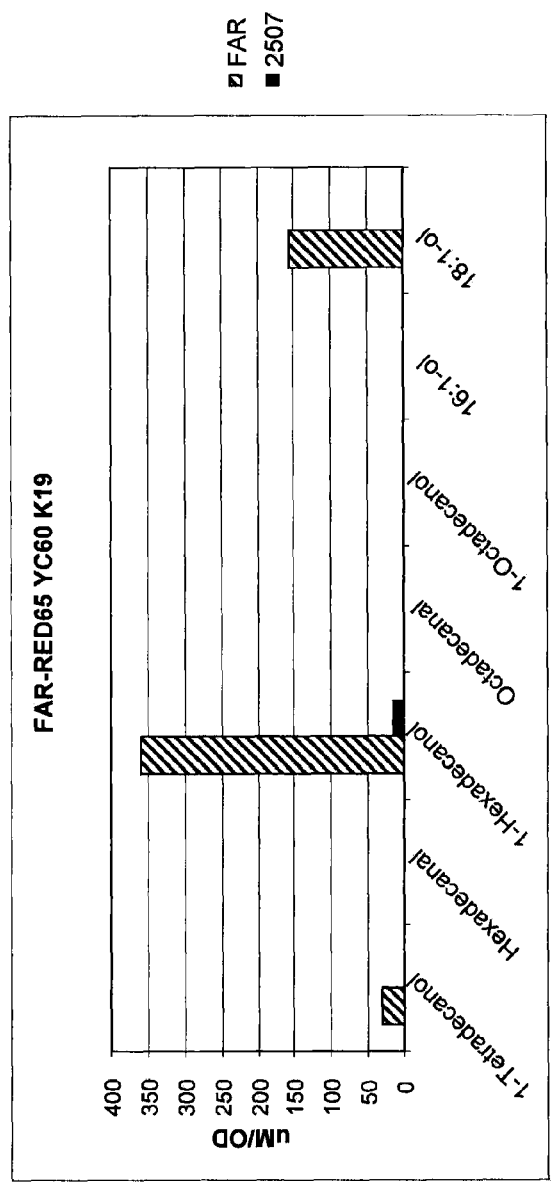
FIG. 7 is a graph depicting the amount of fatty alcohols produced by an *E. coli* strain having the FAR gene of *Oceanobacter* sp. RED65 and a strain having the Maqu 2507 gene.
Figure 8:
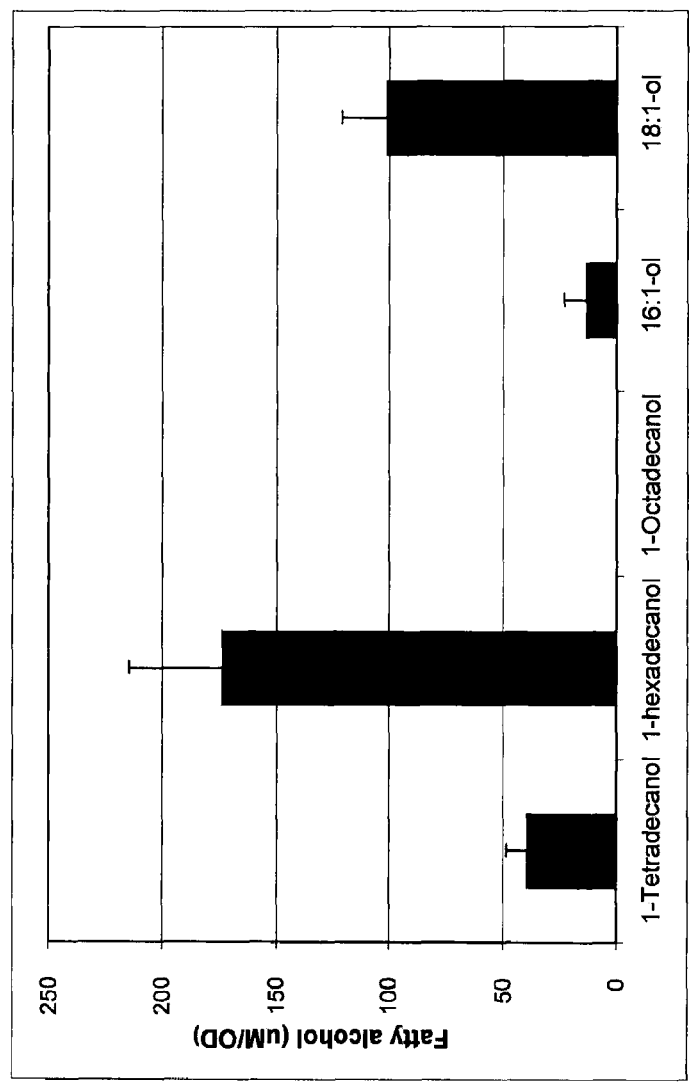
FIG. 8 is a graph depicting fatty alcohol production by an *E. coli* strain carrying the HCH 05075 gene.
Figure 9A:
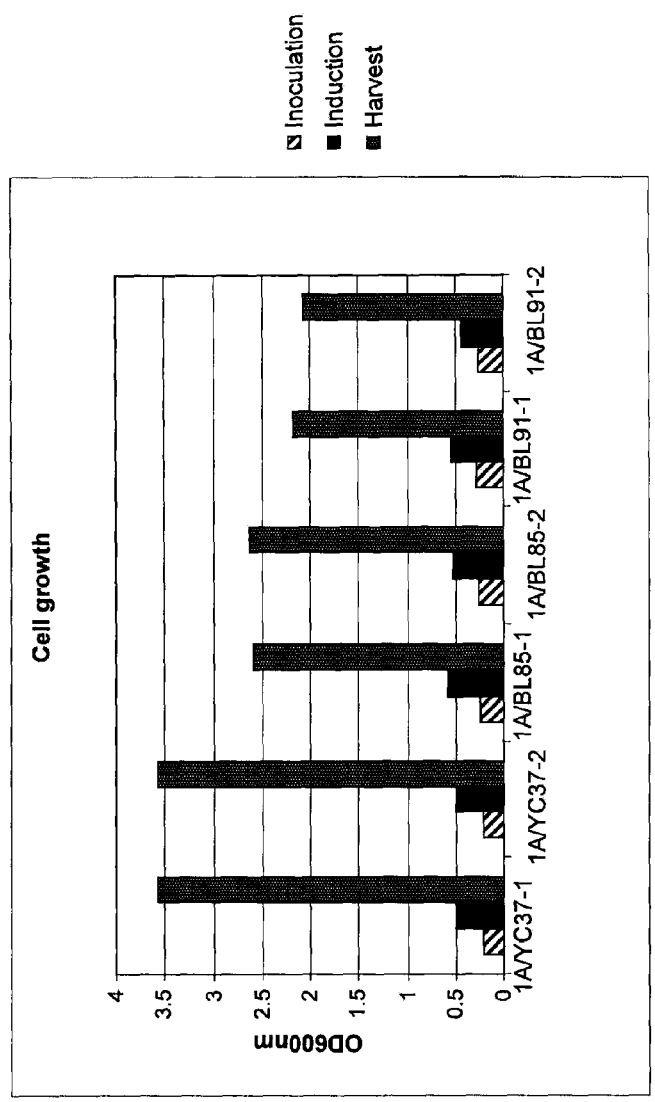
FIG. 9A is a graph depicting the growth of *E. coli* cells having an empty vector a Cc1FAtB1 gene (1A/YC37), cells having a thioesterase gene and a FadD/truncated FAR6 operon, and cells having a thioesterase gene and a FadD-FAR4 operon.
Figure 9B:
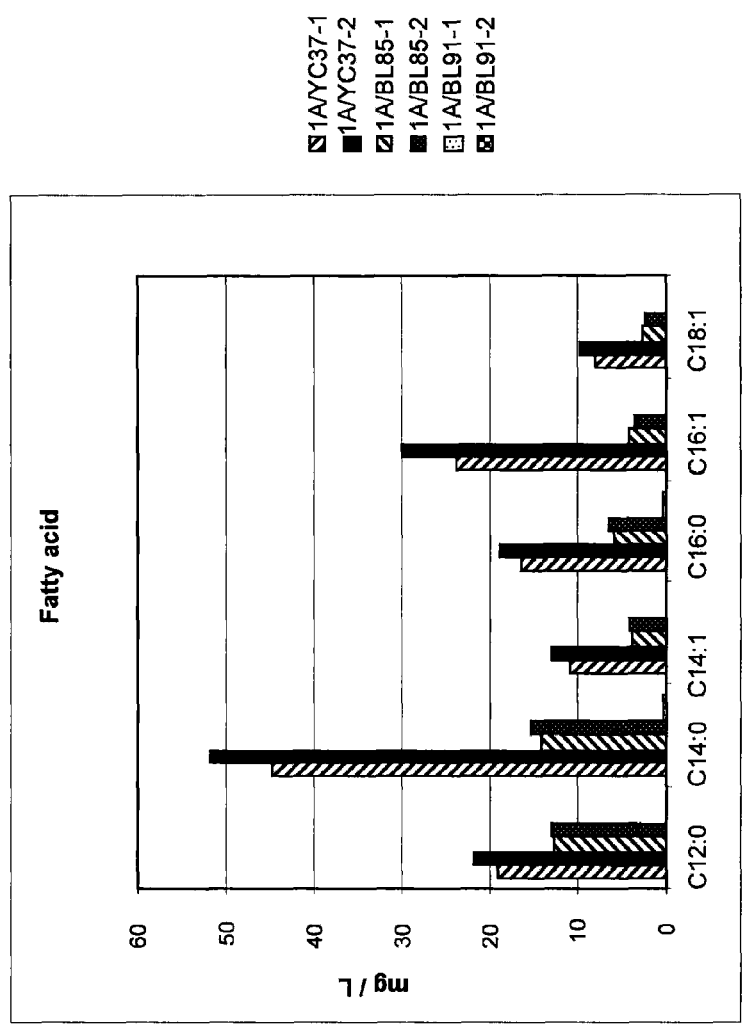
FIG. 9B is a graph depicting fatty acid production by the strains.
Figure 9C:
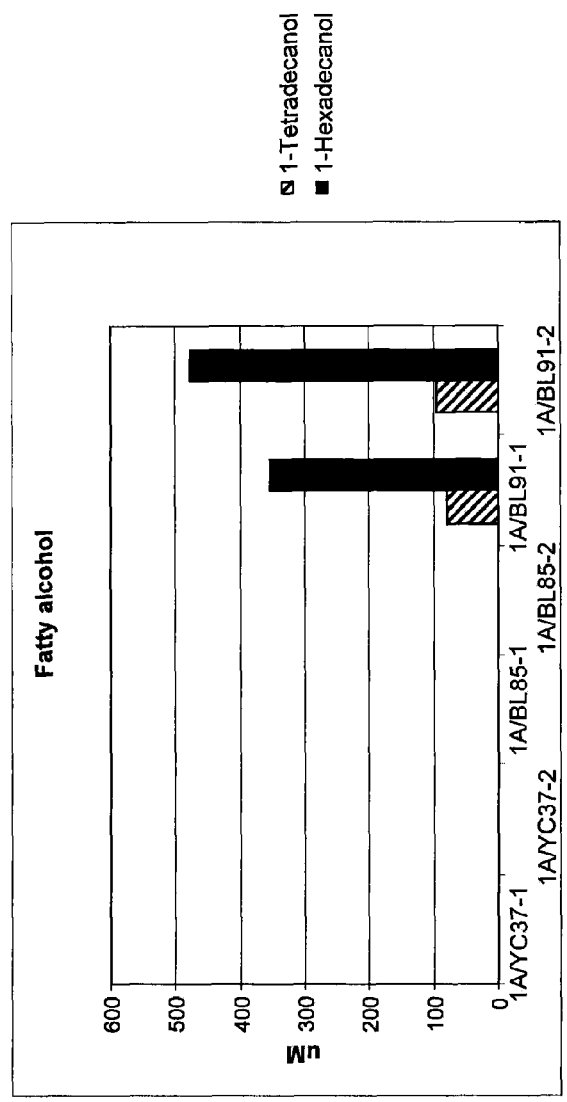
FIG. 9C is a graph depicting fatty alcohol production by the strains.
Figure 9D:
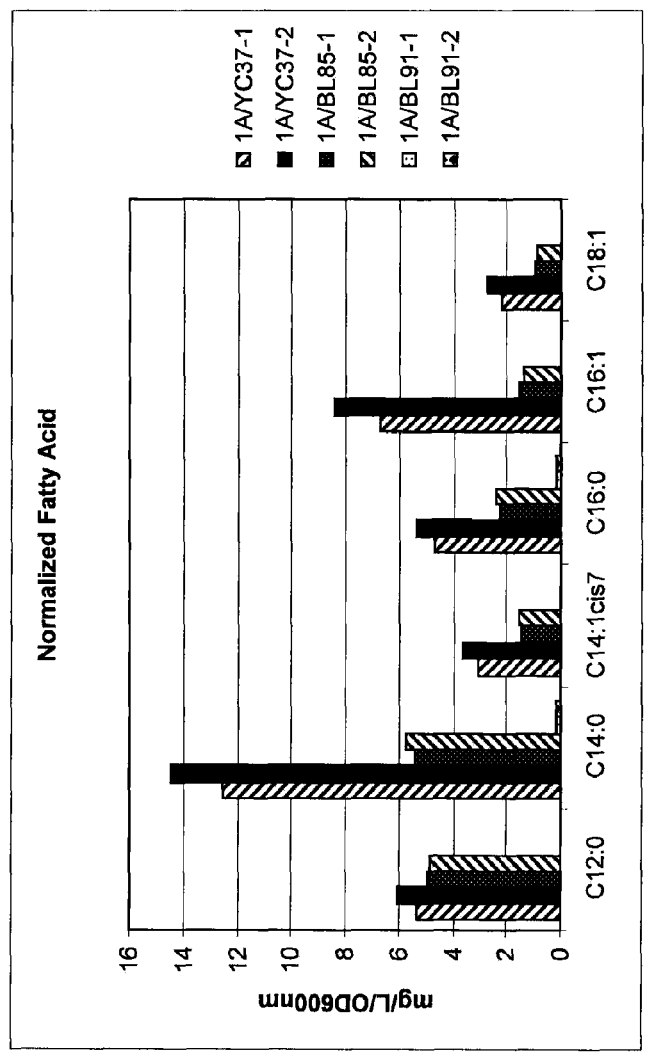
FIG. 9D is a graph depicting the fatty acid produced by the strains, normalized to OD.

The results showed that expression of both the *Oceanobacter* sp. RED65 ZP_01305629 genes and the Maqu_2507 gene (shown in FIG. 7) resulted in alcohol production by the cells, indicating that these genes are alcohol-forming reductases. FIG. 8 shows that the recombinant host cells expressing the HCH 05075 gene also produced alcohol, indicating that it too is a fatty alcohol-forming reductase.

Example 13

Expression of a Truncated Eukaryotic Acyl-CoA Reductase

A vector was constructed to enable the expression and testing of an *Escherichia coli* str. K-12 substr. W3110 long chain acyl-CoA synthetase gene (FadD, NCBI reference No. YP_001724804.1) in combination with a truncated *Arabidopsis thaliana* fatty acyl-CoA reductase gene (FAR6, Swiss-Prot: B9TSP7.1; Accession NM_15529, GI: 18410556), codon-optimized for expression in *Synechosytis* PCC6803. The nucleotide sequence of the FadD/truncated FAR6 functional operon is provided in SEQ ID NO:29. This operon was placed between the NcoI and BamHI restriction sites in the plasmid YC79 to form pSGI-BL91.

The N-terminal truncation was based on an alignment of the amino acid sequence of the Maqu 2220 protein with known or putative eukaryotic fatty acyl-CoA reductases. When the amino acid sequences were aligned, it was recognized that some eukaryotic fatty acyl-CoA reductases had N-terminal regions having no significant homology with the Maqu 2220 amino acid sequence. The N-terminal regions of two such eukaryotic fatty acyl-CoA reductases, FAR6 and *Arabidopsis* MS2 (Accession ABZ10952; GI: 167077486, native protein sequence provided as SEQ ID NO:30), were truncated to provide genes encoding N-terminally truncated FAR6 (SEQ ID NO:28) and N-terminally truncated MS2 (protein sequence provided as SEQ ID NO:31).

Electro-competent *E. coli* K19 cells were co-transformed with 100 ng pAC/1A(cc1fatB1) and 100 ng BL85, a construct that included the *E. coli* FadD gene and the *Arabidopsis* FAR4 gene (Accession AL353818, GI: 7635467) for the truncated FAR6 fatty acid reductase gene (SEQ ID NO:29) or BL91 by electroporation. Transformants were inoculated into 5 mL LB medium containing chloramphenicol (30 mg/L) or/and spectinomycin (50 mg/L) as appropriate on a rotary shaker (200 rpm) at 30° C. overnight. Overnight cultures were inoculated in LB medium to obtain 50 mL of culture having an initial culture $OD_{730 nm}$ of 0.15-0.25. After 2 hr, 50 uL 1M IPTG was added for induction. A volume of 50 mL culture was collected 24 hr post inoculation. Cell pellets were resuspended in 5 ml $H_2O$ and extracted by mixing with 25 ml methylene chloride (vortexing for 1 min with 450-600 µm glass beads, incubated at room temperature for 1 hr, and vortexed for an additional minute). The extraction mixture was centrifuged at 1800 g for 10 mins and organic layer was transferred by pasture pipet into a clean glass tube. The organic layer was concentrated in nitrogen stream to 500 ul. Fatty acids were analyzed by adding internal standards, sulfuric acid, sodium chloride, and hexane to culture aliquots, and subjecting the mixtures to vigorous vortexing. After centrifugation, the organic phase was transferred to a GC vial and analyzed on an Agilent model 7890A gas chromatograph equipped with an FID (flame ionization detector).

FIG. 9 shows that *E. coli* K19 cells transformed with the BL85 construct that includes the FadD gene and a full length FAR4 gene produced no detectable fatty alcohol. By contrast, the BL91 construct that includes the FadD gene and the N-terminally truncated FAR6 gene produced significant amounts of tetradecanol and hexadecanol. This is in contrast to the BL71 construct, described in Example 1 and analyzed in Example 6, that included the FadD gene and a full length FAR6 gene. As seen in FIG. 3, no fatty alcohol was detected in extracts of Cc1FatB1 gene ("1A")-containing *E. coli* K19 cells that were transformed with the full-length FAR6 gene in the BL71 construct.

While the disclosure has been particularly shown and described with reference to several embodiments thereof, it will be understood by those of ordinary skill in the art that various changes in form and details may be made thereto without departing from the principles and spirit of the disclosure, the proper scope of which is defined in the following claims and their equivalents.

The invention claimed is:

1. A recombinant microorganism, comprising:
at least one exogenous gene encoding an N-terminally truncated eukaryotic alcohol-forming fatty acyl-CoA reductase, wherein the eukaryotic alcohol-forming fatty acyl-CoA reductase is an N-terminally truncated FAR6 of *Arabidopsis* (SEQ ID NO:28) or a homolog or variant thereof having at least 65% identity to SEQ ID NO:28, or an N-terminally truncated MS2 of *Arabidopsis* (SEQ ID NO:31) or a homolog or variant thereof having at least 65% identity to SEQ ID NO:31;
wherein the recombinant microorganism produces at least one fatty alcohol.

2. The recombinant microorganism of claim 1, further comprising at least one exogenous thioesterase gene.

3. The recombinant microorganism of claim 1, further comprising at least one exogenous acyl-CoA synthetase gene.

4. The microorganism of claim 1, further comprising at least one exogenous gene encoding a transporter protein.

5. The recombinant microorganism of claim 4, wherein the at least one exogenous transporter protein gene is CER5, WBC11, a gene encoding AtMRPS, AmiS2, or AtPGP 1, or a gene encoding a homolog or variant of a transporter protein having at least 65% identity to the transporter encoded by the CER5 gene, the transporter encoded by the WBC11 gene, AtMRPS, AmiS2, or AtPGP1.

6. The recombinant microorganism of claim 1, wherein the microorganism is a photosynthetic microorganism.

7. The recombinant microorganism of claim 6, wherein the microorganism is a cyanobacterial species.

8. The recombinant microorganism of claim 6, wherein the microorganism is a eukaryotic microalgal species.

9. A recombinant microorganism comprising:
   at least one exogenous gene encoding an N-terminally truncated eukaryotic alcohol-forming fatty acyl-CoA reductase, wherein the N-terminally truncated eukaryotic alcohol-forming fatty acyl-CoA reductase is an N-terminally truncated FAR6 of *Arabidopsis* (SEQ ID NO:28) or a homolog or variant thereof having at least 65% identity to SEQ ID NO:28, or an N-terminally truncated MS2 of *Arabidopsis* (SEQ ID NO:31) or a homolog or variant thereof having at least 65% identity to SEQ ID NO:31;
   wherein the N-terminal truncation of the eukaryotic alcohol-forming fatty acyl-CoA reductase occurs within ten amino acids of the N-terminus of SEQ ID NO: 28 or SEQ ID NO:31 when the sequence of the eukaryotic alcohol-forming fatty acyl-CoA reductase is aligned for maximum homology with SEQ ID NO:28 or SEQ ID NO:31;
   wherein the recombinant microorganism produces at least one fatty alcohol.

10. The recombinant microorganism of claim 5, wherein the at least one exogenous transporter protein gene is CER5 or a gene encoding a homolog or variant of the CER5 transporter having at least 65% identity to the CER5 transporter.

11. The recombinant microorganism of claim 1, further comprising at least one exogenous gene encoding an aldehyde-generating fatty acyl-CoA reductase.

12. The recombinant microorganism of claim 11, wherein the at least one exogenous gene encoding an aldehyde-generating fatty acyl-CoA reductase is an Acr1 gene, an AcrM-1 gene, or one or more of a luxC gene, a luxD gene, or a luxE gene, or a homolog or variant thereof encoding an aldehyde-generating acyl-CoA reductase having at least 65% identity to encoding an aldehyde-generating acyl-CoA reductase encoded by the Acr1 gene, the AcrM-1 gene, a luxC gene, a luxD gene, or a luxE gene.

13. The recombinant microorganism of claim 1, further comprising at least one exogenous carboxylic acid reductase gene.

14. The recombinant microorganism of claim 7, wherein the recombinant microorganism is an *Agmenellum, Anabaena, Anabaenopsis, Anacystis, Aphanizomenon, Arthrospira, Asterocapsa, Borzia, Calothrix, Chamaesiphon, Chlorogloeopsis, Chroococcidiopsis, Chroococcus, Crinalium, Cyanobacterium, Cyanobium, Cyanocystis, Cyanospira, Cyanothece, Cylindrospermopsis, Cylindrospermum, Dactylococcopsis, Dermocarpella, Fischerella, Fremyella, Geitleria, Geitlerinema, Gloeobacter, Gloeocapsa, Gloeothece, Halospirulina, Iyengariella, Leptolyngbya, Limnothrix, Lyngbya, Microcoleus, Microcystis, Myxosarcina, Nodularia, Nostoc, Nostochopsis, Oscillatoria, Phormidium, Planktothrix, Pleurocapsa, Prochlorococcus, Prochloron, Prochlorothrix, Pseudanabaena, Rivularia, Schizothrix, Scytonema, Spirulina, Stanieria, Starria, Stigonema, Symploca, Synechococcus, Synechocystis, Tolypothrix, Trichodesmium, Tychonema,* or *Xenococcus* species.

15. The recombinant microorganism of claim 1, wherein the N-terminally truncated eukaryotic alcohol-forming fatty acyl-CoA reductase is an N-terminally truncated FAR6 of *Arabidopsis* (SEQ ID NO:28) or a homolog or variant thereof having at least 85% identity to SEQ ID NO:28 or an N-terminally truncated MS2 of *Arabidopsis* (SEQ ID NO:31) or a homolog or variant thereof having at least 85% identity to SEQ ID NO:31.

* * * * *

SEQUENCE LISTING

```
<160> NUMBER OF SEQ ID NOS: 31

<210> SEQ ID NO 1
<211> LENGTH: 3091
<212> TYPE: DNA
<213> ORGANISM: Artificial sequence
<220> FEATURE:
<223> OTHER INFORMATION: Synthetic construct: MACS1-FARXIII operon

<400> SEQUENCE: 1 atggccttttt ctcgtgtagg tgcccctcgt tggaatgacc acgacagtcc tgaagagttc      60
aactttgcta gcgatgtgtt agattactgg gcccagatgg aagaagaggg taaacgtggg     120
ccctcccctg ccttttggtg ggttaatggg cagggcgacg agattaagtg gtcttttcgt     180
aagttgcgtg atctgacctg tcggaccgcc aacgttttcg aacagatttg tggtctgcaa     240
caaggcgatc acttagccct gatcttaccc cgcgtacctg aatggtggtt ggtaaccgta     300
ggttgtatgc gcaccgggat tatcttcatg cccggtacca cccagctcaa ggccaaagac     360
attctgtacc gcattcaaat ctcccgtgcg aaagcgatcg ttactaccgc ttccctcgtg     420
cctgaagttg agagcgttgc ctccgaatgt cccgatttga aaaccaaatt ggtagtttcc     480
```

```
gaccacagtc acgaaggttg gttagacttt tgcagcttaa tcaaatccgc tagtcccgat    540
catacttgca tcaaatccaa aatgaaagac ccgatggcca tcttcttcac ctctggtacc    600
actggctacc ccaaaatggc caagcacaac cagggcctcg cttttcggtc ctatatccct    660
tcctgtcgca aactgttgaa actgaaaacc tctgatattc tctggtgtat gagcgatccc    720
ggctggattc tcgctaccgt gggttgtttg attgaacctt ggacctctgg ttgtactgtg    780
tttatccacc acttgccgca atttgacccc aaggtgatcg tggaagtgct cttcaagtac    840
ccgattaccc aatgtctggc tgcccctggc gtctatcgga tggtgctgca acagaaaacc    900
tctaatctcc ggttccccac cttggagcat gcaccaccg ggggtgaaag cttgctgcct    960
gaagaatacg aacagtggaa acaacggact ggcctctcca ttcacgaagt tatgggcag    1020 agcgaaaccg gtattagcag tgctaccttg cgtgaaatga aaatcaaacg gggtagcatt    1080
gggaaagcca tcttgccttt cgacctgcaa atcatcgacg aaaagggcaa tatcttgccc    1140
ccgaataccg agggttacat tggcattcgc atcaaaccga cccgtcccct gggtttgttt    1200
atggaatatg agaattcccc cgaatccacc tctgaagtcg aatgcggtga tttctacaac    1260
tccggtgatc gcgccactat cgatgaagaa ggctacatct ggttcctggg tcgcggggac    1320
gatgtcatca atgcctccgg ttatcgcatt ggtcccgcgg aagtagaaaa cgccctggct    1380
gaacatcccg ccgttgcgga aagtgctgtt gtttcttccc ctgataagga ccgtggcgag    1440
gtcgtgaaag ccttcattgt gctgaatccc gagtttctca gccatgatca agaacaactc    1500
atcaaagaat acaacacca cgtcaaaagc gtaaccgcgc cttacaagta tccccgcaag    1560
gtggaattcg taagtgaact gcccaaaacc gtaaccggga aaatcaagcg taagaattg    1620 cggaacaaag aatttggcca gctctagtaa ctgtcgttaa ctgctttgtt ggtactacct    1680
gacttcaccc tcttttaaga tgtccgccaa cactatggaa accgacgagc aattcactga    1740
caactccccc attgtgaatt tctattccgg taaaagcgtc tttgtgaccg gtgccaccgg    1800
tttcctgggc actgttttag tcgaaaagtt gctgtttagc tgtaaaggca ttaacaacat    1860
ttacatcctc atcaaacaaa ccgaggactt gactattgag gcgcgtattc tgaactatct    1920
gaacagcaaa gccttccatc gtgtcaaaaa caccaacccc gaactcatga aaagattat    1980 ccccatttgc ggcaacctcg aagataagaa tctcgggatt tccgactccg atatgaaaac    2040
cttgttagaa gaagtgagta tcgtctttca cgttgccgcc aagttattgt taagatgtc    2100 cttgaccgct gcggtgaaca tcaacaccaa acccaccgaa cagctcattg ctatttgtaa    2160
gaaaatgcgg cgtaatccca ttttcatcta tgtgagcagt gcctattcca atgtgaatga    2220
acaaatcatt gacgaaaaag tatacaatac cggcgtaccc ttggaaacca tttacgatac    2280
cctggatacc gaaaacaccc ggattaccga catttttcctg acaaacgcc ccaataccta    2340 cacctactcc aaagccctcg ctgaggtggt ggtggaaaaa gaattcgatg aatccgccgc    2400
tattgtgcgg ccctccatca ttgttttctag cattcgggaa ccgatccccg gctggctctc    2460
cggtagtcat ggttttcccc gcgtcgtggg tgccgcttgt aaaggcctgt tgttgcggtg    2520
gcacggcgat ggtaccgttg tttgcgacct gattcccgtc gaccacgttg ccaacttaat    2580
cattgccgct gcttgggaga gcaacgaacg tcggctcatg ggtaacaagg gtgtgaaggt    2640
ctacaactgt tgctccagtt tgcggaaccc catcgacgta atcaccgtcg tgaaaacctg    2700
cattaagtat cgcaaatact tcggtactcg cactatgtct atcttcactc cgcggtttat    2760
catgaagaaa aactatttca tttacaaact cttgtacttc acctgccaca ctattcccgc    2820
tgctatcatt gatggttttct tttggctgac tggccggacc cctatcatgt tgaaaaccct    2880
```

| | |
|---|---|
| cgacaagctg tccaagattt cttccgtttt agaatacttt acccatcatc aattcatttt | 2940 |
| cctggacagt aatgtgcggg gtttgctgcg gcgcatggag ggcaccgatc ggcaaacctt | 3000 |
| taactttgat gtgactgaaa ttgaatggga accctacttg cagaatttcg tgcgtggcat | 3060 |
| tgcgaacaac tacgattact ccatgtagta a | 3091 |

```
<210> SEQ ID NO 2
<211> LENGTH: 3412
<212> TYPE: DNA
<213> ORGANISM: Artificial sequence
<220> FEATURE:
<223> OTHER INFORMATION: Synthetic construct: FadK-FAR6 operon

<400> SEQUENCE: 2
```

| | |
|---|---|
| atggcccatc ccacaggccc gcatctcggg cctgatgttc tgtttcgaga gtccaacatg | 60 |
| aaagtgacat taacgtttaa cgaacaacgt cgtgcggcgt atcgtcagca agggttatgg | 120 |
| ggcgatgctt cgctggccga ttactggcag cagaccgctc gtgcgatgcc agacaaaatt | 180 |
| gccgtggtcg ataatcatgg tgcatcgtac acctatagcg cgctcgatca cgccgcgagc | 240 |
| tgtctggcaa actggatgtt agcgaagggg attgaatcag gcgatcgcat cgcatttcaa | 300 |
| ctgcctggct ggtgtgaatt taccgttatc tatcttgcct gcctgaaaat cggtgcagtt | 360 |
| tccgtgccgc tgttgccttc ctggcgggaa gcagaactgg tgtgggtgct caataagtgt | 420 |
| caggcaaaaa tgttctttgc accgacgttg tttaaacaaa cgcgtccggt agatttaatc | 480 |
| ctgccgctgc aaaatcagct tccacaacta aacaaattg tcggcgtgga caaactggct | 540 |
| cccgccacct cttccctctc attaagtcag attatcgccg acaataccct actgaccacg | 600 |
| gcgataacga cccacggcga tgaattagct gcggtgctgt ttacctccgg aaccgagggt | 660 |
| ctgccaaagg gcgtgatgct aacgcataac aatattctcg ccagtgagcg ggcttattgc | 720 |
| gcgcgactga atctgacctg gcaggatgtc tttatgatgc ctgcgccact tggtcacgca | 780 |
| acgggctttc tgcatggcgt aacggcacca ttcttaattg gcgctcgcag cgtgttgtta | 840 |
| gatattttca ctcctgatgc gtgtctcgcg ctgcttgagc agcagcgttg cacctgtatg | 900 |
| ctcggcgcaa cgccgtttgt ctatgatctt ttgaatgtac tagagaaaca acccgcggac | 960 |
| cttttcagcgc tgcgtttctt tctttgcggc ggaaccacaa tccccaaaaa agtggcgcgt | 1020 |
| gaatgccagc agcgcggcat taaattatta agtgtttatg gttccacaga aagttcgccg | 1080 |
| catgcggtgg tgaatctcga tgatcctttg tcgcgcttta tgcacaccga tggttacgct | 1140 |
| gccgcaggta tagagattaa agtggtcgat gacgcacgca agaccttacc gccaggttgc | 1200 |
| gaaggtgaag aagcctcgcg tggccccaat gtgtttatgg ggtattttga tgaacctgaa | 1260 |
| ttaaccgccc gtgccctgga tgaagaaggc tggtattaca gcggcgatct ctgccgtatg | 1320 |
| gatgaggctg gctatataaa aattaccgga cgcaaaaag atattattgt ccgcggcggc | 1380 |
| gaaaatatta gcagccgtga agtggaagat attttattgc agcatcctaa aattcacgat | 1440 |
| gcctgtgtgg ttgcaatgtc cgatgaacgt ttaggtgaac gatcatgcgc ttatgtcgtg | 1500 |
| ctgaaagcgc cgcatcattc attatcgctg aagaggtag tggctttttt tagccgtaaa | 1560 |
| cgggtcgcaa aatataaata tcctgaacat atcgtggtaa tcgaaaaact accgcgaact | 1620 |
| acctcaggta aaatacaaaa gttttttgtta agaaaagata ttatgcggcg tttaacgcag | 1680 |
| gatgtctgtg aagagattga ataaggatcc tagtaactgt cgttaactgc tttgttggta | 1740 |
| ctacctgact tcaccctctt ttaagatggc caccaccaat gtactggcta cctcccacgc | 1800 |
| cttcaaactg aatggtgtta gctacttttc tagtttcccc cgcaaaccca atcactacat | 1860 |

-continued

```
gcctcgccgt cgtctgtctc acaccacccg ccgtgtccag accagttgtt tctatggcga   1920
aaccagcttc gaggccgtga cctccctggt cacccccaaa actgaaactt cccggaacag   1980
cgatggtatt ggcattgttc ggtttctcga aggtaaatcc tacttggtga ccggtgccac   2040
cggttttctg gccaaagtgc tgattgagaa actgctccgt gagtccctcg aaatcggtaa   2100
gatcttcttg ttgatgcggt ccaaagacca agaaagtgcg aacaagcggc tgtatgatga   2160
gatcatttct tctgatctgt tcaagctcct gaaacaaatg cacggtagct cctatgaagc   2220
ctttatgaag cgcaaactca ttcccgttat tggtgacatt gaagaagata acctcggcat   2280
caaaagtgaa attgctaaca tgatttccga agaaatcgat gtaatcatct cctgtggtgg   2340
tcgcactact tttgacgacc gttatgatag tgctttaagc gtcaatgctt tgggccctgg   2400
ccgtctgttg agcttcggca agggctgccg gaaactcaaa ctcttttttgc acttttccac   2460
cgcctacgtg accgggaaac gcgaggggac tgtgttagaa accccgttat gtattggcga   2520
aaacattacc agtgacttga atatcaaatc cgaattgaag ttggcctccg aagctgttcg   2580
gaagtttcgg ggtcgggaag agattaagaa attgaaagaa ttgggtttcg aacgtgcgca   2640
acattacggc tgggagaact cctataccct taccaaagcg attggtgaag cggttattca   2700
tagtaaacgc ggtaatctcc ccgtcgtgat tatccgtcct tccattatcg aatcttctta   2760
caacgagccc tttcctggtt ggattcaagg cacccgggatg gctgatccca tcattctcgc   2820
ttacgccaaa gggcagattt ctgacttctg gccgacccc caatccttaa tggacatcat   2880
tccggtcgat atggtagcca atgccgccat tgctgcgatg gctaagcacg gttgcggcgt   2940
tcccgagttc aaagtgtaca acttgaccag tagctcccat gtgaaccccta tgcgggctgg   3000
caaactgatt gatctgtccc accagcattt gtgcgatttt cccctcgaag aaaccgtgat   3060
cgacttggaa cacatgaaga tccatagtag cttagaaggc tttactagcg ccttgagcaa   3120
caccatcatc aaacaggaac gcgttatcga caacgaaggg ggtggcttat ccaccaaagg   3180
gaaacgcaag ctcaactact tcgtaagcct cgccaagacc tacgaaccct acaccttctt   3240
ccaagcccgg ttcgacaaca ctaacaccac cagcttgatt caggaaatgt ctatggaaga   3300
gaagaaaact tttggttttg acattaaggg gattgattgg gaacactata tcgtgaatgt   3360
gcacctcccc ggtctgaaga aagaattctt gtccaaaaag aaaaccgaat aa             3412
```

<210> SEQ ID NO 3
<211> LENGTH: 3397
<212> TYPE: DNA
<213> ORGANISM: Artificial sequence
<220> FEATURE:
<223> OTHER INFORMATION: Synthetic construct: FadD-Far6 operon

<400> SEQUENCE: 3

```
atggccaaga aggtttggct taaccgttat cccgcggacg ttccgacgga gatcaaccct     60
gaccgttatc aatctctggt agatatgttt gagcagtcgg tcgcgcgcta cgccgatcaa    120
cctgcgtttg tgaatatggg ggaggtaatg accttccgca agctggaaga acgcagtcgc    180
gcgtttgccg cttatttgca acaagggttg gggctgaaga aggcgatcg cgttgcgttg    240
atgatgccta atttattgca atatccggtg gcgctgtttg gcattttgcg tgccgggatg    300
atcgtcgtaa acgttaaccc cgttgtatacc ccgcgtgagc ttgagcatca gcttaacgat    360
agcggcgcat cggcgattgt tatcgtgtct aactttgctc acacactgga aaaagtggtt    420
gataaaaccg ccgttcagca cgtaattctg acccgtatgg gcgatcagct atctacggca    480
aaaggcacgg tagtcaattt cgttgttaaa tacatcaagc gtttggtgcc gaaataccat    540
```

```
ctgccagatg ccatttcatt tcgtagcgca ctgcataacg gctaccggat gcagtacgtc    600
aaacccgaac tggtgccgga agatttagct tttctgcaat acaccggcgg caccactggt    660
gtggcgaaag gcgcgatgct gactcaccgc aatatgctgg cgaacctgga acaggttaac    720
gcgacctatg tccgctgtt gcatccgggc aaagagctgg tggtgacggc gctgccgctg    780
tatcacattt ttgccctgac cattaactgc ctgctgttta tcgaactggg tgggcagaac    840
ctgcttatca ctaacccgcg cgatattcca gggttggtaa aagagttagc gaaatatccg    900
tttaccgcta tcacgggcgt taacaccttg ttcaatgcgt tgctgaacaa taaagagttc    960
cagcagctgg atttctccag tctgcatctt tccgcaggcg gtgggatgcc agtgcagcaa   1020
gtggtggcag agcgttgggt gaaactgacc ggacagtatc tgctggaagg ctatggcctt   1080
accgagtgtg cgccgctggt cagcgttaac ccatatgata ttgattatca tagtggtagc   1140
atcggtttgc cggtgccgtc gacggaagcc aaactggtgg atgatgatga taatgaagta   1200
ccaccaggtc aaccgggtga gctttgtgtc aaaggaccgc aggtgatgct gggttactgg   1260
cagcgtcccg atgctaccga tgaaatcatc aaaaatggct ggttacacac cggcgacatc   1320
gcggtaatgg atgaagaagg attcctgcgc attgtcgatc gtaaaaaaga catgattctg   1380
gtttccggtt ttaacgtcta tcccaacgag attgaagatg tcgtcatgca gcatcctggc   1440
gtacaggaag tcgcggctgt tggcgtacct tccggctcca gtggtgaagc ggtgaaaatc   1500
ttcgtagtga aaaagatcc atcgcttacc gaagagtcac tggtgacttt ttgccgccgt   1560
cagctcacgg gatacaaagt accgaagctg gtggagtttc gtgatgagtt accgaaatct   1620
aacgtcggaa aaattttgcg acgagaatta cgtgacgaag cgcgcggcaa agtggacaat   1680
aaagcctgag gatcctagta actgtcgtta actgctttgt tggtactacc tgacttcacc   1740
ctcttttaag atggccacca ccaatgtact ggctacctcc cacgccttca aactgaatgg   1800
tgttagctac ttttctagtt tcccccgcaa acccaatcac tacatgcctc gccgtcgtct   1860
gtctcacacc acccgccgtg tccagaccag ttgtttctat ggcgaaacca gcttcgaggc   1920
cgtgacctcc ctggtcaccc ccaaaactga acttcccgg aacagcgatg gtattggcat   1980
tgttcggttt ctcgaaggta atcctactt ggtgaccggt gccaccggtt ttctggccaa   2040
agtgctgatt gagaaactgc tccgtgagtc cctcgaaatc ggtaagatct tcttgttgat   2100
gcggtccaaa gaccaagaaa gtgcgaacaa gcggctgtat gatgagatca tttcttctga   2160
tctgttcaag ctcctgaaac aaatgcacgg tagctcctat gaagccttta tgaagcgcaa   2220
actcattccc gttattggtg acattgaaga agataacctc ggcatcaaaa gtgaaattgc   2280
taacatgatt tccgaagaaa tcgatgtaat catctcctgt ggtggtcgca ctacttttga   2340
cgaccgttat gatagtgctt taagcgtcaa tgctttgggc cctggccgtc tgttgagctt   2400
cggcaagggc tgccggaaac tcaaactctt tttgcacttt tccaccgcct acgtgaccgg   2460
gaaacgcgag gggactgtgt tagaaacccc gttatgtatt ggcgaaaaca ttaccagtga   2520
cttgaatatc aaatccgaat tgaagttggc ctccgaagct gttcggaagt ttcggggtcg   2580
ggaagagatt aagaaattga aagaattggg tttcgaacgt gcgcaacatt acggctggga   2640
gaactcctat accctttacca aagcgattgg tgaagcggtt attcatagta aacgcggtaa   2700
tctccccgtc gtgattatcc gtccttccat tatcgaatct tcttacaacg agccctttcc   2760
tggttggatt caaggcaccc ggatggctga tcccatcatt ctcgcttacg ccaaagggca   2820
gatttctgac ttctgggccg accccaatc cttaatggac atcattccgg tcgatatggt   2880
agccaatgcc gccattgctg cgatggctaa gcacggttgc ggcgttcccg agttcaaagt   2940
```

```
gtacaacttg accagtagct cccatgtgaa ccctatgcgg gctggcaaac tgattgatct      3000
gtcccaccag catttgtgcg attttcccct cgaagaaacc gtgatcgact tggaacacat      3060
gaagatccat agtagcttag aaggctttac tagcgccttg agcaacacca tcatcaaaca      3120
ggaacgcgtt atcgacaacg aagggggtgg cttatccacc aaagggaaac gcaagctcaa      3180
ctacttcgta agcctcgcca agacctacga accctacacc ttcttccaag cccggttcga      3240
caacactaac accaccagct tgattcagga aatgtctatg aagagaaga aaacttttgg       3300 ttttgacatt aagggggattg attgggaaca ctatatcgtg aatgtgcacc tccccggtct     3360
gaagaaagaa ttcttgtcca aaagaaaac cgaataa                                3397

<210> SEQ ID NO 4
<211> LENGTH: 3670
<212> TYPE: DNA
<213> ORGANISM: Artificial sequence
<220> FEATURE:
<223> OTHER INFORMATION: Synthetic construct: LuxCDE operon

<400> SEQUENCE: 4
atgactaaaa aaatttcatt cattattaac ggccaggttg aaatctttcc cgaaagtgat       60
gatttagtgc aatccattaa ttttggtgat aatagtgttt acctgccaat attgaatgac      120
tctcatgtaa aaacattat tgattgtaat ggaaataacg aattacggtt gcataacatt       180
gtcaattttc tctatacggt agggcaaaga tggaaaaatg aagaatactc aagacgcagg      240
acatacattc gtgacttaaa aaatatatg ggatattcag aagaaatggc taagctagag       300
gccaattgga tatctatgat tttatgttct aaaggcggcc tttatgatgt tgtagaaaat      360
gaacttggtt ctcgccatat catggatgaa tggctacctc aggatgaaag ttatgttcgg      420
gcttttccga aggtaaatc tgtacatctg ttggcaggta atgttccatt atctgggatc       480
atgtctatat tacgcgcaat tttaactaag aatcagtgta ttataaaaac atcgtcaacc      540 gatccttta ccgctaatgc attagcgtta agttttattg atgtagaccc taatcatccg       600
ataacgcgct ctttatctgt tatatattgg ccccaccaag gtgatacatc actcgcaaaa      660
gaaattatgc gacatgcgga tgttattgtc gcttggggag ggccagatgc gattaattgg      720
gcggtagagc atgcgccatc ttatgctgat gtgattaaat ttggttctaa aaagagtctt      780
tgcattatcg ataatcctgt tgatttgacg tccgcagcga caggtgcggc tcatgatgtt      840
tgtttttacg atcagcgagc ttgttttttct gcccaaaaca tattacat gggaaatcat       900 tatgaggaat ttaagttagc gttgataaga aaacttaatc tatatgcgca tatattaccg      960
aatgccaaaa aagatttga tgaaaggcg gcctattctt tagttcaaaa agaaagcttg       1020
tttgctggat taaagtaga ggtggatatt catcaacgtt ggatgattat tgagtcaaat      1080
gcaggtgtgg aatttaatca accacttggc agatgtgtgt accttcatca cgtcgataat      1140
attgagcaaa tattgccta tgttcaaaaa ataagacgc aaaccatatc tattttttct      1200
tgggagtcat catttaaata tcgagatgcg ttagcattaa aaggtgcgga aaggattgta      1260
gaagcaggaa tgaataacat atttcgagtt ggtggatctc atgacggaat gagaccgttg      1320
caacgattag tgacatatat ttctcatgaa aggccatcta actatacggc taaggatgtt      1380
gcggttgaaa tagaacagac tcgattcctg gaagaagata gttccttgt atttgtccca      1440 taataggtaa agtatggaa aatgaatcaa atataaaac catcgaccac gttatttgtg       1500
ttgaaggaaa taaaaaaatt catgtttggg aaacgctgcc agaagaaaac agcccaaaga     1560
gaaagaatgc cattattatt gcgtctggtt ttgcccgcag gatggatcat tttgctggtc     1620
```

```
tggcggaata tttatcgcgg aatggatttc atgtgatccg ctatgattcg cttcaccacg    1680
ttggattgag ttcagggaca attgatgaat ttacaatgtc tataggaaag cagagcttgt    1740
tagcagtggt tgattggtta actacacgaa aaataaataa cttcggtatg ttggcttcaa    1800
gcttatctgc gcggatagct tatgcaagcc tatctgaaat caatgcttcg ttttaatca    1860
ccgcagtcgg tgttgttaac ttaagatatt ctcttgaaag agctttaggg tttgattatc    1920
tcagtctacc cattaatgaa ttgccggata atctagattt tgaaggccat aaattgggtg    1980
ctgaagtctt tgcgagagat tgtcttgatt ttggttggga agatttagct tctacaatta    2040
ataacatgat gtatcttgat ataccgttta ttgcttttac tgcaaataac gataattggg    2100
tcaagcaaga tgaagttatc acattgttat caaatattcg tagtaatcga tgcaagatat    2160
attctttgtt aggaagttcg catgacttga gtgaaaattt agtggtcctg cgcaattttt    2220
atcaatcggt tacgaaagcc gctatcgcga tggataatga tcatctggat attgatgttg    2280
atattactga accgtcattt gaacatttaa ctattgcgac agtcaatgaa cgccgaatga    2340
gaattgagat tgaaaatcaa gcaatttctc tgtcttaaat agatttcgag ttgcagcgag    2400
gcggcaagtg aacgaatccc caggagcata gataactatg tgactggggt gagtgaaagc    2460
agccaacaaa gcagcagctt gaaagatgaa gggtataaaa gagtatgaca gcagtgctgc    2520
catactttct aatattatct tgaggagtaa acaggtatg acttcatatg ttgataaaca    2580
agaaattaca gcaagctcag aaattgatga tttgatttt tcgagcgatc cattagtgtg    2640
gtcttacgac gagcaggaaa aaatcagaaa gaaacttgtg cttgatgcat ttcgtaatca    2700
ttataaacat tgtcgagaat atcgtcacta ctgtcaggca cacaaagtag atgacaatat    2760
tacggaaatt gatgacatac ctgtattccc aacatcggtt tttaagttta ctcgcttatt    2820
aacttctcag gaaaacgaga ttgaaagttg gtttaccagt agcggcacga atggtttaaa    2880
aagtcaggtg gcgcgtgaca gattaagtat tgagagactc ttaggctctg tgagttatgg    2940
catgaaatat gttggtagtt ggtttgatca tcaaatagaa ttagtcaatt gggaccaga    3000
tagatttaat gctcataata tttggtttaa atatgttatg agtttggtgg aattgttata    3060
tcctacgaca tttaccgtaa cagaagaacg aatagatttt gttaaaacat tgaatagtct    3120
tgaacgaata aaaaatcaag ggaaagatct ttgtcttatt ggttcgccat actttattta    3180
tttactctgc cattatatga agataaaaa aatctcattt tctggagata aaagccttta    3240
tatcataacc ggaggcggct ggaaaagtta cgaaaaagaa tctctgaaac gtgatgattt    3300
caatcatctt ttatttgata ctttcaatct cagtgatatt agtcagatcc gagatatatt    3360
taatcaagtt gaactcaaca cttgtttctt tgaggatgaa atgcagcgta acatgttcc    3420
gccgtgggta tatgcgcgag cgcttgatcc tgaaacgttg aaacctgtac ctgatggaac    3480
gccggggttg atgagttata tggatgcgtc agcaaccagt tatccagcat ttattgttac    3540
cgatgatgtc gggataatta gcagagaata tggtaagtat cccggcgtgc tcgttgaaat    3600
tttacgtcgc gtcaatacga ggacgcagaa agggtgtgct ttaagcttaa ccgaagcgtt    3660
tgatagttga                                                           3670
```

<210> SEQ ID NO 5
<211> LENGTH: 1089
<212> TYPE: DNA
<213> ORGANISM: Artificial sequence
<220> FEATURE:
<223> OTHER INFORMATION: Synthetic construct: Codon-optimized C14FatB1 gene

<400> SEQUENCE: 5

-continued

```
atggcaaatg gtgcagcggt taatctgaag tctggttctt tgaataccca agaggatacc      60
tcttccagcc ctccacctcg tgcgtttctg aaccaattac ccgactggag catgctgttg     120
accgctatca ctaccgtgtt cgtggcggca gaaaagcaat ggaccatgct ggatcgtaag     180
agcaaacgtc ccgatatgtt agtggactcc gtcggtttga gaatatcgt gcgtgacggc      240 ttagtttctc gccagtcttt ctctattcgc agctatgaaa tcggcgcaga ccgcaccgcc     300
tccattgaaa cgttaatgaa ccacctgcaa gagactagca ttaaccattg taaatccttg     360
ggcctgttga tgatggcttc ggccgtact cccggtatgt gcaagaacga tctgatctgg      420
gttttgacta agatgcagat tttggtcaac cgctatccgg cgtggggtga tactgtggag     480
atcaacacct ggtttagcca gtccggtaag attggtatgg ctccgactg gttgattagc      540 gattgcaata ccggtgaaat cctgattcgc gccacgagcg tgtgggcaat gatgaatcag     600
aaaacccgtc gcttcagccg tttaccgtac gaagttcgtc aggaattgac tccgcattt      660 gtcgacagcc cacacgttat cgaggacaac gaccgcaaac tgcataagtt cgacgtcaag     720
accggtgatt ctatccgcaa aggtttgacc cctcgctgga atgacctgga cgttaaccag     780
cacgtttcta atgtcaaata catcggctgg attctggagt ccatgcctat tgaggtcctg     840
gagactcaag agttgtgttc cttaaccgtc gaatatcgtc gcgaatgcgg tatggacagc     900
gtcttagagt ccgtgactgc ccgtgacccc tctgaagatg gtggccgctc tcagtacaac     960
cacttattgc gtttagagga tggcactgat gttgttaaag gccgtaccga gtggcgctcc    1020
aagaacgctg gcactaatgg tgcgacttct accgcgaaaa cctccaatgg taatagtgtg    1080
agttaataa                                                            1089
```

<210> SEQ ID NO 6
<211> LENGTH: 361
<212> TYPE: PRT
<213> ORGANISM: Artificial sequence
<220> FEATURE:
<223> OTHER INFORMATION: Synthetic construct: C14FatB1 thioesterase
      encoded by expression construct

<400> SEQUENCE: 6

```
Met Ala Asn Gly Ala Ala Val Asn Leu Lys Ser Gly Ser Leu Asn Thr
1               5                   10                  15

Gln Glu Asp Thr Ser Ser Ser Pro Pro Arg Ala Phe Leu Asn Gln
            20                  25                  30

Leu Pro Asp Trp Ser Met Leu Leu Thr Ala Ile Thr Thr Val Phe Val
        35                  40                  45

Ala Ala Glu Lys Gln Trp Thr Met Leu Asp Arg Lys Ser Lys Arg Pro
    50                  55                  60

Asp Met Leu Val Asp Ser Val Gly Leu Lys Asn Ile Val Arg Asp Gly
65                  70                  75                  80

Leu Val Ser Arg Gln Ser Phe Ser Ile Arg Ser Tyr Glu Ile Gly Ala
                85                  90                  95

Asp Arg Thr Ala Ser Ile Glu Thr Leu Met Asn His Leu Gln Glu Thr
            100                 105                 110

Ser Ile Asn His Cys Lys Ser Leu Gly Leu Leu Asn Asp Gly Phe Gly
        115                 120                 125

Arg Thr Pro Gly Met Cys Lys Asn Asp Leu Ile Trp Val Leu Thr Lys
    130                 135                 140

Met Gln Ile Leu Val Asn Arg Tyr Pro Ala Trp Gly Asp Thr Val Glu
145                 150                 155                 160
```

```
Ile Asn Thr Trp Phe Ser Gln Ser Gly Lys Ile Gly Met Gly Ser Asp
                165                 170                 175

Trp Leu Ile Ser Asp Cys Asn Thr Gly Glu Ile Leu Ile Arg Ala Thr
            180                 185                 190

Ser Val Trp Ala Met Met Asn Gln Lys Thr Arg Arg Phe Ser Arg Leu
        195                 200                 205

Pro Tyr Glu Val Arg Gln Glu Leu Thr Pro His Phe Val Asp Ser Pro
    210                 215                 220

His Val Ile Glu Asp Asn Asp Arg Lys Leu His Lys Phe Asp Val Lys
225                 230                 235                 240

Thr Gly Asp Ser Ile Arg Lys Gly Leu Thr Pro Arg Trp Asn Asp Leu
                245                 250                 255

Asp Val Asn Gln His Val Ser Asn Val Lys Tyr Ile Gly Trp Ile Leu
            260                 265                 270

Glu Ser Met Pro Ile Glu Val Leu Glu Thr Gln Glu Leu Cys Ser Leu
        275                 280                 285

Thr Val Glu Tyr Arg Arg Glu Cys Gly Met Asp Ser Val Leu Glu Ser
    290                 295                 300

Val Thr Ala Arg Asp Pro Ser Glu Asp Gly Gly Arg Ser Gln Tyr Asn
305                 310                 315                 320

His Leu Leu Arg Leu Glu Asp Gly Thr Asp Val Val Lys Gly Arg Thr
                325                 330                 335

Glu Trp Arg Ser Lys Asn Ala Gly Thr Asn Gly Ala Thr Ser Thr Ala
            340                 345                 350

Lys Thr Ser Asn Gly Asn Ser Val Ser
        355                 360

<210> SEQ ID NO 7
<211> LENGTH: 3153
<212> TYPE: DNA
<213> ORGANISM: Artificial sequence
<220> FEATURE:
<223> OTHER INFORMATION: Synthetic construct: FadD-luxC operon

<400> SEQUENCE: 7
atggccaaga aggtttggct taaccgttat cccgcggacg ttccgacgga gatcaaccct      60
gaccgttatc aatctctggt agatatgttt gagcagtcgg tcgcgcgcta cgccgatcaa     120
cctgcgtttg tgaatatggg ggaggtaatg accttccgca agctggaaga acgcagtcgc     180
gcgtttgccg cttatttgca caagggttgg ggctgaagaa aaggcgatcg cgttgcgttg     240
atgatgccta atttattgca atatccggtg gcgctgtttg gcattttgcg tgccgggatg     300
atcgtcgtaa acgttaaccc gttgtatacc ccgcgtgagc ttgagcatca gcttaacgat     360
agcggcgcat cggcgattgt tatcgtgtct aactttgctc acacactgga aaaagtggtt     420
gataaaaccg ccgttcagca cgtaattctg acccgtatgg gcgatcagct atctacggca     480
aaaggcacgg tagtcaattt cgttgttaaa tacatcaagc gtttggtgcc gaaataccat     540
ctgccagatg ccatttcatt tcgtagcgca ctgcataacg gctaccggat gcagtacgtc     600
aaacccgaac tggtgccgga agatttagct tttctgcaat acaccggcgg caccactggt     660
gtggcgaaag cgcgatgct gactcaccgc aatatgctgg cgaacctgga acaggttaac     720
gcgacctatg gtccgctgtt gcatccgggc aaagagctgg tggtgacggc gctgccgctg     780
tatcacattt ttgccctgac cattaactgc ctgctgttta tcgaactggg tgggcagaac     840
ctgcttatca ctaacccgcg cgatattcca gggttggtaa aagagttagc gaaatatccg     900
tttaccgcta tcacgggcgt taacaccttg ttcaatgcgt tgctgaacaa taagagttc     960
```

```
cagcagctgg atttctccag tctgcatctt tccgcaggcg gtgggatgcc agtgcagcaa    1020
gtggtggcag agcgttgggt gaaactgacc ggacagtatc tgctggaagg ctatggcctt    1080
accgagtgtg cgccgctggt cagcgttaac ccatatgata ttgattatca tagtggtagc    1140
atcggtttgc cggtgccgtc gacggaagcc aaactggtgg atgatgatga taatgaagta    1200
ccaccaggtc aaccgggtga gctttgtgtc aaaggaccgc aggtgatgct gggttactgg    1260
cagcgtcccg atgctaccga tgaaatcatc aaaaatggct ggttacacac cggcgacatc    1320
gcggtaatgg atgaagaagg attcctgcgc attgtcgatc gtaaaaaaga catgattctg    1380
gtttccggtt ttaacgtcta tcccaacgag attgaagatg tcgtcatgca gcatcctggc    1440
gtacaggaag tcgcggctgt tggcgtacct tccggctcca gtggtgaagc ggtgaaaatc    1500
ttcgtagtga aaaagatcc atcgcttacc gaagagtcac tggtgacttt ttgccgccgt    1560
cagctcacgg gatacaaagt accgaagctg gtggagtttc gtgatgagtt accgaaatct    1620
aacgtcggaa aaattttgcg acgagaatta cgtgacgaag cgcgcggcaa agtggacaat    1680
aaagcctgag gatcctaagg aggaaaaaaa atgactaaaa aatttcatt cattattaac    1740 ggccaggttg aaatctttcc cgaaagtgat gatttagtgc aatccattaa ttttggtgat    1800
aatagtgttt acctgccaat attgaatgac tctcatgtaa aaacattat tgattgtaat    1860 ggaaataacg aattacggtt gcataacatt gtcaattttc tctatacggt agggcaaaga    1920
tggaaaaatg aagaatactc aagacgcagg acatacattc gtgacttaaa aaatatatg    1980 ggatattcag aagaaatggc taagctagag gccaattgga tatctatgat ttatgttct    2040 aaaggcggcc tttatgatgt tgtagaaaat gaacttggtt ctcgccatat catggatgaa    2100
tggctacctc aggatgaaag ttatgttcgg gcttttccga aggtaaaatc tgtacatctg    2160
ttggcaggta atgttccatt atctgggatc atgtctatat tacgcgcaat tttaactaag    2220
aatcagtgta ttataaaaac atcgtcaacc gatccttta ccgctaatgc attagcgtta    2280
agttttattg atgtagaccc taatcatccg ataacgcgct ctttatctgt tatatattgg    2340
ccccaccaag gtgatacatc actcgcaaaa gaaattatgc gacatgcgga tgttattgtc    2400
gcttggggag ggccagatgc gattaattgg gcggtagagc atgcgccatc ttatgctgat    2460
gtgattaaat ttggttctaa aaagagtctt tgcattatcg ataatcctgt tgatttgacg    2520
tccgcagcga caggtgcggc tcatgatgtt tgtttttacg atcagcgagc ttgttttttct    2580 gcccaaaaca tatattacat gggaaatcat tatgaggaat ttaagttagc gttgatagaa    2640
aaacttaatc tatatgcgca tatattaccg aatgccaaaa aagattttga tgaaaaggcg    2700
gcctattctt tagttcaaaa agaaagcttg tttgctggat taaaagtaga ggtgatatt    2760 catcaacgtt ggatgattat tgagtcaaat gcaggtgtgg aatttaatca accacttggc    2820
agatgtgtgt accttcatca cgtcgataat attgagcaaa tattgcctta tgttcaaaaa    2880
aataagacgc aaaccatatc tatttttcct tgggagtcat catttaaata tcgagatgcg    2940
ttagcattaa aaggtgcgga aaggattgta gaagcaggaa tgaataacat atttcgagtt    3000
ggtggatctc atgacggaat gagaccgttg caacgattag tgcatatat ttctcatgaa    3060 aggccatcta actatacggc taaggatgtt gcggttgaaa tagaacagac tcgattcctg    3120
gaagaagata agttccttgt atttgtccca taa                                3153
```

<210> SEQ ID NO 8
<211> LENGTH: 513
<212> TYPE: PRT
<213> ORGANISM: Marinobacter aquaeoli VT8

<400> SEQUENCE: 8

| | | | | | | | | | | | | | | |
|---|---|---|---|---|---|---|---|---|---|---|---|---|---|---|
|Met|Ala|Ile|Gln|Gln|Val|His|His|Ala|Asp|Thr|Ser|Ser|Lys|Val|
|1| | | |5| | | | |10| | | | |15|
|Leu|Gly|Gln|Leu|Arg|Gly|Lys|Arg|Val|Leu|Ile|Thr|Gly|Thr|Thr|Gly|
| | | | |20| | | | |25| | | | |30| |
|Phe|Leu|Gly|Lys|Val|Val|Leu|Glu|Arg|Leu|Ile|Arg|Ala|Val|Pro|Asp|
| | | | |35| | | | |40| | | | |45| |
|Ile|Gly|Ala|Ile|Tyr|Leu|Leu|Ile|Arg|Gly|Asn|Lys|Arg|His|Pro|Asp|
|50| | | | |55| | | | |60| | | | | |
|Ala|Arg|Ser|Arg|Phe|Leu|Glu|Glu|Ile|Ala|Thr|Ser|Ser|Val|Phe|Asp|
|65| | | | |70| | | | |75| | | | |80|
|Arg|Leu|Arg|Glu|Ala|Asp|Ser|Glu|Gly|Phe|Asp|Ala|Phe|Leu|Glu|Glu|
| | | | |85| | | | |90| | | | |95| |
|Arg|Ile|His|Cys|Val|Thr|Gly|Glu|Val|Thr|Glu|Ala|Gly|Phe|Gly|Ile|
| | | |100| | | | |105| | | | |110| | |
|Gly|Gln|Glu|Asp|Tyr|Arg|Lys|Leu|Ala|Thr|Glu|Leu|Asp|Ala|Val|Ile|
| | | |115| | | | |120| | | | |125| | |
|Asn|Ser|Ala|Ala|Ser|Val|Asn|Phe|Arg|Glu|Glu|Leu|Asp|Lys|Ala|Leu|
| |130| | | | |135| | | | |140| | | | |
|Ala|Ile|Asn|Thr|Leu|Cys|Leu|Arg|Asn|Ile|Ala|Gly|Met|Val|Asp|Leu|
|145| | | | |150| | | | |155| | | | |160|
|Asn|Pro|Lys|Leu|Ala|Val|Leu|Gln|Val|Ser|Thr|Cys|Tyr|Val|Asn|Gly|
| | | | |165| | | | |170| | | | |175| |
|Met|Asn|Ser|Gly|Gln|Val|Thr|Glu|Ser|Val|Ile|Lys|Pro|Ala|Gly|Glu|
| | | |180| | | | |185| | | | |190| | |
|Ala|Val|Pro|Arg|Ser|Pro|Asp|Gly|Phe|Tyr|Glu|Ile|Glu|Glu|Leu|Val|
| | | |195| | | | |200| | | | |205| | |
|Arg|Leu|Leu|Gln|Asp|Lys|Ile|Glu|Asp|Val|Gln|Ala|Arg|Tyr|Ser|Gly|
| | |210| | | | |215| | | | |220| | | |
|Lys|Val|Leu|Glu|Arg|Lys|Leu|Val|Asp|Leu|Gly|Ile|Arg|Glu|Ala|Asn|
|225| | | | |230| | | | |235| | | | |240|
|Arg|Tyr|Gly|Trp|Ser|Asp|Thr|Tyr|Thr|Phe|Thr|Lys|Trp|Leu|Gly|Glu|
| | | | |245| | | | |250| | | | |255| |
|Gln|Leu|Leu|Met|Lys|Ala|Leu|Asn|Gly|Arg|Thr|Leu|Thr|Ile|Leu|Arg|
| | | |260| | | | |265| | | | |270| | |
|Pro|Ser|Ile|Ile|Glu|Ser|Ala|Leu|Glu|Glu|Pro|Ala|Pro|Gly|Trp|Ile|
| | |275| | | | |280| | | | |285| | | |
|Glu|Gly|Val|Lys|Val|Ala|Asp|Ala|Ile|Ile|Leu|Ala|Tyr|Ala|Arg|Glu|
| |290| | | | |295| | | | |300| | | | |
|Lys|Val|Thr|Leu|Phe|Pro|Gly|Lys|Arg|Ser|Gly|Ile|Ile|Asp|Val|Ile|
|305| | | | |310| | | | |315| | | | |320|
|Pro|Val|Asp|Leu|Val|Ala|Asn|Ser|Ile|Ile|Leu|Ser|Leu|Ala|Glu|Ala|
| | | | |325| | | | |330| | | | |335| |
|Leu|Gly|Glu|Pro|Gly|Arg|Arg|Ile|Tyr|Gln|Cys|Cys|Ser|Gly|Gly|
| | | |340| | | | |345| | | | |350| | |
|Gly|Asn|Pro|Ile|Ser|Leu|Gly|Glu|Phe|Ile|Asp|His|Leu|Met|Ala|Glu|
| | |355| | | | |360| | | | |365| | | |
|Ser|Lys|Ala|Asn|Tyr|Ala|Ala|Tyr|Asp|His|Leu|Phe|Tyr|Arg|Gln|Pro|
| |370| | | | |375| | | | |380| | | | |
|Ser|Lys|Pro|Phe|Leu|Ala|Val|Asn|Arg|Ala|Leu|Phe|Asp|Leu|Val|Ile|
|385| | | | |390| | | | |395| | | | |400|
|Ser|Gly|Val|Arg|Leu|Pro|Leu|Ser|Leu|Thr|Asp|Arg|Val|Leu|Lys|Leu|
| | | | |405| | | | |410| | | | |415| |

```
Leu Gly Asn Ser Arg Asp Leu Lys Met Leu Arg Asn Leu Asp Thr Thr
            420                 425                 430
Gln Ser Leu Ala Thr Ile Phe Gly Phe Tyr Thr Ala Pro Asp Tyr Ile
            435                 440                 445
Phe Arg Asn Asp Glu Leu Met Ala Leu Ala Asn Arg Met Gly Glu Val
        450                 455                 460
Asp Lys Gly Leu Phe Pro Val Asp Ala Arg Leu Ile Asp Trp Glu Leu
465                 470                 475                 480
Tyr Leu Arg Lys Ile His Leu Ala Gly Leu Asn Arg Tyr Ala Leu Lys
                485                 490                 495
Glu Arg Lys Val Tyr Ser Leu Lys Thr Ala Arg Gln Arg Lys Lys Ala
            500                 505                 510
Ala

<210> SEQ ID NO 9
<211> LENGTH: 1542
<212> TYPE: DNA
<213> ORGANISM: Marinobacter aquaeoli VT8

<400> SEQUENCE: 9
```

| | | | | | |
|---|---|---|---|---|---|
| tcaggcagct | ttttgcgct | ggcgcgcggt | tttcagactg | tacacctttc | gttctttcag | 60 |
| ggcatagcga | ttgagcccgg | ccaggtgaat | cttgcgcagg | tagagctccc | agtcaatcag | 120 |
| gcgggcatcc | accgggaaca | gcccttatc | gacctcaccc | atccggttcg | ccagcgccat | 180 |
| cagctcatcg | ttccgaaga | tataatccgg | cgcggtgtag | aaaccaaaaa | tggttgccag | 240 |
| cgactgggtg | gtatccagat | tcctgagcat | tttcaggtcc | cgggaatttc | ccagtaattt | 300 |
| gagcacacgg | tccgtcaggg | agagcggtaa | gcgaacacca | ctgatcacca | aatcaaacag | 360 |
| cgcccggtta | accgccagaa | acggcttgct | gggctgccgg | tagaacaggt | gatcgtaggc | 420 |
| agcgtaattg | gcttttgatt | ccgccatgag | atgatcgatg | aactcaccca | gggagattgg | 480 |
| attgccgccc | ccgctgcaac | attgatagat | gcgacgtcga | ccgggttctc | caagagcttc | 540 |
| cgccagggaa | aggatgatgg | agttggccac | caggtccact | ggaatcacat | cgatgatacc | 600 |
| ggagcgtttg | cccgggaaga | gggtgacttt | ttcccgtgcg | taagccagga | tgatggcatc | 660 |
| tgccaccttc | acccctcaa | tccagccggg | cgctggttcc | tccagggcac | tttcgataat | 720 |
| cgaaggacgc | agaatggtca | gcgtgcgccc | gtttaacgcc | ttcatcagca | actgttcgcc | 780 |
| cagccacttg | gtaaaggtgt | aggtatcgct | ccagccatag | cggttggctt | cccgaatccc | 840 |
| caggtccacc | agcttcctct | ccagcacttt | gccggaataa | cgggcctgaa | cgtcttcaat | 900 |
| tttatcctga | gcaggcgaa | caagctcttc | tatctcatag | aagccgtccg | ggaacgcgg | 960 |
| cacggcctcg | cctgccggct | tgatcaccga | ttcggttacc | tgccccgagt | tcatgccatt | 1020 |
| gacatagcag | gtggagacct | gcaggaccgc | aagcttcgga | ttcaaatcca | ccatgccggc | 1080 |
| aatattccga | aggcacaggg | tgttgatggc | cagcgccttg | tcgagctctt | cacggaaatt | 1140 |
| cacgcttgca | gcggagttga | tcaccgcatc | cagttcggtg | gcgagtttgc | gatagtcttc | 1200 |
| ctgcccatc | ccgaaacccg | cttcggtcac | ctcaccggtc | acgcagtgaa | tgcgctcttc | 1260 |
| cagaaaggcg | tcaaatccct | ctgaatcggc | ctcgcgaaga | cggtcaaaca | ccgaggaggt | 1320 |
| ggcaatttct | tccaggaaac | gggaacgagc | atccggatgc | cgtttattgc | cccggatcag | 1380 |
| caggtaaatt | gccgcgatat | caggcaccgc | ccgaatcagc | ctttcgagga | ccaccttgcc | 1440 |
| cagaaagcca | gtggtaccgg | tgatcagaac | ccgcttgcca | cggagctgtc | cgagcacctt | 1500 |
| tgatgatgaa | gtgtcagcgt | gatgtacctg | ctgtattgcc | at | | 1542 |

<210> SEQ ID NO 10
<211> LENGTH: 3252
<212> TYPE: DNA
<213> ORGANISM: Artificial sequence
<220> FEATURE:
<223> OTHER INFORMATION: Synthetic construct: FadD-Maqu_2220 operon

<400> SEQUENCE: 10

| | | | | | |
|---|---|---|---|---|---|
| atggccaaga | aggtttggct | taaccgttat | cccgcggacg | ttccgacgga | gatcaaccct | 60 |
| gaccgttatc | aatctctggt | agatatgttt | gagcagtcgg | tcgcgcgcta | cgccgatcaa | 120 |
| cctgcgtttg | tgaatatggg | ggaggtaatg | accttccgca | agctggaaga | acgcagtcgc | 180 |
| gcgtttgccg | cttatttgca | caagggttg | gggctgaaga | aaggcgatcg | cgttgcgttg | 240 |
| atgatgccta | atttattgca | atatccggtg | gcgctgtttg | gcattttgcg | tgccgggatg | 300 |
| atcgtcgtaa | acgttaaccc | gttgtatacc | ccgcgtgagc | ttgagcatca | gcttaacgat | 360 |
| agcggcgcat | cggcgattgt | tatcgtgtct | aactttgctc | acacactgga | aaaagtggtt | 420 |
| gataaaaccg | ccgttcagca | cgtaattctg | acccgtatgg | gcgatcagct | atctacggca | 480 |
| aaaggcacgt | tagtcaattt | cgttgttaaa | tacatcaagc | gtttggtgcc | gaaataccat | 540 |
| ctgccagatg | ccatttcatt | tcgtagcgca | ctgcataacg | gctaccggat | gcagtacgtc | 600 |
| aaacccgaac | tggtgccgga | agatttagct | tttctgcaat | acaccggcgg | caccactggt | 660 |
| gtggcgaaag | gcgcgatgct | gactcaccgc | aatatgctgg | cgaacctgga | acaggttaac | 720 |
| gcgacctatg | gtccgctgtt | gcatccgggc | aaagagctgg | tggtgacggc | gctgccgctg | 780 |
| tatcacattt | ttgccctgac | cattaactgc | ctgctgttta | tcgaactggg | tgggcagaac | 840 |
| ctgcttatca | ctaacccgcg | cgatattcca | gggttggtaa | aagagttagc | gaaatatccg | 900 |
| tttaccgcta | tcacgggcgt | taacaccttg | ttcaatgcgt | tgctgaacaa | taaagagttc | 960 |
| cagcagctgg | atttctccag | tctgcatctt | tccgcaggcg | gtgggatgcc | agtgcagcaa | 1020 |
| gtggtggcag | agcgttgggt | gaaactgacc | ggacagtatc | tgctggaagg | ctatggcctt | 1080 |
| accgagtgtg | cgccgctggt | cagcgttaac | ccatatgata | ttgattatca | tagtggtagc | 1140 |
| atcggttttgc | cggtgccgtc | gacggaagcc | aaactggtgg | atgatgatga | taatgaagta | 1200 |
| ccaccaggtc | aaccgggtga | gctttgtgtc | aaggaccgc | aggtgatgct | gggttactgg | 1260 |
| cagcgtcccg | atgctaccga | tgaaatcatc | aaaaatggct | ggttacacac | cggcgacatc | 1320 |
| gcggtaatgg | atgaagaagg | attcctgcgc | attgtcgatc | gtaaaaaaga | catgattctg | 1380 |
| gtttccggtt | ttaacgtcta | tcccaacgag | attgaagatg | tcgtcatgca | gcatcctggc | 1440 |
| gtacaggaag | tcgcggctgt | tggcgtacct | tccggctcca | gtggtgaagc | ggtgaaaatc | 1500 |
| ttcgtagtga | aaaagatcc | atcgcttacc | gaagagtcac | tggtgacttt | tgccgccgt | 1560 |
| cagctcacgg | gatacaaagt | accgaagctg | gtggagtttc | gtgatgagtt | accgaaatct | 1620 |
| aacgtcggaa | aaattttgcg | acgagaatta | cgtgacgaag | cgcgcggcaa | agtggacaat | 1680 |
| aaagcctgag | gatccaggag | gatcattact | atggcaatac | agcaggtaca | tcacgctgac | 1740 |
| acttcatcat | caaggtgct | cggacagctc | cgtggcaagc | gggttctgat | caccggtacc | 1800 |
| actggctttc | tggcaaggt | ggtcctcgaa | aggctgattc | gggcggtgcc | tgatatcggc | 1860 |
| gcaatttacc | tgctgatccg | gggcaataaa | cggcatccgg | atgctcgttc | ccgtttcctg | 1920 |
| gaagaaattg | ccacctcctc | ggtgtttgac | cgtcttcgcg | aggccgattc | agagggattt | 1980 |
| gacgcctttc | tggaagagcg | cattcactgc | gtgaccggtg | aggtgaccga | agcgggtttc | 2040 |
| gggatagggc | aggaagacta | tcgcaaactc | gccaccgaac | tggatgcggt | gatcaactcc | 2100 |

```
gctgcaagcg tgaatttccg tgaagagctc gacaaggcgc tggccatcaa caccctgtgc    2160
cttcggaata ttgccggcat ggtggatttg aatccgaagc ttgcggtcct gcaggtctcc    2220
acctgctatg tcaatggcat gaactcgggg caggtaaccg aatcggtgat caagccggca    2280
ggcgaggccg tgccgcgttc cccggacggc ttctatgaga tagaagagct tgttcgcctg    2340
cttcaggata aaattgaaga cgttcaggcc cgttattccg gcaaagtgct ggagaggaag    2400
ctggtggacc tggggattcg ggaagccaac cgctatggct ggagcgatac ctacaccttt    2460
accaagtggc tgggcgaaca gttgctgatg aaggcgttaa acgggcgcac gctgaccatt    2520
ctgcgtcctt cgattatcga aagtgccctg gaggaaccag cgcccggctg gattgagggg    2580
gtgaaggtgg cagatgccat catcctggct tacgcacggg aaaaagtcac cctcttcccg    2640
ggcaaacgct ccggtatcat cgatgtgatt ccagtggacc tggtggccaa ctccatcatc    2700
ctttccctgg cggaagctct tgagaaccc ggtcgacgtc gcatctatca atgttgcagc    2760
gggggcggca atccaatctc cctgggtgag ttcatcgatc atctcatggc ggaatcaaaa    2820
gccaattacg ctgcctacga tcacctgttc taccggcagc ccagcaagcc gtttctggcg    2880
gttaaccggg cgctgtttga tttggtgatc agtggtgttc gcttaccgct ctccctgacg    2940
gaccgtgtgc tcaaattact gggaaattcc cgggacctga aaatgctcag gaatctggat    3000
accacccagt cgctggcaac cattttggt ttctacaccg cgccggatta tatcttccgg    3060
aacgatgagc tgatggcgct ggcgaaccgg atgggtgagg tcgataaagg gctgttcccg    3120
gtggatgccc gcctgattga ctgggagctc tacctgcgca agattcacct ggccgggctc    3180
aatcgctatg ccctgaaaga acgaaggtg tacagtctga aaaccgcgcg ccagcgcaaa    3240
aaagctgcct ga                                                         3252
```

<210> SEQ ID NO 11
<211> LENGTH: 661
<212> TYPE: PRT
<213> ORGANISM: Marinobacter aquaeoli VT8

<400> SEQUENCE: 11

```
Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val Tyr Val Leu Val Arg
            20                  25                  30

Glu Gln Ser Gln Asp Lys Leu Glu Arg Leu Arg Glu Arg Trp Gly Ala
        35                  40                  45

Asp Asp Lys Gln Val Lys Ala Val Ile Gly Asp Leu Thr Ser Lys Asn
    50                  55                  60

Leu Gly Ile Asp Ala Lys Thr Leu Lys Ser Leu Lys Gly Asn Ile Asp
65                  70                  75                  80

His Val Phe His Leu Ala Ala Val Tyr Asp Met Gly Ala Asp Glu Glu
                85                  90                  95

Ala Gln Ala Ala Thr Asn Ile Glu Gly Thr Arg Ala Ala Val Gln Ala
            100                 105                 110

Ala Glu Ala Met Gly Ala Lys His Phe His His Val Ser Ser Ile Ala
        115                 120                 125

Ala Ala Gly Leu Phe Lys Gly Ile Phe Arg Glu Asp Met Phe Glu Glu
    130                 135                 140

Ala Glu Lys Leu Asp His Pro Tyr Leu Arg Thr Lys His Glu Ser Glu
145                 150                 155                 160

Lys Val Val Arg Glu Glu Cys Lys Val Pro Phe Arg Ile Tyr Arg Pro
```

```
                165                 170                 175
Gly Met Val Ile Gly His Ser Glu Thr Gly Glu Met Asp Lys Val Asp
            180                 185                 190
Gly Pro Tyr Tyr Phe Phe Lys Met Ile Gln Lys Ile Arg His Ala Leu
        195                 200                 205
Pro Gln Trp Val Pro Thr Ile Gly Ile Glu Gly Gly Arg Leu Asn Ile
    210                 215                 220
Val Pro Val Asp Phe Val Val Asp Ala Leu Asp His Ile Ala His Leu
225                 230                 235                 240
Glu Gly Glu Asp Gly Asn Cys Phe His Leu Val Asp Ser Asp Pro Tyr
                245                 250                 255
Lys Val Gly Glu Ile Leu Asn Ile Phe Cys Glu Ala Gly His Ala Pro
            260                 265                 270
Arg Met Gly Met Arg Ile Asp Ser Arg Met Phe Gly Phe Ile Pro Pro
        275                 280                 285
Phe Ile Arg Gln Ser Ile Lys Asn Leu Pro Pro Val Lys Arg Ile Thr
    290                 295                 300
Gly Ala Leu Leu Asp Asp Met Gly Ile Pro Pro Ser Val Met Ser Phe
305                 310                 315                 320
Ile Asn Tyr Pro Thr Arg Phe Asp Thr Arg Glu Leu Glu Arg Val Leu
                325                 330                 335
Lys Gly Thr Asp Ile Glu Val Pro Arg Leu Pro Ser Tyr Ala Pro Val
            340                 345                 350
Ile Trp Asp Tyr Trp Glu Arg Asn Leu Asp Pro Asp Leu Phe Lys Asp
        355                 360                 365
Arg Thr Leu Lys Gly Thr Val Glu Gly Lys Val Cys Val Val Thr Gly
    370                 375                 380
Ala Thr Ser Gly Ile Gly Leu Ala Thr Ala Glu Lys Leu Ala Glu Ala
385                 390                 395                 400
Gly Ala Ile Leu Val Ile Gly Ala Arg Thr Lys Glu Thr Leu Asp Glu
                405                 410                 415
Val Ala Ala Ser Leu Glu Ala Lys Gly Gly Asn Val His Ala Tyr Gln
            420                 425                 430
Cys Asp Phe Ser Asp Met Asp Asp Cys Asp Arg Phe Val Lys Thr Val
        435                 440                 445
Leu Asp Asn His Gly His Val Asp Val Leu Val Asn Asn Ala Gly Arg
    450                 455                 460
Ser Ile Arg Arg Ser Leu Ala Leu Ser Phe Asp Arg Phe His Asp Phe
465                 470                 475                 480
Glu Arg Thr Met Gln Leu Asn Tyr Phe Gly Ser Val Arg Leu Ile Met
                485                 490                 495
Gly Phe Ala Pro Ala Met Leu Glu Arg Arg Gly His Val Val Asn
            500                 505                 510
Ile Ser Ser Ile Gly Val Leu Thr Asn Ala Pro Arg Phe Ser Ala Tyr
        515                 520                 525
Val Ser Ser Lys Ser Ala Leu Asp Ala Phe Ser Arg Cys Ala Ala Ala
    530                 535                 540
Glu Trp Ser Asp Arg Asn Val Thr Phe Thr Thr Ile Asn Met Pro Leu
545                 550                 555                 560
Val Lys Thr Pro Met Ile Ala Pro Thr Lys Ile Tyr Asp Ser Val Pro
                565                 570                 575
Thr Leu Thr Pro Asp Glu Ala Ala Gln Met Val Ala Asp Ala Ile Val
            580                 585                 590
```

```
Tyr Arg Pro Lys Arg Ile Ala Thr Arg Leu Gly Val Phe Ala Gln Val
            595                 600                 605

Leu His Ala Leu Ala Pro Lys Met Gly Glu Ile Ile Met Asn Thr Gly
    610                 615                 620

Tyr Arg Met Phe Pro Asp Ser Pro Ala Ala Gly Ser Lys Ser Gly
625                 630                 635                 640

Glu Lys Pro Lys Val Ser Thr Glu Gln Val Ala Phe Ala Ala Ile Met
                645                 650                 655

Arg Gly Ile Tyr Trp
            660

<210> SEQ ID NO 12
<211> LENGTH: 1986
<212> TYPE: DNA
<213> ORGANISM: Marinobacter aquaeoli VT8

<400> SEQUENCE: 12
```

| | | | | |
|---|---|---|---|---|
| ttaccagtat | atccccgca | taatcgccgc | aaaggccacc | tgctcggtag agactttcgg | 60 |
| cttttcgccg | gacttgctgc | cagcggctgc | tggagaatcc | gggaacatcc ggtagccagt | 120 |
| gttcataatg | atctcaccca | tcttcggtgc | cagcgcatgc | agaacctgcg cgaacacgcc | 180 |
| aagacgggtg | gcaatgcgct | tgggccggta | cacaatcgca | tccgccacca tctgggcggc | 240 |
| ttcatccggc | gtcagcgtcg | gcacggaatc | gtagatcttg | gtgggcgcga tcatcggcgt | 300 |
| tttcaccaac | ggcatgttga | tggtggtgaa | ggtcacgttg | cgatccgacc attctgcagc | 360 |
| ggcacagcgg | ctgaacgcgt | ccagtgcgga | tttcgaggag | acataggccg agaaacgcgg | 420 |
| agcgttggta | agtaccccga | tggaagaaat | attcaccacg | tgcccgcggc gacgctccag | 480 |
| catggctggc | gcaaagccca | tgatcagccg | aacggagcca | agtagttca gctgcatggt | 540 |
| ccgctcaaaa | tcgtggaacc | ggtcaaaaga | caacgccagc | gagcggcgga tggagcgacc | 600 |
| cgcgttattc | accagtacat | ccacgtggcc | gtgattatcc | agcaccgtct tcacaaagcg | 660 |
| gtcgcagtcg | tccatgtccg | aaaagtcgca | ctggtacgca | tgcacgttgc cacccttggc | 720 |
| ctccagactg | gccgccactt | catccagagt | ttccttggtg | cgcgcaccaa tgaccagaat | 780 |
| ggcaccggcc | tctgccagct | tctctgccgt | tgccaggcca | ataccgagg tcgcgccggt | 840 |
| gaccacgcaa | accttacctt | caaccgtgcc | cttgagggtg | cggtccttga acaggtccgg | 900 |
| gtccagattg | cgctcccagt | agtcccagat | aaccggggca | taggacggca gacgcggcac | 960 |
| ctcaatgtct | gtgcccttca | gaacccgctc | cagctcccgg | gtatcaaaac gggtcgggta | 1020 |
| attaatgaag | gacatcaccg | agggcggaat | gcccatgtca | tccagaagcg caccagtaat | 1080 |
| gcgcttgacc | ggaggcagat | tcttgatgct | ctggcgaata | acggcggaa taaaaccgaa | 1140 |
| catccgggaa | tcgatgcgca | tacccatgcg | ggggcatgg | ccggcctcgc agaaaatatt | 1200 |
| gaggatctca | cccaccttat | acggatcgga | gtccaccaga | tggaaacagt tgccatcttc | 1260 |
| gccttccaga | tgggcaatgt | gatccagtgc | atcgaccacg | aaatccaccg gcacaatgtt | 1320 |
| cagccggcca | ccttcaatac | cgatggtggg | tacccactgg | ggcaacgcat gacggatctt | 1380 |
| ctgaatcatc | ttgaagaagt | aatagggccc | gtcaaccttg | tccatttcgc cggtttccga | 1440 |
| atggccaatg | accataccag | ggcggtagat | gcggaacgga | accttgcatt cttcacgcac | 1500 |
| aacttttcg | gattcgtgct | tggtgcgcag | gtaaggatga | tcaagcttct cggcttcttc | 1560 |
| gaacatatcc | tcccggaaga | tacccttgaa | cagacccgct | gccgcgatgg atgacacatg | 1620 |
| atggaaatgc | ttggcgccca | tggcttcggc | ggcctgaaca | gccgccctgg tgccttcgat | 1680 |
| attggtggcg | gcctgggctt | cttcgtctgc | gcccatgtcg | tagaccgcgg caagatggaa | 1740 |

-continued

```
tacgtggtcg atatttcctt tcagtgattt cagcgttttc gcgtcaatac caaggttttt   1800
gctggtgagg tcgccgatca cagccttcac ttgcttgtcg tctgcacccc agcgctcccg   1860
gagccgctcc agcttgtcct gggactgctc gcgaaccaga acatacacgg tgccgccgcg   1920
cgccaagagt ttctcaacca gaaaacgacc gataaaaccg gtgccgcctg tcaggaaata   1980
attcat                                                               1986
```

<210> SEQ ID NO 13
<211> LENGTH: 3192
<212> TYPE: DNA
<213> ORGANISM: Artificial sequence
<220> FEATURE:
<223> OTHER INFORMATION: Synthetic construct: FadD-CER4 operon

<400> SEQUENCE: 13

```
atggccaaga aggtttggct taaccgttat cccgcggacg ttccgacgga gatcaaccct    60
gaccgttatc aatctctggt agatatgttt gagcagtcgg tcgcgcgcta cgccgatcaa   120
cctgcgtttg tgaatatggg ggaggtaatg accttccgca agctggaaga acgcagtcgc   180
gcgtttgccg cttatttgca acaagggttg gggctgaaga aaggcgatcg cgttgcgttg   240
atgatgccta atttattgca atatccggtg gcgctgtttg gcattttgcg tgccgggatg   300
atcgtcgtaa acgttaaccc gttgtatacc ccgcgtgagc ttgagcatca gcttaacgat   360
agcggcgcat cggcgattgt tatcgtgtct aactttgctc acacactgga aaaagtggtt   420
gataaaaccg ccgttcagca cgtaattctg accgtatatgg gcgatcagct atctacggca   480
aaaggcacgg tagtcaattt cgttgttaaa tacatcaagc gtttggtgcc gaaataccat   540
ctgccagatg ccatttcatt tcgtagcgca ctgcataacg gctaccggat gcagtacgtc   600
aaacccgaac tggtgccgga agatttagct tttctgcaat acaccggcgg caccactggt   660
gtggcgaaag cgcgatgct gactcaccgc aatatgctgg cgaacctgga acaggttaac   720
gcgacctatg gtccgctgtt gcatccgggc aaagagctgg tggtgacggc gctgccgctg   780
tatcacattt ttgcccctgac cattaactgc ctgctgttta tcgaactggg tgggcagaac   840
ctgcttatca ctaacccgcg cgatattcca gggttggtaa aagagttagc gaaatatccg   900
tttaccgcta tcacgggcgt taacaccttg ttcaatgcgt tgctgaacaa taaagagttc   960
cagcagctgg atttctccag tctgcatctt tccgcaggcg gtgggatgcc agtgcagcaa  1020
gtggtggcag agcgttgggt gaaactgacc ggacagtatc tgctggaagg ctatggcctt  1080
accgagtgtg cgccgctggt cagcgttaac ccatatgata ttgattatca tagtggtagc  1140
atcggtttgc cggtgccgtc gacggaagcc aaactggtgg atgatgatga taatgaagta  1200
ccaccaggtc aaccgggtga gctttgtgtc aaaggaccgc aggtgatgct gggttactgg  1260
cagcgtcccg atgctaccga tgaaatcatc aaaaatggct ggttacacac cggcgacatc  1320
gcggtaatgg atgaagaagg attcctgcgc attgtcgatc gtaaaaaga catgattctg  1380 gtttccggtt ttaacgtcta tcccaacgag attgaagatg tcgtcatgca gcatcctggc  1440
gtacaggaag tcgcggctgt tggcgtacct tccggctcca gtggtgaagc ggtgaaaatc  1500
ttcgtagtga aaaagatcc atcgcttacc gaagagtcac tggtgacttt ttgccgccgt  1560
cagctcacgg gatacaaagt accgaagctg gtggagtttc gtgatgagtt accgaaatct  1620
aacgtcggaa aaattttgcg acgagaatta cgtgacgaag cgcgcggcaa agtggacaat  1680
aaagcctgag gatcctaagg aggaaaaaaa atgtcgacag aaatggaggt cgttagtgtt  1740
cttaagtacc ttgacaacaa atccatattg gtcgttggag ctgctgggtt cttagcaaat  1800
```

```
atctttgtgg agaagatatt aagggtggca ccaaacgtga agaaactcta tctccttcta    1860
agagcatcaa aaggaaaatc tgctacccag aggtttaacg acgagatttt gaagaaagat    1920
ttgttcaagg tgctgaagga aagtatggt cccaatctaa atcaacttac atcagagaaa    1980
atcactattg tcgacggaga catttgcctt gaggatttag gtcttcaaga cttcgacttg    2040
gctcatgaga tgatccacca agttgatgcc attgttaatt tagctgcaac tactaagttt    2100
gatgaaagat acgatgtagc tcttgggatc aacacattgg gtgctctcaa tgtcttgaac    2160
tttgccaaga gatgtgcaaa ggttaagatc cttgttcatg tatcaacagc ttacgtgtgc    2220
ggagaaaaat ctggcttgat aatggaaaca ccgtaccgta tgggtgagac gttgaatgga    2280
accaccggtt tagacatcaa ctacgagaaa aaattggttc aggagaaact tgaccagctc    2340
cgagtaatcg gagccgctcc tgaaaccatc acggaaacca tgaaggatct cggactcaga    2400
cgggcaaaga tgtacggatg gccaaacaca tatgtgttca ccaaagcaat ggggagatg    2460 atggtaggga caaaaagaga aaatctgtca cttgtgttgc ttcgtccttc aattattacc    2520
agcacattca agaaccatt tcctggttgg actgagggca tcaggactat tgatagttta    2580
gctgttggat atggcaaagg caaactcacg tgcttcctct gtgatcttga tgctgtttct    2640
gatgtgatgc cggcagatat ggtagtaaat tcgattcttg tatcaatggc cgctcaagcc    2700
ggtaaacaag aagagattat ttaccatgtg ggttcttcac ttagaaatcc gatgaaaaat    2760
tcaaagtttc ctgaattagc gtatcggtat ttctcaatca aaccgtggac caacaaagaa    2820
gggaaggtcg ttaaggtcgg ggccattgag atcctgagtt ctatgcgtag tttccataga    2880
tacatgacca tacgctactt gattgcattg aagggacttg aattggtaaa cataatactt    2940
tgcaagttgt ttgagaagga atttcagtat ttcaataaga aaataaattt tatattccgg    3000
cttgttgatc tctatcagcc ttacctcttt ttctatggaa tatttgatga ttcaaacaca    3060
gaaaaattgc gaaaaatggt atcgaagacg ggagtcgaaa acgagatgtt ttatttcgat    3120
ccaaaggttc tcgattggga cgactatttt ttgaacacac atgttattgg gctgcttaag    3180
tatgtcttct aa                                                       3192
```

<210> SEQ ID NO 14
<211> LENGTH: 1112
<212> TYPE: DNA
<213> ORGANISM: Artificial sequence
<220> FEATURE:
<223> OTHER INFORMATION: Synthetic construct: Cc1FatB1 sequence codon-optimized for Synechocystis

<400> SEQUENCE: 14

```
atggcgaacg gtagcgctgt ctctctgaag agcggctcct tgaatacgca agaggacact      60
tcttcttccc caccgccacg cgcgttcatc aaccaattac ccgactggtc catgttattg     120
acggcgatta ccactgtctt tgttgccgca gagaaacagt ggactatgtt agaccgcaag     180
agcaagcgct ccgatatgtt agtggattct ttggcatgg aacgcattgt gcaggatggc     240
ttagtgtttc gtcaatcttt tagcattcgt tcttatgaaa tcggtgcaga tcgtcgtgca     300
tccattgaaa ccttaatgaa ccatctgcag gaaactagct tgaatcattg caaatccatt     360
cgcttgttga tgagggttt tggtcgcacc ccgagatgt gcaaacgtga cttgatctgg     420
gtggttaccc gcatgcacat catggtcaac cgctacccta cctgggtgta taccgttgag     480
attaacactt gggtttccca aagcggcaag aatggtatgg tcgtgattg gctgatttcc     540 gactgtaata ccggcgaaat cctgatccgc gcgacgtctg catgggcgat gatgaaccaa     600
```

```
aagacccgtc gtctgtctaa actgccttac gaagtcagcc aagagattgc tccgcacttc    660
gtcgacagcc ctcccgtgat cgaggacggc gaccgtaagt tacacaagtt cgatgtgaaa    720
accggcgaca gcatccgtaa aggtttgact ccgcgttgga atgacttaga tgttaatcag    780
cacgttaaca acgttaagta tatcggctgg atcttagaga gcatgccgac cgaggtcttg    840
gaaactcatg aactgtgttt cttaactctg gagtatcgtc gcgagtgcgg tcgcgatagc    900
gtgctggaat ctgtgaccgc gatggatcct tctaatgaag gtggtcgctc ccactaccag    960
catttactgc gcttggagga cggtactgac atcgttaagg gccgcactga gtggcgtcca   1020
aagaatgccc ggaatattgg tgccattagt accggtaaaa ccagtaatgg taatcccgcc   1080
agttaataat gatcagatcc ggagtttgta ga                                 1112
```

<210> SEQ ID NO 15
<211> LENGTH: 361
<212> TYPE: PRT
<213> ORGANISM: Artificial sequence
<220> FEATURE:
<223> OTHER INFORMATION: Synthetic construct: CclFatB1 thioesterase
      protein encoded by expression construct

<400> SEQUENCE: 15

```
Met Ala Asn Gly Ser Ala Val Ser Leu Lys Ser Gly Ser Leu Asn Thr
1               5                   10                  15

Gln Glu Asp Thr Ser Ser Ser Pro Pro Arg Ala Phe Ile Asn Gln
            20                  25                  30

Leu Pro Asp Trp Ser Met Leu Leu Thr Ala Ile Thr Thr Val Phe Val
        35                  40                  45

Ala Ala Glu Lys Gln Trp Thr Met Leu Asp Arg Lys Ser Lys Arg Ser
    50                  55                  60

Asp Met Leu Val Asp Ser Phe Gly Met Glu Arg Ile Val Gln Asp Gly
65                  70                  75                  80

Leu Val Phe Arg Gln Ser Phe Ser Ile Arg Ser Tyr Glu Ile Gly Ala
                85                  90                  95

Asp Arg Arg Ala Ser Ile Glu Thr Leu Met Asn His Leu Gln Glu Thr
            100                 105                 110

Ser Leu Asn His Cys Lys Ser Ile Arg Leu Leu Asn Glu Gly Phe Gly
        115                 120                 125

Arg Thr Pro Glu Met Cys Lys Arg Asp Leu Ile Trp Val Val Thr Arg
    130                 135                 140

Met His Ile Met Val Asn Arg Tyr Pro Thr Trp Gly Asp Thr Val Glu
145                 150                 155                 160

Ile Asn Thr Trp Val Ser Gln Ser Gly Lys Asn Gly Met Gly Arg Asp
                165                 170                 175

Trp Leu Ile Ser Asp Cys Asn Thr Gly Glu Ile Leu Ile Arg Ala Thr
            180                 185                 190

Ser Ala Trp Ala Met Met Asn Gln Lys Thr Arg Arg Leu Ser Lys Leu
        195                 200                 205

Pro Tyr Glu Val Ser Gln Glu Ile Ala Pro His Phe Val Asp Ser Pro
    210                 215                 220

Pro Val Ile Glu Asp Gly Asp Arg Lys Leu His Lys Phe Asp Val Lys
225                 230                 235                 240

Thr Gly Asp Ser Ile Arg Lys Gly Leu Thr Pro Arg Trp Asn Asp Leu
                245                 250                 255

Asp Val Asn Gln His Val Asn Asn Val Lys Tyr Ile Gly Trp Ile Leu
            260                 265                 270
```

```
Glu Ser Met Pro Thr Glu Val Leu Glu Thr His Glu Leu Cys Phe Leu
    275                 280                 285

Thr Leu Glu Tyr Arg Arg Glu Cys Gly Arg Asp Ser Val Leu Glu Ser
    290                 295                 300

Val Thr Ala Met Asp Pro Ser Asn Glu Gly Gly Arg Ser His Tyr Gln
305                 310                 315                 320

His Leu Leu Arg Leu Glu Asp Gly Thr Asp Ile Val Lys Gly Arg Thr
                325                 330                 335

Glu Trp Arg Pro Lys Asn Ala Arg Asn Ile Gly Ala Ile Ser Thr Gly
            340                 345                 350

Lys Thr Ser Asn Gly Asn Pro Ala Ser
            355                 360

<210> SEQ ID NO 16
<211> LENGTH: 2595
<212> TYPE: DNA
<213> ORGANISM: Artificial sequence
<220> FEATURE:
<223> OTHER INFORMATION: Synthetic construct: LuxC-LuxE operon

<400> SEQUENCE: 16
atgactaaaa aaatttcatt cattattaac ggccaggttg aaatctttcc cgaaagtgat      60
gatttagtgc aatccattaa ttttggtgat aatagtgttt acctgccaat attgaatgac    120
tctcatgtaa aaacattat tgattgtaat ggaaataacg aattacggtt gcataacatt     180
gtcaattttc tctatacggt agggcaaaga tggaaaaatg aagaatactc aagacgcagg    240
acatacattc gtgacttaaa aaatatatg ggatattcag aagaaatggc taagctagag     300
gccaattgga tatctatgat tttatgttct aaaggcggcc tttatgatgt tgtagaaaat    360
gaacttggtt ctcgccatat catggatgaa tggctacctc aggatgaaag ttatgttcgg    420
gcttttccga aggtaaaatc tgtacatctg ttggcaggta atgttccatt atctgggatc    480
atgtctatat tacgcgcaat tttaactaag aatcagtgta ttataaaaac atcgtcaacc    540
gatcctttta ccgctaatgc attagcgtta agttttattg atgtagaccc taatcatccg    600
ataacgcgct ctttatctgt tatatattgg ccccaccaag gtgatacatc actcgcaaaa    660
gaaattatgc acatgcgga tgttattgtc gcttggggag ggccagatgc gattaattgg    720
gcggtagagc atgcgccatc ttatgctgat gtgattaaat ttggttctaa aaagagtctt    780
tgcattatcg ataatcctgt tgatttgacg tccgcagcga caggtgcggc tcatgatgtt    840 tgttttacg atcagcgagc ttgttttct gcccaaaaca tatattacat gggaaatcat    900
tatgaggaat ttaagttagc gttgatagaa aaacttaatc tatatgcgca tatattaccg    960
aatgccaaaa aagattttga tgaaaaggcg gcctattctt tagttcaaaa agaaagcttg   1020
tttgctggat taaaagtaga ggtggatatt catcaacgtt ggatgattat tgagtcaaat   1080
gcaggtgtgg aatttaatca accacttggc agatgtgtgt accttcatca cgtcgataat   1140
attgagcaaa tattgcctta tgttcaaaaa ataagacgc aaaccatatc tattttttcct   1200 tgggagtcat catttaaata tcgagatgcg ttagcattaa aaggtgcgga aaggattgta   1260
gaagcaggaa tgaataacat atttcgagtt ggtggatctc atgacggaat gagaccgttg   1320
caacgattag tgcatatat ttctcatgaa aggccatcta actatacggc taaggatgtt   1380
gcggttgaaa tagaacagac tcgattcctg gaagaagata agttccttgt atttgtccca   1440
taaaagcttg catgcctgca ggtcgacagg aggatcatta ctatgacttc atatgttgat   1500
aaacaagaaa ttacagcaag ctcagaaatt gatgatttga ttttttcgag cgatccatta   1560
```

-continued

```
gtgtggtctt acgacgagca ggaaaaaatc agaagaaac ttgtgcttga tgcatttcgt      1620
aatcattata aacattgtcg agaatatcgt cactactgtc aggcacacaa agtagatgac      1680
aatattacgg aaattgatga catacctgta ttcccaacat cggttttta gtttactcgc      1740 ttattaactt ctcaggaaaa cgagattgaa agttggttta ccagtagcgg cacgaatggt      1800
ttaaaaagtc aggtggcgcg tgacagatta agtattgaga gactcttagg ctctgtgagt      1860
tatggcatga aatatgttgg tagttggttt gatcatcaaa tagaattagt caatttggga      1920
ccagatagat ttaatgctca taatatttgg tttaaatatg ttatgagttt ggtggaattg      1980
ttatatccta cgacatttac cgtaacagaa gaacgaatag attttgttaa acattgaat       2040 agtcttgaac gaataaaaaa tcaagggaaa gatctttgtc ttattggttc gccatacttt      2100
atttatttac tctgccatta tatgaaagat aaaaaaatct catttctgg agataaaagc       2160 ctttatatca taaccggagg cggctggaaa agttacgaaa agaatctct gaaacgtgat        2220 gatttcaatc atcttttatt tgatactttc aatctcagtg atattagtca gatccgagat      2280
atatttaatc aagttgaact caacacttgt ttctttgagg atgaaatgca gcgtaaacat      2340
gttccgccgt gggtatatgc gcgagcgctt gatcctgaaa cgttgaaacc tgtacctgat      2400
ggaacgccgg ggttgatgag ttatatggat gcgtcagcaa ccagttatcc agcatttatt      2460
gttaccgatg atgtcgggat aattagcaga gaatatggta agtatcccgg cgtgctcgtt      2520 gaaatttac gtcgcgtcaa tacgaggacg cagaaagggt gtgctttaag cttaaccgaa       2580
gcgtttgata gttga                                                       2595
```

<210> SEQ ID NO 17
<211> LENGTH: 4164
<212> TYPE: DNA
<213> ORGANISM: Artificial sequence
<220> FEATURE:
<223> OTHER INFORMATION: Synthetic construct: LuxCE-Maqu_2220 operon

<400> SEQUENCE: 17

```
atgactaaaa aaatttcatt cattattaac ggccaggttg aaatctttcc cgaaagtgat       60
gatttagtgc aatccattaa ttttggtgat aatagtgttt acctgccaat attgaatgac       120
tctcatgtaa aaacattat tgattgtaat ggaaataacg aattacggtt gcataacatt       180
gtcaattttc tctatacggt agggcaaaga tggaaaaatg aagaatactc aagacgcagg       240
acatacattc gtgacttaaa aaaatatatg ggatattcag aagaaatggc taagctagag       300
gccaattgga tatctatgat tttatgttct aaaggcggcc tttatgatgt tgtagaaaat       360
gaacttggtt ctcgccatat catggatgaa tggctacctc aggatgaaag ttatgttcgg       420
gcttttccga aggtaaatc tgtacatctg ttggcaggta atgttccatt atctgggatc       480
atgtctatat tacgcgcaat tttaactaag aatcagtgta ttataaaaac atcgtcaacc       540
gatcctttta ccgctaatgc attagcgtta agttttattg atgtagaccc taatcatccg       600
ataacgcgct ctttatctgt tatatattgg ccccaccaag gtgatacatc actcgcaaaa       660
gaaattatgc gacatgcgga tgttattgtc gcttggggag ggccagatgc gattaattgg       720
gcggtagagc atgcgccatc ttatgctgat gtgattaaat ttggttctaa aaagagtctt      780
tgcattatcg ataatcctgt tgatttgacg tccgcagcga caggtgcggc tcatgatgtt      840 tgttttacg atcagcgagc ttgtttttct gcccaaaaca tattaacat gggaaatcat        900 tatgaggaat ttaagttagc gttgatagaa aaacttaatc tatatgcgca tatattaccg       960
aatgccaaaa aagattttga tgaaaaggcg gcctattctt tagttcaaaa agaaagcttg      1020
```

```
tttgctggat taaaagtaga ggtggatatt catcaacgtt ggatgattat tgagtcaaat    1080
gcaggtgtgg aatttaatca accacttggc agatgtgtgt accttcatca cgtcgataat    1140
attgagcaaa tattgcctta tgttcaaaaa aataagacgc aaaccatatc tatttttcct    1200
tgggagtcat catttaaata tcgagatgcg ttagcattaa aaggtgcgga aaggattgta    1260
gaagcaggaa tgaataacat atttcgagtt ggtggatctc atgacggaat gagaccgttg    1320
caacgattag tgcatatat ttctcatgaa aggccatcta actatacggc taaggatgtt    1380
gcggttgaaa tagaacagac tcgattcctg aagaagata agttccttgt atttgtccca    1440
taaaagcttg catgcctgca ggtcgacagg aggatcatta ctatgacttc atatgttgat    1500
aaacaagaaa ttacagcaag ctcagaaatt gatgatttga ttttttcgag cgatccatta    1560
gtgtggtctt acgacgagca ggaaaaaatc agaaagaaac ttgtgcttga tgcatttcgt    1620
aatcattata acattgtcg agaatatcgt cactactgtc aggcacacaa agtagatgac    1680
aatattacgg aaattgatga catacctgta ttcccaacat cggttttaa gtttactcgc    1740 ttattaactt ctcaggaaaa cgagattgaa agttggttta ccagtagcgg cacgaatggt    1800
ttaaaaagtc aggtggcgcg tgacagatta agtattgaga gactcttagg ctctgtgagt    1860
tatggcatga aatatgttgg tagttggttt gatcatcaaa tagaattagt caatttggga    1920
ccagatagat ttaatgctca taatatttgg tttaaatatg ttatgagttt ggtggaattg    1980
ttatatccta cgacatttac cgtaacagaa gaacgaatag attttgttaa aacattgaat    2040
agtcttgaac gaataaaaaa tcaagggaaa gatctttgtc ttattggttc gccatacttt    2100
atttatttac tctgccatta tatgaaagat aaaaaaatct cattttctgg agataaaagc    2160
ctttatatca taaccggagg cggctggaaa agttacgaaa aagaatctct gaaacgtgat    2220
gatttcaatc atctttatt tgatactttc aatctcagtg atattagtca gatccgagat    2280
atatttaatc aagttgaact caacacttgt ttctttgagg atgaaatgca gcgtaaacat    2340
gttccgccgt gggtatatgc gcgagcgctt gatcctgaaa cgttgaaacc tgtacctgat    2400
ggaacgccgg ggttgatgag ttatatggat gcgtcagcaa ccagttatcc agcatttatt    2460
gttaccgatg atgtcgggat aattagcaga gaatatggta agtatcccgg cgtgctcgtt    2520
gaaattttac gtcgcgtcaa tacgaggacg cagaaagggt gtgctttaag cttaaccgaa    2580
gcgtttgata gttgagtcga ctctagaagg aggatcatta ctatggcaat acagcaggta    2640
catcacgctg acacttcatc atcaaaggtg ctcggacagc tccgtggcaa gcgggttctg    2700
atcaccggta ccactggctt tctgggcaag gtggtcctcg aaaggctgat tcgggcggtg    2760
cctgatatcg gcgcaattta cctgctgatc cggggcaata aacggcatcc ggatgctcgt    2820 tcccgttttcc tggaagaaat tgccacctcc tcggtgtttg accgtcttcg cgaggccgat    2880
tcagagggat ttgacgcctt tctggaagag cgcattcact gcgtgaccgg tgaggtgacc    2940
gaagcgggtt tcgggatagg cagaggaagac tatcgcaaac tcgccaccga actggatgcg    3000
gtgatcaact ccgctgcaag cgtgaatttc cgtgaagagc tcgacaaggc gctggccatc    3060
aacaccctgt gccttcggaa tattgccggc atggtggatt tgaatccgaa gcttgcggtc    3120
ctgcaggtct ccacctgcta tgtcaatggc atgaactcgg ggcaggtaac cgaatcggtg    3180
atcaagccgg caggcgaggc cgtgccgcgt tccccgacg gcttctatga gatagaagag    3240
cttgttcgcc tgcttcagga taaaattgaa gacgttcagg cccgttattc cggcaaagtg    3300
ctggagagga agctggtgga cctggggatt cgggaagcca accgctatgg ctggagcgat    3360
acctacacct ttaccaagtg gctgggcgaa cagttgctga tgaaggcgtt aaacgggcgc    3420
```

| | |
|---|---|
| acgctgacca ttctgcgtcc ttcgattatc gaaagtgccc tggaggaacc agcgcccggc | 3480 |
| tggattgagg gggtgaaggt ggcagatgcc atcatcctgg cttacgcacg ggaaaaagtc | 3540 |
| accctcttcc cgggcaaacg ctccggtatc atcgatgtga ttccagtgga cctggtggcc | 3600 |
| aactccatca tcctttccct ggcggaagct cttggagaac ccggtcgacg tcgcatctat | 3660 |
| caatgttgca gcggggcgg caatccaatc tccctgggtg agttcatcga tcatctcatg | 3720 |
| gcggaatcaa aagccaatta cgctgcctac gatcacctgt tctaccggca gcccagcaag | 3780 |
| ccgtttctgg cggttaaccg ggcgctgttt gatttggtga tcagtggtgt tcgcttaccg | 3840 |
| ctctccctga cggaccgtgt gctcaaatta ctgggaaatt cccgggacct gaaaatgctc | 3900 |
| aggaatctgg ataccaccca gtcgctggca accattttg gtttctacac cgcgccggat | 3960 |
| tatatcttcc ggaacgatga gctgatgcg ctggcgaacc ggatgggtga ggtcgataaa | 4020 |
| gggctgttcc cggtggatgc ccgcctgatt gactgggagc tctacctgcg caagattcac | 4080 |
| ctggccgggc tcaatcgcta tgccctgaaa gaacgaaagg tgtacagtct gaaaaccgcg | 4140 |
| cgccagcgca aaaaagctgc ctga | 4164 |

<210> SEQ ID NO 18
<211> LENGTH: 2308
<212> TYPE: DNA
<213> ORGANISM: Arabidopsis thaliana

<400> SEQUENCE: 18

| | |
|---|---|
| ataataacct agacgaagaa caaacaaaac tctctctttc tctctctctc tctaataagt | 60 |
| aaggttttga tcttttttcaa gatcaaacaa aaacaatgga gttagagagt acgagcaatg | 120 |
| gccgacgtcc gccgccaccg gcagagattg gccgtgggc gtacttggcg tgggaagatt | 180 |
| tgacggtggt tataccaaac tttagtggtg gtccgactcg aagattgctc gatggattaa | 240 |
| acggtcatgc tgaaccaggt cggattatgg ccattatggg tccttccgga tccggcaagt | 300 |
| ccacgcttct tgattctctc gcaggtagac tcgcaagaaa cgtgattatg accggtaatc | 360 |
| ttctattgaa cggaaagaag gcaagactag actacggtct cgtcgcttat gtaacacaag | 420 |
| aggacatttt tgatgggaaca ctaacggtga gggagacaat aacatactca gctcatctac | 480 |
| ggctatcaag tgatttgacc aaagaagaag tcaacgacat tgttgaagga caatcattg | 540 |
| aacttggtct tcaagattgt gcagacagag tcataggtaa ttggcattct agaggagtga | 600 |
| gtggcggcga gaggaaacgc gtcagcgttg cgttagagat cttaacgcga ccgcaaattt | 660 |
| tgtttcttga tgaacctact agtggtttgg acagtgcttc tgctttcttt gtgattcaag | 720 |
| cgctaaggaa tatcgctcga gatggtggta gaaccgttgt ttcatcgatt catcaaccta | 780 |
| gtagcgaagt ttttgctctc tttgatgatc ttttttttgct ctctagtggt gagactgttt | 840 |
| attttggtga atccaagttt gctgttgagt tctttgctga agcggggttt ccttgcccga | 900 |
| agaaacggaa tccttctgat catttcctaa gatgtatcaa ctcagacttt gataccgtta | 960 |
| cagctacact caaaggatct caaaggattc gggagacacc agctacatca gatcctttga | 1020 |
| tgaatctagc aacatctgag atcaaagcta ggcttgttga gaattatcgt cgttcagtct | 1080 |
| acgctaaatc tgcaaaatct cgcatccgtg aattagctag cattgaagga catcatggga | 1140 |
| tggaagtgag aaagggaagc gaagcgacgt ggtttaagca gctaagaact ttgacaaaga | 1200 |
| gatcatttgt gaacatgtgc cgcgatattg gatactattg gtcaagaatt gtgatctata | 1260 |
| ttgtggtatc attctgtgtt gggacaatct tttacgatgt aggacatagc tacacatcga | 1320 |
| tcttggctcg ggtttcttgt ggtggattca ttaccggttt catgactttc atgtccattg | 1380 |

-continued

```
gagggtttcc ttctttcatt gaagaaatga aagtgttcta taaagagaga ttgagtggtt    1440
actacggcgt ttcggtttat atcatatcga attacgtctc ttctttcccg ttcttggtag    1500
ccattgcgct catcacaggg agtattactt acaacatggt gaaattccgt cctggtgtct    1560
cgcattgggc tttcttctgt ctcaacatat tcttctctgt ctccgtcatt gagagtctca    1620
tgatggttgt ggcttctctt gttccgaatt tcttgatggg tcttatcaca ggagctggca    1680
tcattggaat catcatgatg acttctggat tcttccgttt gcttcccgat ctgccaaagg    1740
ttttctggcg ctacccgatt tccttcatga gttatggttc ttgggctatt cagggagcat    1800
acaagaatga ttttcttggt ctagagtttg acccgatgtt tgcggggggaa ccaaagatga    1860 caggagagca agtgataaac aagatatttg gagtgcaagt cacacattct aagtggtggg    1920
acttatcagc gatcgtgttg atccttgtgt gttaccgcat tctattttc atagtcttga    1980 agcttaagga gagagcagag ccggctttga aggcgataca agcaaagcga acgatgaaga    2040
gtctcaaaaa gagaccttct ttcaagaaag ttccatctct atcatcacta tcttcaagga    2100
gacaccaacc tctacattca ctttcttctc aagaaggtct tacctctcca attaattaaa    2160
gattatatct atttgtgtat acactttgtt tcttaatttg ttttgcacat acgatagttt    2220
caacatttat aaatatgtat cattatcagc atctaatgat tctatgattc agcattgtta    2280
tttttggaga ataaacatga tactctgt                                       2308
```

<210> SEQ ID NO 19
<211> LENGTH: 687
<212> TYPE: PRT
<213> ORGANISM: Arabidopsis thaliana

<400> SEQUENCE: 19

```
Met Glu Leu Glu Ser Thr Ser Asn Gly Arg Arg Pro Pro Pro Ala
1               5                   10                  15

Glu Ile Gly Arg Gly Ala Tyr Leu Ala Trp Glu Asp Leu Thr Val Val
            20                  25                  30

Ile Pro Asn Phe Ser Gly Gly Pro Thr Arg Arg Leu Leu Asp Gly Leu
        35                  40                  45

Asn Gly His Ala Glu Pro Gly Arg Ile Met Ala Ile Met Gly Pro Ser
    50                  55                  60

Gly Ser Gly Lys Ser Thr Leu Leu Asp Ser Leu Ala Gly Arg Leu Ala
65                  70                  75                  80

Arg Asn Val Ile Met Thr Gly Asn Leu Leu Leu Asn Gly Lys Lys Ala
                85                  90                  95

Arg Leu Asp Tyr Gly Leu Val Ala Tyr Val Thr Gln Glu Asp Ile Leu
            100                 105                 110

Met Gly Thr Leu Thr Val Arg Glu Thr Ile Thr Tyr Ser Ala His Leu
        115                 120                 125

Arg Leu Ser Ser Asp Leu Thr Lys Glu Val Asn Asp Ile Val Glu
    130                 135                 140

Gly Thr Ile Ile Glu Leu Gly Leu Gln Asp Cys Ala Asp Arg Val Ile
145                 150                 155                 160

Gly Asn Trp His Ser Arg Gly Val Ser Gly Glu Arg Lys Arg Val
                165                 170                 175

Ser Val Ala Leu Glu Ile Leu Thr Arg Pro Gln Ile Leu Phe Leu Asp
            180                 185                 190

Glu Pro Thr Ser Gly Leu Asp Ser Ala Ser Ala Phe Phe Val Ile Gln
        195                 200                 205

Ala Leu Arg Asn Ile Ala Arg Asp Gly Gly Arg Thr Val Val Ser Ser
```

```
                210                 215                 220
Ile His Gln Pro Ser Ser Glu Val Phe Ala Leu Phe Asp Asp Leu Phe
225                 230                 235                 240

Leu Leu Ser Ser Gly Glu Thr Val Tyr Phe Gly Glu Ser Lys Phe Ala
                245                 250                 255

Val Glu Phe Phe Ala Glu Ala Gly Phe Pro Cys Pro Lys Lys Arg Asn
            260                 265                 270

Pro Ser Asp His Phe Leu Arg Cys Ile Asn Ser Asp Phe Asp Thr Val
            275                 280                 285

Thr Ala Thr Leu Lys Gly Ser Gln Arg Ile Arg Glu Thr Pro Ala Thr
290                 295                 300

Ser Asp Pro Leu Met Asn Leu Ala Thr Ser Glu Ile Lys Ala Arg Leu
305                 310                 315                 320

Val Glu Asn Tyr Arg Arg Ser Val Tyr Ala Lys Ser Ala Lys Ser Arg
            325                 330                 335

Ile Arg Glu Leu Ala Ser Ile Glu Gly His His Gly Met Glu Val Arg
            340                 345                 350

Lys Gly Ser Glu Ala Thr Trp Phe Lys Gln Leu Arg Thr Leu Thr Lys
            355                 360                 365

Arg Ser Phe Val Asn Met Cys Arg Asp Ile Gly Tyr Tyr Trp Ser Arg
370                 375                 380

Ile Val Ile Tyr Ile Val Ser Phe Cys Val Gly Thr Ile Phe Tyr
385                 390                 395                 400

Asp Val Gly His Ser Tyr Thr Ser Ile Leu Ala Arg Val Ser Cys Gly
            405                 410                 415

Gly Phe Ile Thr Gly Phe Met Thr Phe Met Ser Ile Gly Gly Phe Pro
            420                 425                 430

Ser Phe Ile Glu Glu Met Lys Val Phe Tyr Lys Glu Arg Leu Ser Gly
            435                 440                 445

Tyr Tyr Gly Val Ser Val Tyr Ile Ile Ser Asn Tyr Val Ser Ser Phe
            450                 455                 460

Pro Phe Leu Val Ala Ile Ala Leu Ile Thr Gly Ser Ile Thr Tyr Asn
465                 470                 475                 480

Met Val Lys Phe Arg Pro Gly Val Ser His Trp Ala Phe Phe Cys Leu
            485                 490                 495

Asn Ile Phe Phe Ser Val Ser Val Ile Glu Ser Leu Met Met Val Val
            500                 505                 510

Ala Ser Leu Val Pro Asn Phe Leu Met Gly Leu Ile Thr Gly Ala Gly
            515                 520                 525

Ile Ile Gly Ile Ile Met Met Thr Ser Gly Phe Phe Arg Leu Leu Pro
530                 535                 540

Asp Leu Pro Lys Val Phe Trp Arg Tyr Pro Ile Ser Phe Met Ser Tyr
545                 550                 555                 560

Gly Ser Trp Ala Ile Gln Gly Ala Tyr Lys Asn Asp Phe Leu Gly Leu
            565                 570                 575

Glu Phe Asp Pro Met Phe Ala Gly Glu Pro Lys Met Thr Gly Glu Gln
            580                 585                 590

Val Ile Asn Lys Ile Phe Gly Val Gln Val Thr His Ser Lys Trp Trp
            595                 600                 605

Asp Leu Ser Ala Ile Val Leu Ile Leu Val Cys Tyr Arg Ile Leu Phe
            610                 615                 620

Phe Ile Val Leu Lys Leu Lys Glu Arg Ala Glu Pro Ala Leu Lys Ala
625                 630                 635                 640
```

```
Ile Gln Ala Lys Arg Thr Met Lys Ser Leu Lys Lys Arg Pro Ser Phe
            645                 650                 655

Lys Lys Val Pro Ser Leu Ser Ser Leu Ser Ser Arg Arg His Gln Pro
                660                 665                 670

Leu His Ser Leu Ser Ser Gln Glu Gly Leu Thr Ser Pro Ile Asn
        675                 680                 685

<210> SEQ ID NO 20
<211> LENGTH: 512
<212> TYPE: PRT
<213> ORGANISM: Marinobacter algicola DG893

<400> SEQUENCE: 20

Met Ala Thr Gln Gln Gln Asn Gly Ala Ser Ala Ser Gly Val Leu
1               5                   10                  15

Glu Gln Leu Arg Gly Lys His Val Leu Ile Thr Gly Thr Thr Gly Phe
                20                  25                  30

Leu Gly Lys Val Val Leu Glu Lys Leu Ile Arg Thr Val Pro Asp Ile
            35                  40                  45

Gly Gly Ile His Leu Leu Ile Arg Gly Asn Lys Arg His Pro Ala Ala
        50                  55                  60

Arg Glu Arg Phe Leu Asn Glu Ile Ala Ser Ser Val Phe Glu Arg
65                  70                  75                  80

Leu Arg His Asp Asp Asn Glu Ala Phe Glu Thr Phe Leu Glu Glu Arg
                85                  90                  95

Val His Cys Ile Thr Gly Glu Val Thr Glu Ser Arg Phe Gly Leu Thr
                100                 105                 110

Pro Glu Arg Phe Arg Ala Leu Ala Gly Gln Val Asp Ala Phe Ile Asn
            115                 120                 125

Ser Ala Ala Ser Val Asn Phe Arg Glu Glu Leu Asp Lys Ala Leu Lys
        130                 135                 140

Ile Asn Thr Leu Cys Leu Glu Asn Val Ala Ala Leu Ala Glu Leu Asn
145                 150                 155                 160

Ser Ala Met Ala Val Ile Gln Val Ser Thr Cys Tyr Val Asn Gly Lys
                165                 170                 175

Asn Ser Gly Gln Ile Thr Glu Ser Val Ile Lys Pro Ala Gly Glu Ser
            180                 185                 190

Ile Pro Arg Ser Thr Asp Gly Tyr Tyr Glu Ile Glu Glu Leu Val His
        195                 200                 205

Leu Leu Gln Asp Lys Ile Ser Asp Val Lys Ala Arg Tyr Ser Gly Lys
        210                 215                 220

Val Leu Glu Lys Lys Leu Val Asp Leu Gly Ile Arg Glu Ala Asn Asn
225                 230                 235                 240

Tyr Gly Trp Ser Asp Thr Tyr Thr Phe Thr Lys Trp Leu Gly Glu Gln
                245                 250                 255

Leu Leu Met Lys Ala Leu Ser Gly Arg Ser Leu Thr Ile Val Arg Pro
            260                 265                 270

Ser Ile Ile Glu Ser Ala Leu Glu Glu Pro Ser Pro Gly Trp Ile Glu
        275                 280                 285

Gly Val Lys Val Ala Asp Ala Ile Ile Leu Ala Tyr Ala Arg Glu Lys
        290                 295                 300

Val Ser Leu Phe Pro Gly Lys Arg Ser Gly Ile Ile Asp Val Ile Pro
305                 310                 315                 320

Val Asp Leu Val Ala Asn Ser Ile Ile Leu Ser Leu Ala Glu Ala Leu
                325                 330                 335
```

-continued

```
Ser Gly Ser Gly Gln Arg Arg Ile Tyr Gln Cys Cys Ser Gly Gly Ser
            340                 345                 350

Asn Pro Ile Ser Leu Gly Lys Phe Ile Asp Tyr Leu Met Ala Glu Ala
        355                 360                 365

Lys Thr Asn Tyr Ala Ala Tyr Asp Gln Leu Phe Tyr Arg Arg Pro Thr
    370                 375                 380

Lys Pro Phe Val Ala Val Asn Arg Lys Leu Phe Asp Val Val Val Gly
385                 390                 395                 400

Gly Met Arg Val Pro Leu Ser Ile Ala Gly Lys Ala Met Arg Leu Ala
                405                 410                 415

Gly Gln Asn Arg Glu Leu Lys Val Leu Lys Asn Leu Asp Thr Thr Arg
            420                 425                 430

Ser Leu Ala Thr Ile Phe Gly Phe Tyr Thr Ala Pro Asp Tyr Ile Phe
        435                 440                 445

Arg Asn Asp Ser Leu Met Ala Leu Ala Ser Arg Met Gly Glu Leu Asp
    450                 455                 460

Arg Val Leu Phe Pro Val Asp Ala Arg Gln Ile Asp Trp Gln Leu Tyr
465                 470                 475                 480

Leu Cys Lys Ile His Leu Gly Gly Leu Asn Arg Tyr Ala Leu Lys Glu
                485                 490                 495

Arg Lys Leu Tyr Ser Leu Arg Ala Ala Asp Thr Arg Lys Lys Ala Ala
            500                 505                 510

<210> SEQ ID NO 21
<211> LENGTH: 1539
<212> TYPE: DNA
<213> ORGANISM: Marinobacter algicola DG893

<400> SEQUENCE: 21
tcaggcggct tttttgcggg tgtcggcggc ccgcaggctg tacagttttc gctccttcag      60
agcgtagcgg ttgagacctc ccaggtggat cttgcacaag tacagctgcc agtcaatctg     120
acgcgcatcc accgggaaca ggacacggtc cagttcaccc atgcgcgaag ccagggccat     180
cagcgaatcg ttacggaaga tgtaatccgg tgccgtgtag aaaccaaaga tggtggccag     240
tgaacgcgtg gtatcgaggt ttttgagaac cttgagctca cggttctggc cagccagcct     300
cattgccttg ccagcaatcg acaacggcac gcgcatgccg ccaaccacaa catcaaacag     360
cttgcgattg accgccacaa acggtttcgt gggccgtcgg tagaacaact ggtcatacgc     420
tgcatagttg gtcttggctt cggccatcag gtagtcaatg aacttgccca gcgaaatcgg     480
attagaaccg ccactgcagc attgatagat gcggcgctgc cctgacccgg aaagggcttc     540
tgccagggac aagatgatac tgttggccac caggtccacc gggatcacat cgataatgcc     600
gctacgcttg cctgggaaca gggagacctt ctcacgggca taggcaagga taatggcgtc     660
tgccaccttc acaccttcaa tccatcctgg cgaaggctct tccagtgcac tttcaatgat     720
ggaagggcga acaatcgtaa gtgaacgccc ggaaagggct tcatcagga gttgctcacc     780 cagccatttg gtaaacgtgt aggtgtcact ccagccgtag ttgttggcct ctcgaatccc     840
caggtccacc agcttttttt caagtacttt gccggagtat cgggctttca cgtcggaaat     900
tttgtcctgc agcaaatgca caagctcttc gatttcatag tagccgtcgg tgctgcgggg     960
aatagactcg cccgccggct tgatgacgga ctccgtgatc tggccggaat cttgccatt    1020 gacgtagcag gtggacacct ggataaccgc catggcgcta ttgagctccg ccagagcggc    1080
aacgttctcc aggcacaggg tgttaatctt cagcgccttg tcgagttcct cccggaagtt    1140
cacactggct gcggaattta taaacgcatc gacctgcccg gcaagtgcac ggaaccgctc    1200
```

```
cggcgtgagc ccgaaacgcg actctgtcac ttcgccggtg atgcagtgaa cgcgttcctc    1260
aagaaaggtt tcaaacgcct cgttgtcatc gtgccgaagg cgttcgaaca cggaagaact    1320
ggcgatctcg ttgaggaatc gttcccgtgc tgcaggatgc cttttgttac cacggataag    1380
aagatggatc ccgccaatat ccggcaccgt gcgaatcaat ttttccagta ccaccttacc    1440
aagaaacccg gtggtgccgg tgatcagcac gtgtttacca cgtagttgct caagaacacc    1500
ggacgctgac gctccgtttt gttgctgctg tgttgccat                           1539
```

<210> SEQ ID NO 22
<211> LENGTH: 505
<212> TYPE: PRT
<213> ORGANISM: Hahella chejuensis KCTC 2396

<400> SEQUENCE: 22

```
Met Lys Gln Ser Leu Thr Leu Thr Ala Phe Ala Asn Lys Asn Val Leu
1               5                   10                  15

Ile Thr Gly Thr Thr Gly Phe Val Gly Lys Val Val Leu Glu Lys Leu
            20                  25                  30

Leu Arg Ser Val Pro Thr Ile Gly Lys Ile Tyr Leu Leu Ile Arg Gly
        35                  40                  45

Asn Ser Lys Asn Pro Thr Ala Arg Lys Arg Phe Gln Asn Glu Ile Ala
    50                  55                  60

Thr Ser Ser Ile Phe Asp Thr Leu Lys Ala Ser Gln Gly Ser Arg Phe
65                  70                  75                  80

Glu Glu Leu Cys Glu Thr Arg Ile His Cys Val Thr Gly Glu Val Thr
                85                  90                  95

Glu Pro Leu Phe Gly Leu Ser Glu Lys Asp Phe Thr Asp Leu Ala Ala
            100                 105                 110

Asp Ile Asp Val Ile Ile Asn Ser Ala Ala Ser Val Asn Phe Arg Glu
        115                 120                 125

Ala Leu Asp Gln Ala Leu Thr Ile Asn Thr Leu Cys Leu Lys Asn Ile
    130                 135                 140

Ile Glu Leu Ser Arg Arg Ala Ala Asp Cys Pro Val Val Gln Val Ser
145                 150                 155                 160

Thr Cys Tyr Val Asn Gly Phe Asn Gln Gly Val Met Glu Glu Ile
                165                 170                 175

Val Ser Pro Ala Gly Glu Arg Ile Glu Arg Ser Glu Arg Gly Tyr Tyr
            180                 185                 190

Glu Val Glu Pro Leu Ile Ala Arg Leu Leu Gln Asp Val Glu Gln Val
        195                 200                 205

Ser Ala Ala Ala Asp Asp His Ser Arg Glu Lys Asp Leu Ile Asp
    210                 215                 220

Leu Gly Ile Lys Glu Ala Asn Lys Tyr Gly Trp Asn Asp Thr Tyr Thr
225                 230                 235                 240

Phe Thr Lys Trp Met Gly Glu Gln Leu Leu Met Lys Glu Leu Tyr Gly
                245                 250                 255

Lys Thr Leu Thr Ile Leu Arg Pro Ser Ile Val Glu Thr Leu Leu
            260                 265                 270

Gly Pro Ala Pro Gly Trp Ile Glu Gly Val Lys Val Ala Asp Ala Ile
        275                 280                 285

Ile Leu Ala Tyr Ala Arg Glu Lys Val Ser Leu Phe Pro Gly Lys Lys
    290                 295                 300

Asn Ala Val Ile Asp Ile Ile Pro Ala Asp Leu Val Ala Asn Ser Ile
305                 310                 315                 320
```

```
Ile Leu Ser Ala Thr Glu Ala Leu Leu Asp Ser Gly Ala His Arg Ile
                325                 330                 335

Tyr Gln Cys Cys Ser Ser Glu Val Asn Pro Ile Arg Ile Arg Glu Val
            340                 345                 350

Ile Gly His Val Gln Gln Ala Glu His Asn Tyr Gln Thr His Asp
        355                 360                 365

Lys Leu Phe Tyr Arg Lys Pro Lys Lys Pro Phe Val Met Ile Pro Gly
    370                 375                 380

Ala Val Phe His Ala Leu Met Ala Ile Ser Phe His Met Leu Lys Trp
385                 390                 395                 400

Ser Ser Arg Leu Gln Ser Leu Phe Gly Arg Lys Ala Ser Gly Arg Lys
                405                 410                 415

Leu Ser Asn Met Glu Thr Thr Met Lys Leu Ser Lys Val Phe Ser Phe
            420                 425                 430

Tyr Thr Ser Pro Ser Tyr Thr Phe Ser Asn Arg Arg Leu Gln Glu Leu
        435                 440                 445

Ser Thr Arg Leu Gly Glu Tyr Asp Gln Ser Glu Phe Pro Val Asn Ala
    450                 455                 460

Gly Met Tyr Asp Trp Ala His Tyr Leu Arg Glu Val His Val Ala Gly
465                 470                 475                 480

Leu Asn Lys Tyr Ala Leu Arg Pro Lys Val Val Lys Met Asn Pro Pro
                485                 490                 495

Ala Ala Lys Pro Arg Ser Arg Ala Ala
            500                 505

<210> SEQ ID NO 23
<211> LENGTH: 1518
<212> TYPE: DNA
<213> ORGANISM: Hahella chejuensis KCTC 2396

<400> SEQUENCE: 23
ttacgcagcg cggctgcgag gttttgctgc aggcgggttc atcttcacca ctttcggccg      60
cagcgcgtac ttgttcagac ccgccacgtg aacttcccgc aagtagtgcg cccagtcata    120 cataccegca ttcacgggga attcgctctg gtcatattcc ccaagacggg tggatagctc    180
ctgcagacgg cggttgctga aggtatagct gggagaggta tagaaggaaa acaccttgga    240
cagtttcatc gtagtttcca tgttgctcag cttgcgcccg aagccttac ggccaaacaa     300 gctctgcaga cgggaactcc atttcagcat gtggaaactg atcgccatca acgcgtgaaa    360
cacggcgccg ggaatcatta caaagggctt cttcggcttg cggtagaaca gtttgtcgtg    420
cgtctgataa ttgtgctccg cctcttgctg cacatgccca atgacttccc gaatcctgat    480
tggattaacc tcgctgctgc aacactggta gatgcgatgg gcgccggaat ccagcagcgc    540
ttccgtggcg ctcaggatga tgctgttggc caccaggtcc gccggaatga tatcaatgac    600
cgcattcttc ttgccgggaa acaaagacac cttttctctg gcgtaagcga ggatgatcgc    660
atccgccact ttcaccccct caatccagcc cggcgccggt cccagcagcg tactttcaac    720
aatggaaggt cgcaggatgg tcagggtttt gccatacagc tccttcatca gcaactgctc    780
gcccatccat ttagtgaagg tataggtatc gttccaacca tactattgg cttctttgat     840 acccaggtcg ataagatcct tttccctgct atgatcatcc gccgcagcgg cggacacttg    900
ctctacatcc tgcagcaaac gcgcaatcag cggctcaact tcatagtagc gcgttctga    960 acgctcaatg cgttctcccg ccgggctgac gatttcctct ccatcactc cctgattgaa   1020 gccgttgacg tagcaggtgg atacctgcac gacagggcag tccgccgcgc gccgcgacag    1080
```

```
ttcaatgata tttttaaggc acagggtatt gatggtgaga gcctgatcca gcgcttcgcg      1140
gaaattgacg ctggcggctg aattgataat aacgtcgata tctgcggcca ggtcggtaaa      1200
gtccttctcc gacaggccaa acagaggctc cgtcacctct ccggtcacgc agtggatgcg      1260
ggtttcgcac aactcctcga aacgacttcc ctgcgatgcc ttgagagtat cgaaaataga      1320
tgaggtcgcg atctcattct ggaaccgctt tcgcgctgta gggttctttg aattaccccg      1380
tatcagcaaa taaatcttcc caattgtcgg cacgctgcgc agcagcttct ccagtaccac      1440
cttgccgacg aatcccgtcg tccccgtaat cagtacattc ttattagcaa aagcagttaa      1500
cgtaagtgat tgcttcat                                                    1518
```

<210> SEQ ID NO 24
<211> LENGTH: 233
<212> TYPE: PRT
<213> ORGANISM: Oceanobacter sp. RED65

<400> SEQUENCE: 24

```
Met Lys Ile Glu Leu Gln Pro Ile Gly Tyr Ile Asn Ser Pro Tyr His
1               5                   10                  15

Glu Lys Phe Ala Thr Pro Arg Gln Pro Gly Leu Val Ser Gln Ala Gln
                20                  25                  30

Gly Tyr Val Glu Leu Val Ser Pro Tyr Asn Gln Ala Asp Ser Val Ala
            35                  40                  45

Gly Leu Glu Thr Cys Ser His Ile Trp Ile Glu Phe Val Phe His Glu
        50                  55                  60

Val Met Asn Gln Gly Trp Lys Pro Lys Val Arg Pro Pro Arg Leu Gly
65                  70                  75                  80

Gly Asn Glu Lys Met Gly Val Phe Ala Thr Arg Ser Thr His Arg Pro
                85                  90                  95

Asn Pro Ile Gly Leu Ser Val Val Lys Leu Asp Arg Ile Asp Ile Asn
            100                 105                 110

Asn Gly Val Arg Leu Trp Ile Ser Gly Leu Asp Leu Ile Asp Gly Thr
        115                 120                 125

Pro Val Val Asp Ile Lys Pro Tyr Val Pro Tyr Ser Asp Cys Leu Pro
    130                 135                 140

Asp Ala Gln Tyr Pro Phe Ala Gln Asp Lys Pro Ala Ile Asp Val
145                 150                 155                 160

Ile Phe Ser Gln Ala Cys Glu Thr Arg Leu Asn Asn Gln Pro Gln Leu
                165                 170                 175

Lys Thr Phe Leu Leu Gln Val Leu Glu Gln Asp Pro Arg Pro Ala Phe
            180                 185                 190

His Lys Phe Asp Gln Glu Arg Glu Tyr Gly Ala Ala Leu Met Gln His
        195                 200                 205

Asn Val Lys Trp Arg Tyr Gln Lys Asp Asp Ser Gly Asn Ile Ser Leu
    210                 215                 220

Tyr Val Glu Ser Ile Thr Pro Leu Ala
225                 230
```

<210> SEQ ID NO 25
<211> LENGTH: 1545
<212> TYPE: DNA
<213> ORGANISM: Oceanobacter sp. RED65

<400> SEQUENCE: 25

```
ttacgccgct tgcctgatgg tttcgcgctt acgcttttc acatgcttgg gcttcagttc        60
```

```
ctgcctgtcc gctagggcgt atttgtgtag tccatccatg tgtacctctt gcaaataata     120
tttccaatca aagtgatcgg cgcgaatatc gtataagcgc tgttctgtgg tgtcgaactg     180
cttgactaac tgttcaagtt tctgactact aaaacgataa ttaggggcgg tataaaaacc     240
aaaaatattc gccagtgacg ccgtggtttt cgcttttaac atatgctgcg acgcagcgtt     300
ggaaccgaac actcgtccga taatcgtttt tgcccaagtg atagccgtga agccactcat     360
atacaatttg aaacgttttg gggaaaccgt tttgaaggct tcttgtggct tatctgcgaa     420
caattttggc cactcctgat agcgagcttg cgccacgttt tgaatatggc gaataaactc     480
cttcaacttt atgggattgc gactaccgct acagcactga taaatgcgat accccgtctg     540
ctgattagat tccattaatt gcgccgctga caaggctgcc gcattagcca ccaaatccac     600
aggaatgacg tcaaggatgc cttcatcacg acctgggaaa atagaaacac gacccttggc     660
gtaagcgtaa atcaacgcat ccgctacttt cacgccctcg acccaacccg gcgcaggttc     720
acgtacagca ctctcgataa tactcggacg caaaatagtt aaactctgct tacccagttt     780
ttgaatgagt agctgctcac ctaaccactt tgtgaatgta taggtatcgt tccaaccaaa     840
atgctggctg gtctttatgc ctaatttaat cagtgcttgt tcttgttgtt ctatgtctgt     900
tttgcgcttt ttgacctgct ctatctggct atgtactcgt ttaaaaaccg aatcgatgtc     960
ataacaatcc tgagacaact gtgggatcag tccgcttgct ggaccaacca cttcttcatt    1020
gatttgacct ttattgaaac cgtttacata acatgtagat atctgcatca ccggcgtttg    1080
agcggccaca ttgtactgcg ctaacgcaat gatattgttt aaacacaagg tgttgatgtt    1140
gagcgctttc tcaaggtttt cgcggaaatt aacactggca gcggagttaa taattaagtc    1200
cagttgattg gccaaacccg caaattcagc actaggcaaa tcaaacatgg gttgtgtcaa    1260
ttcaccttcc accagattga tttttgattg cacccattct tcaaagtgct cgccatgctg    1320
ctctttcagg cgctcaaaaa tactggagcc gaggatatcg tgttgaaaac gcttttttggc    1380
tgaaactttg ccaccgcgca ccaaaatgtg gatttgtgct agctgcggta cactgtacaa    1440
gagcttttct aaaatagctt tgcctaaaaa acctgtcaca cccgttaaaa agatgtgctt    1500
accttttgaga gactgagaca ctgaaaatgc agaatactga ctcat                   1545
```

<210> SEQ ID NO 26
<211> LENGTH: 661
<212> TYPE: PRT
<213> ORGANISM: Marinobacter aquaeolei VT8

<400> SEQUENCE: 26

Met Asn Tyr Phe Leu Thr Gly Gly Thr Gly Phe Ile Gly Arg Phe Leu
1               5                   10                  15

Val Glu Lys Leu Leu Ala Arg Gly Gly Thr Val Tyr Val Leu Val Arg
            20                  25                  30

Glu Gln Ser Gln Asp Lys Leu Glu Arg Leu Arg Glu Arg Trp Gly Ala
        35                  40                  45

Asp Asp Lys Gln Val Lys Ala Val Ile Gly Asp Leu Thr Ser Lys Asn
    50                  55                  60

Leu Gly Ile Asp Ala Lys Thr Leu Lys Ser Leu Lys Gly Asn Ile Asp
65                  70                  75                  80

His Val Phe His Leu Ala Ala Val Tyr Asp Met Gly Ala Asp Glu Glu
                85                  90                  95

Ala Gln Ala Ala Thr Asn Ile Glu Gly Thr Arg Ala Ala Val Gln Ala
            100                 105                 110

Ala Glu Ala Met Gly Ala Lys His Phe His His Val Ser Ser Ile Ala

```
                    115                 120                 125
    Ala Ala Gly Leu Phe Lys Gly Ile Phe Arg Glu Asp Met Phe Glu Glu
    130                 135                 140
    Ala Glu Lys Leu Asp His Pro Tyr Leu Arg Thr Lys His Glu Ser Glu
145                 150                 155                 160
    Lys Val Val Arg Glu Cys Lys Val Pro Phe Arg Ile Tyr Arg Pro
                    165                 170                 175
    Gly Met Val Ile Gly His Ser Glu Thr Gly Met Asp Lys Val Asp
                    180                 185                 190
    Gly Pro Tyr Tyr Phe Phe Lys Met Ile Gln Lys Ile Arg His Ala Leu
                    195                 200                 205
    Pro Gln Trp Val Pro Thr Ile Gly Ile Glu Gly Arg Leu Asn Ile
        210                 215                 220
    Val Pro Val Asp Phe Val Asp Ala Leu Asp His Ile Ala His Leu
225                 230                 235                 240
    Glu Gly Glu Asp Gly Asn Cys Phe His Leu Val Asp Ser Asp Pro Tyr
                    245                 250                 255
    Lys Val Gly Glu Ile Leu Asn Ile Phe Cys Glu Ala Gly His Ala Pro
                    260                 265                 270
    Arg Met Gly Met Arg Ile Asp Ser Arg Met Phe Gly Phe Ile Pro Pro
                    275                 280                 285
    Phe Ile Arg Gln Ser Ile Lys Asn Leu Pro Pro Val Lys Arg Ile Thr
            290                 295                 300
    Gly Ala Leu Leu Asp Asp Met Gly Ile Pro Pro Ser Val Met Ser Phe
305                 310                 315                 320
    Ile Asn Tyr Pro Thr Arg Phe Asp Thr Arg Glu Leu Glu Arg Val Leu
                    325                 330                 335
    Lys Gly Thr Asp Ile Glu Val Pro Arg Leu Pro Ser Tyr Ala Pro Val
                    340                 345                 350
    Ile Trp Asp Tyr Trp Glu Arg Asn Leu Asp Pro Asp Leu Phe Lys Asp
                    355                 360                 365
    Arg Thr Leu Lys Gly Thr Val Glu Gly Lys Val Cys Val Val Thr Gly
        370                 375                 380
    Ala Thr Ser Gly Ile Gly Leu Ala Thr Ala Glu Lys Leu Ala Glu Ala
385                 390                 395                 400
    Gly Ala Ile Leu Val Ile Gly Ala Arg Thr Lys Glu Thr Leu Asp Glu
                        405                 410                 415
    Val Ala Ala Ser Leu Glu Ala Lys Gly Gly Asn Val His Ala Tyr Gln
                    420                 425                 430
    Cys Asp Phe Ser Asp Met Asp Asp Cys Asp Arg Phe Val Lys Thr Val
                    435                 440                 445
    Leu Asp Asn His Gly His Val Asp Val Leu Val Asn Asn Ala Gly Arg
                    450                 455                 460
    Ser Ile Arg Arg Ser Leu Ala Leu Ser Phe Asp Arg Phe His Asp Phe
465                 470                 475                 480
    Glu Arg Thr Met Gln Leu Asn Tyr Phe Gly Ser Val Arg Leu Ile Met
                    485                 490                 495
    Gly Phe Ala Pro Ala Met Leu Glu Arg Arg Gly His Val Val Asn
                    500                 505                 510
    Ile Ser Ser Ile Gly Val Leu Thr Asn Ala Pro Arg Phe Ser Ala Tyr
            515                 520                 525
    Val Ser Ser Lys Ser Ala Leu Asp Ala Phe Ser Arg Cys Ala Ala Ala
        530                 535                 540
```

```
Glu Trp Ser Asp Arg Asn Val Thr Phe Thr Thr Ile Asn Met Pro Leu
545                 550                 555                 560

Val Lys Thr Pro Met Ile Ala Pro Thr Lys Ile Tyr Asp Ser Val Pro
                565                 570                 575

Thr Leu Thr Pro Asp Glu Ala Ala Gln Met Val Ala Asp Ala Ile Val
            580                 585                 590

Tyr Arg Pro Lys Arg Ile Ala Thr Arg Leu Gly Val Phe Ala Gln Val
        595                 600                 605

Leu His Ala Leu Ala Pro Lys Met Gly Glu Ile Ile Met Asn Thr Gly
    610                 615                 620

Tyr Arg Met Phe Pro Asp Ser Pro Ala Ala Gly Ser Lys Ser Gly
625                 630                 635                 640

Glu Lys Pro Lys Val Ser Thr Glu Gln Val Ala Phe Ala Ala Ile Met
                645                 650                 655

Arg Gly Ile Tyr Trp
            660

<210> SEQ ID NO 27
<211> LENGTH: 1986
<212> TYPE: DNA
<213> ORGANISM: Marinobacter aquaeolei VT8

<400> SEQUENCE: 27
ttaccagtat atccccgca taatcgccgc aaaggccacc tgctcggtag agactttcgg     60
cttttcgccg gacttgctgc cagcggctgc tggagaatcc gggaacatcc ggtagccagt    120
gttcataatg atctcaccca tcttcggtgc cagcgcatgc agaacctgcg cgaacacgcc    180
aagacgggtg gcaatgcgct ggggccggta cacaatcgca tccgccacca tctgggcggc    240
ttcatccggc gtcagcgtcg gcacggaatc gtagatcttg gtgggcgcga tcatcggcgt    300
tttcaccaac ggcatgttga tggtggtgaa ggtcacgttg cgatccgacc attctgcagc    360
ggcacagcgg ctgaacgcgt ccagtgcgga tttcgaggag acataggccg agaaacgcgg    420
agcgttggta agtaccccga tggaagaaat attcaccacg tgcccgcggc gacgctccag    480
catggctggc gcaaagccca tgatcagccg aacggagcca agtagttca gctgcatggt    540 ccgctcaaaa tcgtggaacc ggtcaaaaga caacgccagc gagcggcgga tggagcgacc    600
cgcgttattc accagtacat ccacgtggcc gtgattatcc agcaccgtct tcacaaagcg    660
gtcgcagtcg tccatgtccg aaaagtcgca ctggtacgca tgcacgttgc caccccttggc    720 ctccagactg gccgccactt catccagagt ttccttggtg cgcgcaccaa tgaccagaat    780
ggcaccggcc tctgccagct tctctgccgt tgccaggcca atacccgagg tcgcgccggt    840
gaccacgcaa accttacctt caaccgtgcc cttgagggtg cggtccttga acaggtccgg    900
gtccagattg cgctcccagt agtcccagat aaccggggca taggacggca gacgcggcac    960
ctcaatgtct gtgcccttca gaacccgctc cagctcccgg gtatcaaaac gggtcgggta   1020
attaatgaag gacatcaccg agggcggaat gcccatgtca tccagaagcg caccagtaat   1080
gcgcttgacc ggaggcagat tcttgatgct ctggcgaata acggcggaa taaaaccgaa    1140 catccgggaa tcgatgcgca tacccatgcg gggggcatgg ccggcctcgc agaaaatatt   1200
gaggatctca cccaccttat acggatcgga gtccaccaga tggaaacagt tgccatcttc   1260
gccttccaga tgggcaatgt gatccagtgc atcgaccacg aaatccaccg gcacaatgtt   1320
cagccggcca ccttcaatac cgatggtggg tacccactgg ggcaacgcat gacggatctt   1380
ctgaatcatc ttgaagaagt aatagggccc gtcaaccttg tccatttcgc cggtttccga   1440
```

-continued

```
atggccaatg accataccag ggcggtagat gcggaacgga accttgcatt cttcacgcac   1500 aacttttcg gattcgtgct tggtgcgcag gtaaggatga tcaagcttct cggcttcttc    1560
gaacatatcc tcccggaaga tacccttgaa cagacccgct gccgcgatgg atgacacatg   1620
atggaaatgc ttggcgccca tggcttcggc ggcctgaaca gccgcccgg tgccttcgat    1680 attggtggcg gcctgggctt cttcgtctgc gcccatgtcg tagaccgcgg caagatggaa   1740
tacgtggtcg atatttcctt tcagtgattt cagcgttttc gcgtcaatac caaggttttt   1800
gctggtgagg tcgccgatca cagccttcac ttgcttgtcg tctgcacccc agcgctcccg   1860
gagccgctcc agcttgtcct gggactgctc gcgaaccaga acatacacgg tgccgccgcg   1920
cgccaagagt ttctcaacca gaaaacgacc gataaaaccg gtgccgcctg tcaggaaata   1980
attcat                                                              1986
```

<210> SEQ ID NO 28
<211> LENGTH: 480
<212> TYPE: PRT
<213> ORGANISM: Artificial sequence
<220> FEATURE:
<223> OTHER INFORMATION: Synthetic construct: Truncated FAR6 protein

<400> SEQUENCE: 28

```
Met Arg Asn Ser Asp Gly Ile Gly Ile Val Arg Phe Leu Glu Gly Lys
1               5                   10                  15

Ser Tyr Leu Val Thr Gly Ala Thr Gly Phe Leu Ala Lys Val Leu Ile
            20                  25                  30

Glu Lys Leu Leu Arg Glu Ser Leu Glu Ile Gly Lys Ile Phe Leu Leu
        35                  40                  45

Met Arg Ser Lys Asp Gln Glu Ser Ala Asn Lys Arg Leu Tyr Asp Glu
    50                  55                  60

Ile Ile Ser Ser Asp Leu Phe Lys Leu Leu Lys Gln Met His Gly Ser
65                  70                  75                  80

Ser Tyr Glu Ala Phe Met Lys Arg Lys Leu Ile Pro Val Ile Gly Asp
                85                  90                  95

Ile Glu Glu Asp Asn Leu Gly Ile Lys Ser Glu Ile Ala Asn Met Ile
            100                 105                 110

Ser Glu Glu Ile Asp Val Ile Ile Ser Cys Gly Gly Arg Thr Thr Phe
        115                 120                 125

Asp Asp Arg Tyr Asp Ser Ala Leu Ser Val Asn Ala Leu Gly Pro Gly
    130                 135                 140

Arg Leu Leu Ser Phe Gly Lys Gly Cys Arg Lys Leu Lys Leu Phe Leu
145                 150                 155                 160

His Phe Ser Thr Ala Tyr Val Thr Gly Lys Arg Glu Gly Thr Val Leu
                165                 170                 175

Glu Thr Pro Leu Cys Ile Gly Glu Asn Ile Thr Ser Asp Leu Asn Ile
            180                 185                 190

Lys Ser Glu Leu Lys Leu Ala Ser Glu Ala Val Arg Lys Phe Arg Gly
        195                 200                 205

Arg Glu Glu Ile Lys Lys Leu Lys Glu Leu Gly Phe Glu Arg Ala Gln
    210                 215                 220

His Tyr Gly Trp Glu Asn Ser Tyr Thr Phe Thr Lys Ala Ile Gly Glu
225                 230                 235                 240

Ala Val Ile His Ser Lys Arg Gly Asn Leu Pro Val Val Ile Arg
                245                 250                 255

Pro Ser Ile Ile Glu Ser Ser Tyr Asn Glu Pro Phe Pro Gly Trp Ile
            260                 265                 270
```

```
Gln Gly Thr Arg Met Ala Asp Pro Ile Ile Leu Ala Tyr Ala Lys Gly
            275                 280                 285

Gln Ile Ser Asp Phe Trp Ala Asp Pro Gln Ser Leu Met Asp Ile Ile
            290                 295                 300

Pro Val Asp Met Val Ala Asn Ala Ala Ile Ala Met Ala Lys His
305                 310                 315                 320

Gly Cys Gly Val Pro Glu Phe Lys Val Tyr Asn Leu Thr Ser Ser
                325                 330                 335

His Val Asn Pro Met Arg Ala Gly Lys Leu Ile Asp Leu Ser His Gln
            340                 345                 350

His Leu Cys Asp Phe Pro Leu Glu Glu Thr Val Ile Asp Leu Glu His
            355                 360                 365

Met Lys Ile His Ser Ser Leu Glu Gly Phe Thr Ser Ala Leu Ser Asn
            370                 375                 380

Thr Ile Ile Lys Gln Glu Arg Val Ile Asp Asn Glu Gly Gly Gly Leu
385                 390                 395                 400

Ser Thr Lys Gly Lys Arg Lys Leu Asn Tyr Phe Val Ser Leu Ala Lys
                405                 410                 415

Thr Tyr Glu Pro Tyr Thr Phe Phe Gln Ala Arg Phe Asp Asn Thr Asn
                420                 425                 430

Thr Thr Ser Leu Ile Gln Glu Met Ser Met Glu Glu Lys Lys Thr Phe
            435                 440                 445

Gly Phe Asp Ile Lys Gly Ile Asp Trp Glu His Tyr Ile Val Asn Val
            450                 455                 460

His Leu Pro Gly Leu Lys Lys Glu Phe Leu Ser Lys Lys Lys Thr Glu
465                 470                 475                 480

<210> SEQ ID NO 29
<211> LENGTH: 3150
<212> TYPE: DNA
<213> ORGANISM: Artificial sequence
<220> FEATURE:
<223> OTHER INFORMATION: Synthetic construct: FadD-Truncated FAR6 operon

<400> SEQUENCE: 29
atggccaaga aggtttggct taaccgttat cccgcggacg ttccgacgga gatcaaccct       60
gaccgttatc aatctctggt agatatgttt gagcagtcgg tcgcgcgcta cgccgatcaa      120
cctgcgtttg tgaatatggg ggaggtaatg accttccgca agctggaaga acgcagtcgc      180
gcgtttgccg cttatttgca acaagggttg gggctgaaga aaggcgatcg cgttgcgttg      240
atgatgccta atttattgca atatccggtg gcgctgtttg gcattttgcg tgccgggatg      300
atcgtcgtaa acgttaaccc gttgtatacc ccgcgtgagc ttgagcatca gcttaacgat      360
agcggcgcat cggcgattgt tatcgtgtct aactttgctc acacactgga aaaagtggtt      420
gataaaaccg ccgttcagca cgtaattctg acccgtatgg gcgatcagct atctacggca      480
aaaggcacgg tagtcaattt cgttgttaaa tacatcaagc gtttggtgcc gaaataccat      540
ctgccagatg ccatttcatt tcgtagcgca ctgcataacg gctaccggat gcagtacgtc      600
aaacccgaac tggtgccgga agatttagct tttctgcaat acaccggcgg caccactggt      660
gtggcgaaag gcgcgatgct gactcaccgc aatatgctgg cgaacctgga acaggttaac      720
gcgacctatg gtccgctgtt gcatccgggc aaagagctgg tggtgacggc gctgccgctg      780
tatcacattt ttgccctgac cattaactgc ctgctgttta tcgaactggg tgggcagaac      840
ctgcttatca ctaacccgcg cgatattcca gggttggtaa aagagttagc gaaatatccg      900
```

-continued

```
tttaccgcta tcacgggcgt taacaccttg ttcaatgcgt tgctgaacaa taaagagttc      960
cagcagctgg atttctccag tctgcatctt tccgcaggcg gtgggatgcc agtgcagcaa     1020
gtggtggcag agcgttgggt gaaactgacc ggacagtatc tgctggaagg ctatggcctt     1080
accgagtgtg cgccgctggt cagcgttaac ccatatgata ttgattatca tagtggtagc     1140
atcggtttgc cggtgccgtc gacggaagcc aaactggtgg atgatgatga taatgaagta     1200
ccaccaggtc aaccgggtga gctttgtgtc aaaggaccgc aggtgatgct gggttactgg     1260
cagcgtcccg atgctaccga tgaaatcatc aaaaatggct ggttacacac cggcgacatc     1320
gcggtaatgg atgaagaagg attcctgcgc attgtcgatc gtaaaaaaga catgattctg     1380
gtttccggtt ttaacgtcta tcccaacgag attgaagatg tcgtcatgca gcatcctggc     1440
gtacaggaag tcgcggctgt tggcgtacct tccggctcca gtggtgaagc ggtgaaaatc     1500
ttcgtagtga aaaagatcc atcgcttacc gaagagtcac tggtgacttt tgccgccgt     1560 cagctcacgg gatacaaagt accgaagctg gtggagtttc gtgatgagtt accgaaatct     1620
aacgtcggaa aaattttgcg acgagaatta cgtgacgaag cgcgcggcaa agtggacaat     1680
aaagcctgag gatccaggag gatcattact atgcggaaca gcgatggtat tggcattgtt     1740
cggtttctcg aaggtaaatc ctacttggtg accggtgcca ccggttttct ggccaaagtg     1800
ctgattgaga aactgctccg tgagtccctc gaaatcggta agatcttctt gttgatgcgg     1860
tccaaagacc aagaaagtgc gaacaagcgg ctgtatgatg agatcatttc ttctgatctg     1920
ttcaagctcc tgaaacaaat gcacggtagc tcctatgaag cctttatgaa gcgcaaactc     1980
attcccgtta ttggtgacat tgaagaagat aacctcggca tcaaaagtga aattgctaac     2040
atgatttccg aagaaatcga tgtaatcatc tcctgtggtg gtcgcactac ttttgacgac     2100
cgttatgata gtgctttaag cgtcaatgct ttgggccctg gccgtctgtt gagcttcggc     2160
aagggctgcc ggaaactcaa actctttttg cacttttcca ccgcctacgt gaccgggaaa     2220
cgcgagggga ctgtgttaga aaccccgtta tgtattggcg aaaacattac cagtgacttg     2280
aatatcaaat ccgaattgaa gttggcctcc gaagctgttc ggaagtttcg gggtcgggaa     2340
gagattaaga aattgaaaga attgggtttc gaacgtgcgc aacattacgg ctgggagaac     2400
tcctataccT ttaccaaagc gattggtgaa gcggttattc atagtaaacg cggtaatctc     2460
cccgtcgtga ttatccgtcc ttccattatc gaatcttctt acaacgagcc ctttcctggt     2520
tggattcaag gcacccggat ggctgatccc atcattctcg cttacgccaa agggcagatt     2580
tctgacttct gggccgaccc ccaatcctta atggacatca ttccggtcga tatggtagcc     2640
aatgccgcca ttgctgcgat ggctaagcac ggttgcggcg ttcccgagtt caaagtgtac     2700
aacttgacca gtagctccca tgtgaaccct atgcgggctg gcaaactgat tgatctgtcc     2760
caccagcatt tgtgcgattt tcccctcgaa gaaaccgtga tcgacttgga acacatgaag     2820
atccatagta gcttagaagg ctttactagc gccttgagca acaccatcat caaacaggaa     2880
cgcgttatcg acaacgaagg gggtggctta tccaccaaag ggaaacgcaa gctcaactac     2940
ttcgtaagcc tcgccaagac ctacgaaccc tacaccttct tccaagcccg gttcgacaac     3000
actaacacca ccagcttgat tcaggaaatg tctatggaag agaagaaaac ttttggtttt     3060
gacattaagg ggattgattg ggaacactat atcgtgaatg tgcacctccc cggtctgaag     3120
aaagaattct tgtccaaaaa gaaaaccgaa                                      3150
```

<210> SEQ ID NO 30
<211> LENGTH: 616
<212> TYPE: PRT

<213> ORGANISM: Arabidopsis thaliana

<400> SEQUENCE: 30

```
Met Glu Ala Leu Phe Leu Ser Ser Ser Ser Ile Val Ala Ser
1               5                   10                  15

Asn Lys Leu Thr Arg Leu His Asn His Cys Val Trp Ser Thr Val Ile
            20                  25                  30

Arg Asp Lys Lys Arg Phe Gly Pro Thr Trp Cys Arg Val Gly Gly Gly
        35                  40                  45

Gly Asp Gly Gly Arg Asn Ser Asn Ala Glu Arg Pro Ile Arg Val Ser
    50                  55                  60

Ser Leu Leu Lys Asp Arg Gly Gln Val Leu Ile Arg Glu Gln Ser Ser
65                  70                  75                  80

Pro Ala Met Asp Ala Glu Thr Leu Val Leu Ser Pro Asn Gly Asn Gly
                85                  90                  95

Arg Thr Ile Glu Ile Asn Gly Val Lys Thr Leu Met Pro Phe Ser Gly
            100                 105                 110

Ala Ser Met Val Gly Met Lys Glu Gly Leu Gly Ile Ile Ser Phe Leu
        115                 120                 125

Gln Gly Lys Lys Phe Leu Ile Thr Gly Ser Thr Gly Phe Leu Ala Lys
    130                 135                 140

Val Leu Ile Glu Lys Val Leu Arg Met Ala Pro Asp Val Ser Lys Ile
145                 150                 155                 160

Tyr Leu Leu Ile Lys Ala Lys Ser Lys Glu Ala Ile Glu Arg Leu
                165                 170                 175

Lys Asn Glu Val Leu Asp Ala Glu Leu Phe Asn Thr Leu Lys Glu Thr
            180                 185                 190

His Gly Ala Ser Tyr Met Ser Phe Met Leu Thr Lys Leu Ile Pro Val
        195                 200                 205

Thr Gly Asn Ile Cys Asp Ser Asn Ile Gly Leu Gln Ala Asp Ser Ala
    210                 215                 220

Glu Glu Ile Ala Lys Glu Val Asp Val Ile Asn Ser Ala Ala Asn
225                 230                 235                 240

Thr Thr Phe Asn Glu Arg Tyr Asp Val Ala Leu Asp Ile Asn Thr Arg
                245                 250                 255

Gly Pro Gly Asn Leu Met Gly Phe Ala Lys Lys Cys Lys Lys Leu Lys
            260                 265                 270

Leu Phe Leu Gln Val Ser Thr Ala Tyr Val Asn Gly Gln Arg Gln Gly
        275                 280                 285

Arg Ile Met Glu Lys Pro Phe Ser Met Gly Asp Cys Ile Ala Thr Glu
    290                 295                 300

Asn Phe Leu Glu Gly Asn Arg Lys Ala Leu Asp Val Asp Arg Glu Met
305                 310                 315                 320

Lys Leu Ala Leu Glu Ala Ala Arg Lys Gly Thr Gln Asn Gln Asp Glu
                325                 330                 335

Ala Gln Lys Met Lys Asp Leu Gly Leu Glu Arg Ala Arg Ser Tyr Gly
            340                 345                 350

Trp Gln Asp Thr Tyr Val Phe Thr Lys Ala Met Gly Glu Met Met Ile
        355                 360                 365

Asn Ser Thr Arg Gly Asp Val Pro Val Val Ile Arg Pro Ser Val
    370                 375                 380

Ile Glu Ser Thr Tyr Lys Asp Pro Phe Pro Gly Trp Met Glu Gly Asn
385                 390                 395                 400

Arg Met Met Asp Pro Ile Val Leu Cys Tyr Gly Lys Gly Gln Leu Thr
```

-continued

```
                    405                 410                 415
Gly Phe Leu Val Asp Pro Lys Gly Val Leu Asp Val Val Pro Ala Asp
                420                 425                 430

Met Val Val Asn Ala Thr Leu Ala Ala Ile Ala Lys His Gly Met Ala
            435                 440                 445

Met Ser Asp Pro Glu Pro Glu Ile Asn Val Tyr Gln Ile Ala Ser Ser
        450                 455                 460

Ala Ile Asn Pro Leu Val Phe Glu Asp Leu Ala Glu Leu Leu Tyr Asn
465                 470                 475                 480

His Tyr Lys Thr Ser Pro Cys Met Asp Ser Lys Gly Asp Pro Ile Met
                485                 490                 495

Val Arg Leu Met Lys Leu Phe Asn Ser Val Asp Asp Phe Ser Asp His
                500                 505                 510

Leu Trp Arg Asp Ala Gln Glu Arg Ser Gly Leu Met Ser Gly Met Ser
            515                 520                 525

Ser Val Asp Ser Lys Met Met Gln Lys Leu Lys Phe Ile Cys Lys Lys
        530                 535                 540

Ser Val Glu Gln Ala Lys His Leu Ala Thr Ile Tyr Glu Pro Tyr Thr
545                 550                 555                 560

Phe Tyr Gly Gly Arg Phe Asp Asn Ser Asn Thr Gln Arg Leu Met Glu
                565                 570                 575

Asn Met Ser Glu Asp Glu Lys Arg Glu Phe Gly Phe Asp Val Gly Ser
            580                 585                 590

Ile Asn Trp Thr Asp Tyr Ile Thr Asn Val His Ile Pro Gly Leu Arg
        595                 600                 605

Arg His Val Leu Lys Gly Arg Ala
    610                 615

<210> SEQ ID NO 31
<211> LENGTH: 502
<212> TYPE: PRT
<213> ORGANISM: Artificial sequence
<220> FEATURE:
<223> OTHER INFORMATION: Synthetic construct: Truncated MS2 protein

<400> SEQUENCE: 31

Met Val Gly Met Lys Glu Gly Leu Gly Ile Ile Ser Phe Leu Gln Gly
1               5                   10                  15

Lys Lys Phe Leu Ile Thr Gly Ser Thr Gly Phe Leu Ala Lys Val Leu
                20                  25                  30

Ile Glu Lys Val Leu Arg Met Ala Pro Asp Val Ser Lys Ile Tyr Leu
            35                  40                  45

Leu Ile Lys Ala Lys Ser Lys Glu Ala Ala Ile Glu Arg Leu Lys Asn
        50                  55                  60

Glu Val Leu Asp Ala Glu Leu Phe Asn Thr Leu Lys Glu Thr His Gly
65                  70                  75                  80

Ala Ser Tyr Met Ser Phe Met Leu Thr Lys Leu Ile Pro Val Thr Gly
                85                  90                  95

Asn Ile Cys Asp Ser Asn Ile Gly Leu Gln Ala Asp Ser Ala Glu Glu
            100                 105                 110

Ile Ala Lys Glu Val Asp Val Ile Ile Asn Ser Ala Ala Asn Thr Thr
        115                 120                 125

Phe Asn Glu Arg Tyr Asp Val Ala Leu Asp Ile Asn Thr Arg Gly Pro
    130                 135                 140

Gly Asn Leu Met Gly Phe Ala Lys Lys Cys Lys Lys Leu Lys Leu Phe
145                 150                 155                 160
```

-continued

```
Leu Gln Val Ser Thr Ala Tyr Val Asn Gly Gln Arg Gln Gly Arg Ile
            165                 170                 175
Met Glu Lys Pro Phe Ser Met Gly Asp Cys Ile Ala Thr Glu Asn Phe
            180                 185                 190
Leu Glu Gly Asn Arg Lys Ala Leu Asp Val Asp Arg Glu Met Lys Leu
            195                 200                 205
Ala Leu Glu Ala Ala Arg Lys Gly Thr Gln Asn Gln Asp Glu Ala Gln
210                 215                 220
Lys Met Lys Asp Leu Gly Leu Glu Arg Ala Arg Ser Tyr Gly Trp Gln
225                 230                 235                 240
Asp Thr Tyr Val Phe Thr Lys Ala Met Gly Glu Met Met Ile Asn Ser
            245                 250                 255
Thr Arg Gly Asp Val Pro Val Val Ile Ile Arg Pro Ser Val Ile Glu
            260                 265                 270
Ser Thr Tyr Lys Asp Pro Phe Pro Gly Trp Met Glu Gly Asn Arg Met
            275                 280                 285
Met Asp Pro Ile Val Leu Cys Tyr Gly Lys Gly Gln Leu Thr Gly Phe
290                 295                 300
Leu Val Asp Pro Lys Gly Val Leu Asp Val Val Pro Ala Asp Met Val
305                 310                 315                 320
Val Asn Ala Thr Leu Ala Ala Ile Ala Lys His Gly Met Ala Met Ser
            325                 330                 335
Asp Pro Glu Pro Glu Ile Asn Val Tyr Gln Ile Ala Ser Ser Ala Ile
            340                 345                 350
Asn Pro Leu Val Phe Glu Asp Leu Ala Glu Leu Leu Tyr Asn His Tyr
            355                 360                 365
Lys Thr Ser Pro Cys Met Asp Ser Lys Gly Asp Pro Ile Met Val Arg
            370                 375                 380
Leu Met Lys Leu Phe Asn Ser Val Asp Asp Phe Ser Asp His Leu Trp
385                 390                 395                 400
Arg Asp Ala Gln Glu Arg Ser Gly Leu Met Ser Gly Met Ser Ser Val
            405                 410                 415
Asp Ser Lys Met Met Gln Lys Leu Lys Phe Ile Cys Lys Lys Ser Val
            420                 425                 430
Glu Gln Ala Lys His Leu Ala Thr Ile Tyr Glu Pro Tyr Thr Phe Tyr
            435                 440                 445
Gly Gly Arg Phe Asp Asn Ser Asn Thr Gln Arg Leu Met Glu Asn Met
450                 455                 460
Ser Glu Asp Glu Lys Arg Glu Phe Gly Phe Asp Val Gly Ser Ile Asn
465                 470                 475                 480
Trp Thr Asp Tyr Ile Thr Asn Val His Ile Pro Gly Leu Arg Arg His
            485                 490                 495
Val Leu Lys Gly Arg Ala
            500
```